(12) United States Patent
Persons et al.

(10) Patent No.: US 6,548,637 B1
(45) Date of Patent: Apr. 15, 2003

(54) LIGANDS FOR OPIOID RECEPTORS

(75) Inventors: Paul E. Persons, Westborough, MA (US); James R. Hauske, Hopkington, MA (US); Roushan A. Hussoin, Lexington, MA (US)

(73) Assignee: Sepracor, Inc., Marlborough, MA (US)

( * ) Notice: Subject to any disclaimer, the term of this patent is extended or adjusted under 35 U.S.C. 154(b) by 0 days.

(21) Appl. No.: 09/336,314

(22) Filed: Jun. 18, 1999

Related U.S. Application Data

(60) Provisional application No. 60/089,792, filed on Jun. 18, 1998.

(51) Int. Cl.[7] ................................................. C07K 5/08
(52) U.S. Cl. ......................... 530/331; 514/18; 514/19; 562/445
(58) Field of Search ..................... 514/18, 19; 530/331; 562/445

(56) References Cited

U.S. PATENT DOCUMENTS

| | | | | |
|---|---|---|---|---|
| 4,829,053 A | * | 5/1989 | Raddatz | 514/18 |
| 5,284,828 A | * | 2/1994 | Hemmi | 514/18 |
| 5,538,950 A | * | 7/1996 | Hemmi | 514/18 |
| 5,552,404 A | | 9/1996 | Chang et al. | 514/255 |
| 5,574,159 A | | 11/1996 | Chang et al. | 544/396 |
| 5,646,151 A | | 7/1997 | Kruse et al. | 514/255 |
| 5,656,604 A | * | 8/1997 | Hemmi | 514/18 |
| 5,658,908 A | | 8/1997 | Chang et al. | 514/252 |
| 5,681,830 A | | 10/1997 | Chang et al. | 514/85 |
| 5,688,955 A | | 11/1997 | Kruse et al. | 546/276.4 |
| 5,744,458 A | | 4/1998 | Kruse et al. | 514/91 |
| 5,750,646 A | | 5/1998 | Coy et al. | 530/314 |
| 5,760,023 A | | 6/1998 | Farrar et al. | 514/150 |
| 5,763,445 A | | 6/1998 | Kruse et al. | 514/255 |

FOREIGN PATENT DOCUMENTS

| | | |
|---|---|---|
| WO | WO 93/15062 | 8/1993 |
| WO | WO 95/22557 | 8/1995 |
| WO | WO 96/40208 | 12/1996 |
| WO | WO 97/09973 | 3/1997 |
| WO | WO 97/32857 | 9/1997 |
| WO | WO97/46240 | 12/1997 |
| WO | WO 98/42732 | 10/1998 |

OTHER PUBLICATIONS

Hackler et al., "Isolation of Relatively Large Amounts of Endomorphin–1 and Endomorphin–2 From Human Brain Cortex", Peptides 18(10):1635–1639 (1997).
Martin–Schild et al., "Localization of Endomorphin–2–Like Immunoreactivity in the Rat Medulla and Spinal Cord", Peptides 18(10):1641–1649 (1997).
Okuda–Ashitaka et al., "Nocistatin, a Peptide that Blocks Nociceptin Action in Pain Transmission", Nature, 392:286–289 (Mar. 19, 1998).
Simon et al., "Peptoids: A Modular Approach to Drug Discovery", Proc. Natl. Acad. Sci. USA 89: 9367–9371 (Oct. 1992).
Zuckermann et al., "Discovery of Nanomolar Ligands for 7–Transmembrane G–Protein–Coupled Receptor From a Diverse N–(Substituted)Glycine Peptoid Library", J. Med. Chem. 37:2678–2685 (1994).
Sakaguchi et al., "Receptor Interactions of Synthetic Morphiceptin Analogs Containing Phenylalanine Homologs in Position 4", The Bull. Chem. Soc. Jpn., 65 (4): 1052–1056 (1992).
Zadina et al., "A potent and selective endogenous agonist for the $\mu$–opiaate receptor", Nature 386:499–502 (Apr. 3, 1997).
International Search Report, PCT/US99/13638.
Chem. Abstr. 125, 317636, 1995.*
Chem. Abstr. 115, 105427, 1990.*

* cited by examiner

*Primary Examiner*—David Lukton
(74) *Attorney, Agent, or Firm*—Dana M. Gordon; Foley, Hoag & Eliot LLP

(57) ABSTRACT

The present invention provides compounds, and pharmaceutical preparations thereof, that bind selectively to mammalian opioid receptors. The present set of compounds comprises full agonists, partial agonists, and antagonists of mammalian opioid receptors.

79 Claims, 40 Drawing Sheets

Structures of Twenty Endomorphin-2 Analogues (51-70)

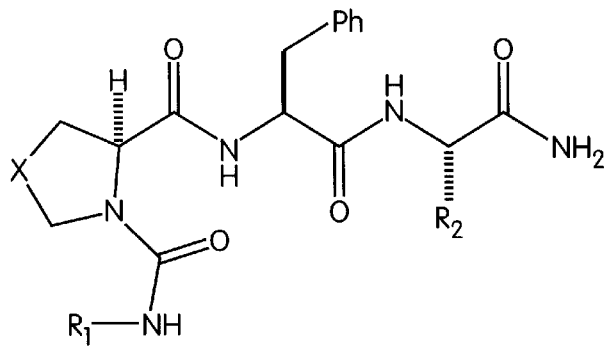

51 (X=CH$_2$; R$_1$=3-methoxyphenyl; R$_2$=4-fluorobenzyl)
52 (X=CH$_2$; R$_1$=3-methoxyphenyl; R$_2$=4-phenylbenzyl)
53 (X=CH$_2$; R$_1$=3-methoxyphenyl; R$_2$=diphenylmethyl)
54 (X=CH$_2$; R$_1$=3-methoxyphenyl; R$_2$=3,4-dichlorobenzyl)
55 (X=S; R$_1$=2,5-difluorophenyl; R$_2$=diphenylmethyl)
56 (X=S; R$_1$=3-methoxyphenyl; R$_2$=diphenylmethyl)

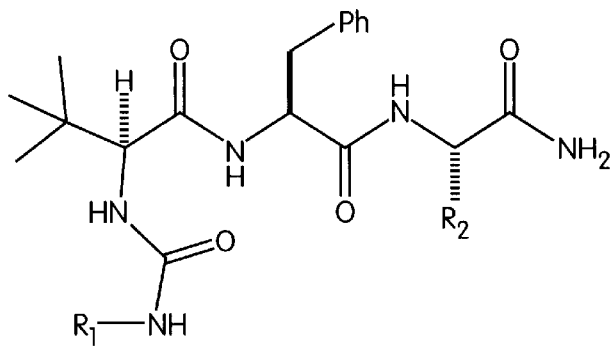

57 (R$_1$=3-methoxyphenyl; R$_2$=3-chlorobenzyl)
58 (R$_1$=3-trifluoromethylphenyl; R$_2$=3-chlorobenzyl)
59 (R$_1$=2,5-difluorophenyl; R$_2$=3-chlorobenzyl)
60 (R$_1$=3-methoxyphenyl; R$_2$=diphenylmethyl)
61 (R$_1$=3-trifluoromethylphenyl; R$_2$=diphenylmethyl)
62 (R$_1$=2,5-difluorophenyl; R$_2$=diphenylmethyl)
63 (R$_1$=4-methylthiophenyl; R$_2$=3,4-dichlorobenzyl)
64 (R$_1$=3-methoxyphenyl; R$_2$=3-pyridylmethyl)
65 (R$_1$=4-methylthiophenyl; R$_2$=3-pyridylmethyl)
66 (R$_1$=3-trifluoromethylphenyl; R$_2$=2-phenylethyl)
67 (R$_1$=3-methoxyphenyl; R$_2$=2-phenylethyl)
68 (R$_1$=2,5-difluorophenyl; R$_2$=2-phenylethyl)
69 (R$_1$=3-methoxyphenyl; R$_2$=4-phenylbenzyl)
70 (R$_1$=3-methoxyphenyl; R$_2$=3,4-dichlorobenzyl)

Fig. 4

Activities of Compounds Depicted in Figure 4 Against µ- and κ-Opioid Receptors

| Compound | IC$_{50}$ in µ-Opioid Receptor Assay (µM) | IC$_{50}$ in κ-Opioid Receptor Assay (µM) |
|---|---|---|
| 51 | <10 | <10 |
| 52 | <1 | <10 |
| 53 | <1 | <10 |
| 54 | <1 | <10 |
| 55 | >10 | >10 |
| 56 | <10 | <10 |
| 57 | <10 | >10 |
| 58 | <10 | <10 |
| 59 | <1 | <10 |
| 60 | >10 | >10 |
| 61 | >10 | >10 |
| 62 | >10 | >10 |
| 63 | <10 | >10 |
| 64 | <10 | >10 |
| 65 | <1 | <10 |
| 66 | <1 | <10 |
| 67 | <1 | <10 |
| 68 | <1 | <10 |
| 69 | <10 | <10 |
| 70 | <10 | <10 |

Fig. 5

| Compound | IC$_{50}$ Against μ-Opioid Receptors (μM) | IC$_{50}$ Against κ-Opioid Receptors (μM) | IC$_{50}$ Against δ-Opioid Receptors (μM) |
|---|---|---|---|
| | <1 | <5 | >10 |
| | <1 | <5 | >10 |
| | <5 | <10 | >10 |
| | >10 | >10 | >10 |
| | <5 | <10 | >10 |

Fig. 6

| Compound | IC$_{50}$ Against μ-Opioid Receptors (μM) | IC$_{50}$ Against κ-Opioid Receptors (μM) | IC$_{50}$ Against δ-Opioid Receptors (μM) |
|---|---|---|---|
| (structure with OCH₃) | <5 | >10 | >10 |
| (structure with CF₃) | <5 | <10 | >10 |
| (structure with 2,5-difluoro) | <1 | <10 | >10 |
| (structure with OCH₃, diphenyl) | >10 | >10 | >10 |
| (structure with CF₃, diphenyl) | >10 | >10 | >10 |

Fig. 7

| Compoun | IC$_{50}$ Against μ-Opioid Receptors (μM) | IC$_{50}$ Against κ-Opioid Receptors (μM) | IC$_{50}$ Against δ-Opioid Receptors (μM) |
|---|---|---|---|
| (structure) | >10 | >10 | >10 |
| (structure) | <5 | >10 | >10 |
| (structure) | <5 | >10 | >10 |
| (structure) | <1 | <10 | >10 |
| (structure) | <1 | <5 | >10 |

Fig. 8

| Compound | IC$_{50}$ Against μ-Opioid Receptors (μM) | IC$_{50}$ Against κ-Opioid Receptors (μM) | IC$_{50}$ Against δ-Opioid Receptors (μM) |
|---|---|---|---|
| (structure) | <1 | <10 | >10 |
| (structure) | <5 | <10 | >10 |
| (structure) | <5 | <10 | >10 |
| (structure) | <1 | <5 | >10 |
| (structure) | <1 | <5 | >10 |

Fig. 9

| Compound | IC$_{50}$ Against μ-Opioid Receptors (μM) | IC$_{50}$ Against κ-Opioid Receptors (μM) | IC$_{50}$ Against δ-Opioid Receptors (μM) |
|---|---|---|---|
| 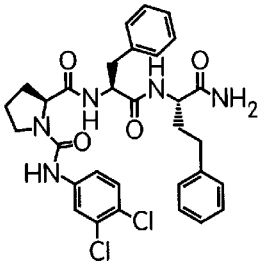 | <10 | <5 | >10 |
| 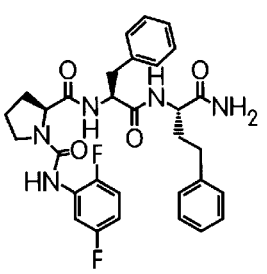 | <10 | <5 | >10 |
| 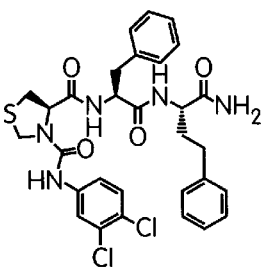 | >10 | <5 | >10 |
| 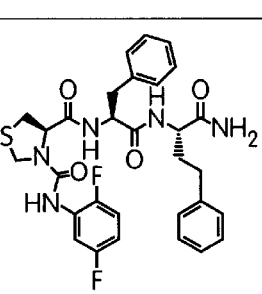 | >10 | >10 | >10 |
| 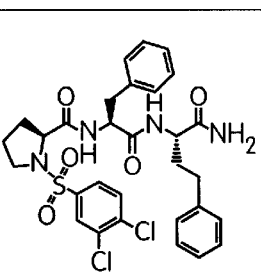 | >10 | <5 | >10 |
Fig. 10

| Compound | IC$_{50}$ Against μ-Opioid Receptors (μM) | IC$_{50}$ Against κ-Opioid Receptors (μM) | IC$_{50}$ Against δ-Opioid Receptors (μM) |
|---|---|---|---|
| *(structure)* | <10 | <10 | >10 |
| *(structure)* | <5 | >10 | >10 |
| *(structure)* | <5 | >10 | >10 |
| *(structure)* | <5 | <5 | >10 |
| *(structure)* | <5 | >10 | >10 |

Fig. 11

| Compound | IC$_{50}$ Against μ-Opioid Receptors (μM) | IC$_{50}$ Against κ-Opioid Receptors (μM) | IC$_{50}$ Against δ-Opioid Receptors (μM) |
|---|---|---|---|
| | <5 | >10 | >10 |
| | <5 | >10 | >10 |
| | >10 | <10 | >10 |
| | <5 | >10 | >10 |
| | >10 | >10 | >10 |

Fig. 12

| Compound | IC$_{50}$ Against μ-Opioid Receptors (μM) | IC$_{50}$ Against κ-Opioid Receptors (μM) | IC$_{50}$ Against δ-Opioid Receptors (μM) |
|---|---|---|---|
| 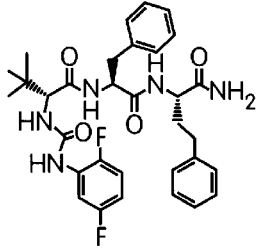 | >10 | >10 | >10 |
| 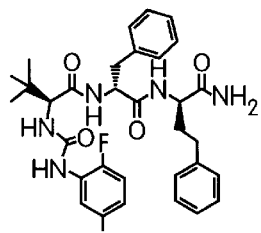 | <5 | >10 | >10 |
| 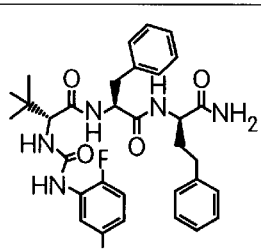 | <10 | >10 | >10 |
| 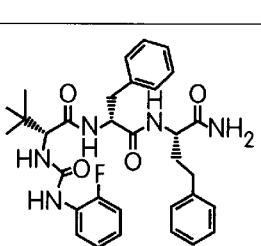 | >10 | >10 | >10 |
| 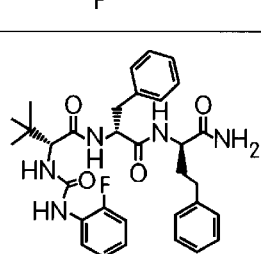 | >10 | >10 | >10 |
Fig. 13

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| (structure with 3,4-dichlorobenzyl, t-Bu, Phe, Phe-NH2) | <10 | <10 | <10 |
| (structure with 3-CF3-benzyl, t-Bu, Phe, homoPhe-NH2) | <10 | <10 | <10 |
| (structure with 2,5-difluorobenzyl, t-Bu, Phe, homoPhe-NH2) | <10 | <25 | <10 |
| (structure with 3-OCH3-benzyl, t-Bu, Phe, homoPhe-NH2) | <10 | <25 | <10 |
| (structure with 3,4-dichlorobenzyl-proline, Phe, homoPhe-NH2) | <10 | <50 | <25 |

Fig. 14

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| | <25 | <50 | <10 |
| | <10 | <50 | <10 |
| | <10 | <50 | <10 |
| | <10 | <25 | <10 |
| | <10 | <25 | <25 |

Fig. 15

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| 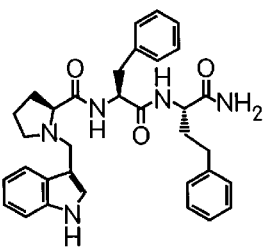 | <25 | <50 | <25 |
| 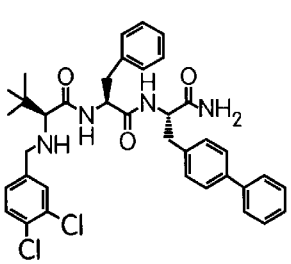 | <10 | <25 | <25 |
| 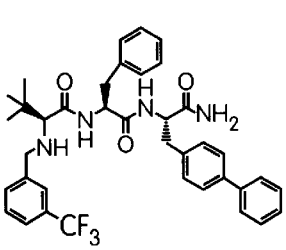 | <10 | <25 | <50 |
| 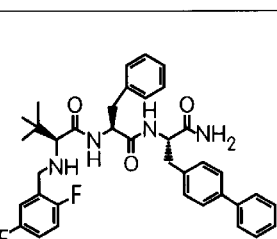 | <10 | <10 | <10 |
Fig. 16

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| 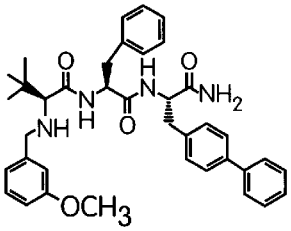 | <10 | <25 | <10 |
| 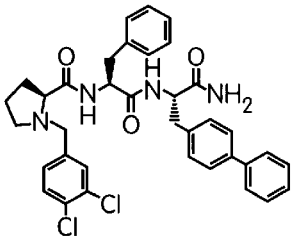 | <10 | <25 | <10 |
|  | <10 | <25 | <10 |
| 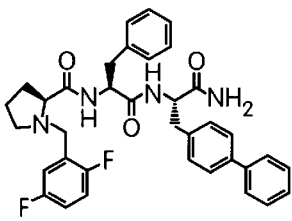 | <10 | <10 | <25 |
| 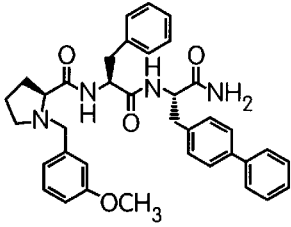 | <25 | <25 | <25 |
Fig. 17

| Compound | Percent Inhibition of µ-Opioid Receptors at 1µM | Percent Inhibition of κ-Opioid Receptors at 1µM | Percent Inhibition of δ-Opioid Receptors at 1µM |
|---|---|---|---|
| *(structure)* | <10 | <25 | <10 |
| *(structure)* | <10 | <10 | <10 |
| *(structure)* | <25 | <50 | <10 |
| *(structure)* | <25 | <10 | <10 |
| *(structure)* | <10 | <10 | <25 |

Fig. 18

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| (structure with CF₃) | <25 | <25 | <10 |
| (structure with 2,5-F₂) | <25 | <25 | <10 |
| (structure with OCH₃) | <10 | <10 | <10 |
| (structure with 3,4-Cl₂) | <25 | <25 | <10 |
| (structure with CF₃) | <10 | <50 | <10 |

Fig. 19

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| | <10 | <25 | <10 |
| | <25 | <10 | <10 |
| | <10 | <50 | <10 |
| | <10 | <25 | <25 |
| | <25 | <50 | <25 |

Fig. 20

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| (structure) | <25 | <25 | <10 |
| (structure) | <10 | <10 | <10 |
| (structure) | <10 | <10 | <10 |
| (structure) | <10 | <10 | <10 |
| (structure) | <25 | <10 | <10 |

Fig. 21

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| (structure with 3,4-dichlorobenzyl) | <25 | <25 | <10 |
| (structure with 3-CF₃ benzyl) | <10 | <10 | <10 |
| (structure with 2,5-difluorobenzyl) | <10 | <25 | <10 |
| (structure with 3-OCH₃ benzyl) | <10 | <25 | <10 |
| (structure with imidazole/tBu) | <25 | <25 | <10 |

Fig. 22

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| | <10 | <10 | <10 |
| | <25 | <25 | <10 |
| | <10 | <25 | <10 |
| | >50 | >50 | <10 |
| | >50 | >50 | <25 |

Fig. 23

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| 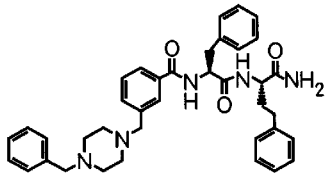 | <50 | <50 | <25 |
| 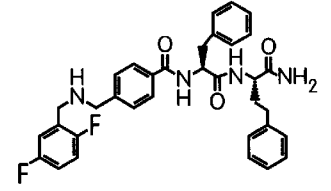 | <50 | <50 | <25 |
| 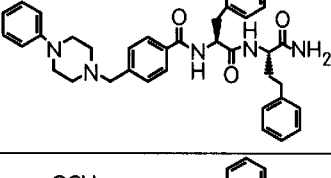 | <50 | <50 | <25 |
| 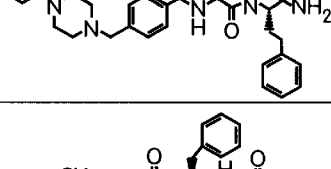 | <50 | <50 | <50 |
| 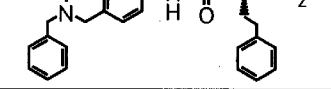 | >50 | >50 | <25 |
Fig. 24

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| 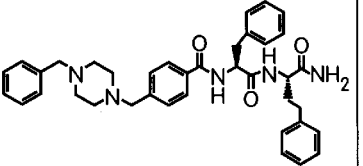 | <50 | <50 | <10 |
| 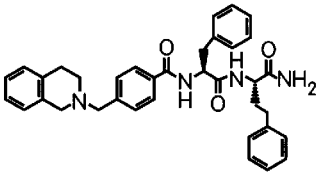 | >50 | >50 | <10 |
| 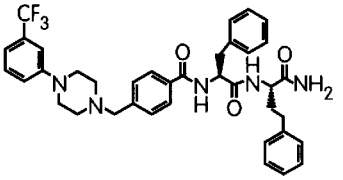 | <50 | <50 | <10 |
| 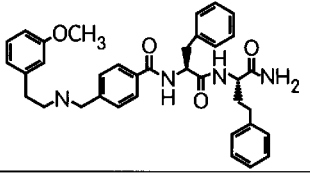 | >50 | >50 | >50 |
| 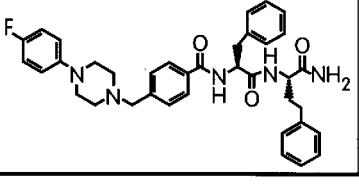 | <50 | <50 | <10 |
Fig. 25

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| [structure with OH-phenyl] | >50 | >50 | >50 |
| [structure with phenylpropyl] | >50 | <50 | >50 |
| [structure with difluorobenzyl, biphenyl] | <50 | >50 | <25 |
| [structure with N-methylpiperazine, biphenyl] | >50 | >50 | <50 |
| [structure with N-phenylpiperazine, biphenyl] | <50 | <25 | <10 |

Fig. 26

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| [structure with OCH₃] | <50 | <10 | <10 |
| [structure with CH₃/benzyl] | <50 | <50 | <25 |
| [structure with benzyl piperazine] | <25 | <25 | <25 |
| [structure with tetrahydroisoquinoline] | <25 | <50 | <10 |
| [structure with CF₃] | <25 | <25 | <10 |

Fig. 27

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| 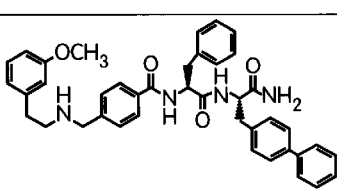 | <50 | <50 | <50 |
| 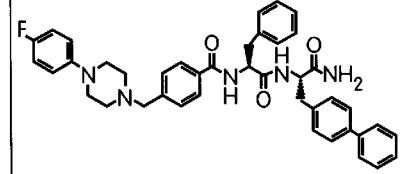 | <50 | <50 | <10 |
| 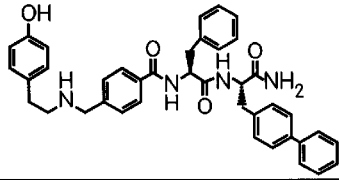 | >50 | >50 | >50 |
| 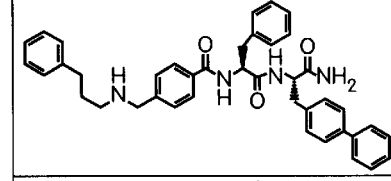 | >50 | <50 | <25 |
| 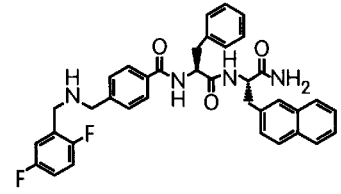 | <50 | <50 | <10 |
Fig. 28

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
|  | <50 | <50 | <25 |
|  | <50 | <25 | <10 |
|  | <50 | <25 | <10 |
|  | <50 | <25 | <10 |
|  | <50 | <25 | <25 |

Fig. 29

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| 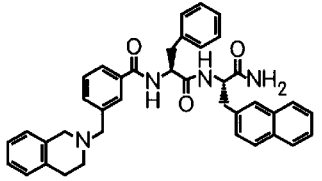 | >50 | >50 | <10 |
| 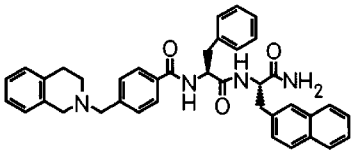 | >50 | <50 | <10 |
|  | <50 | <25 | <10 |
| 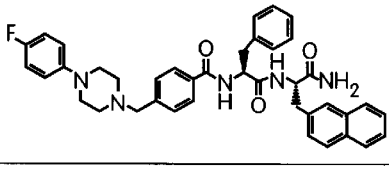 | <50 | <25 | <10 |
| 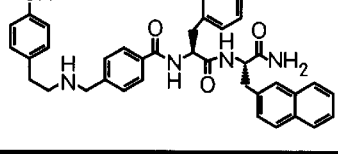 | >50 | >50 | >50 |
Fig. 30

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| | >50 | <50 | <50 |
| | >50 | >50 | <10 |
| | >50 | >50 | <10 |
| | <25 | <25 | <10 |
| | <50 | <50 | <25 |

Fig. 31

| Compound | Percent Inhibition of μ-Opioid Receptors at 1μM | Percent Inhibition of κ-Opioid Receptors at 1μM | Percent Inhibition of δ-Opioid Receptors at 1μM |
|---|---|---|---|
| 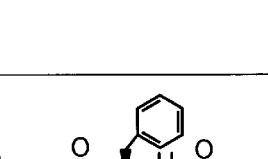 | <50 | <25 | <10 |
| 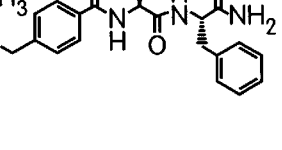 | >50 | <25 | <10 |
Fig. 32

Results of Agonist and Antagonist Functional Assays of μ-Opioid Receptors Using Field-Stimulated Guinea Pig Ileum (% Activity vs. Control)

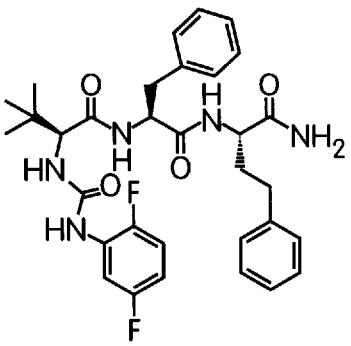 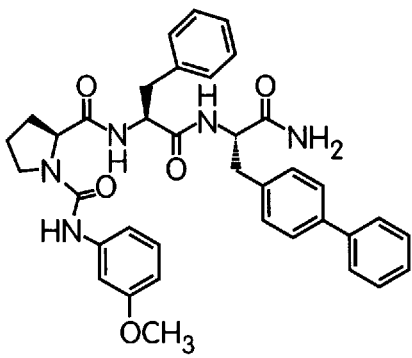

IC$_{50}$ Values
μ < 1 μM
κ < 5 μM
δ > 10 μM

IC$_{50}$ Values
μ < 1 μM
κ < 5 μM
δ > 10 μM

μ-Agonism vs. DAMGO
ED$_{50}$ < 1 μM

μ-Agonism vs. DAMGO
ED$_{50}$ > 30 μM

μ-Antagonism vs. Cyprodine
ED$_{50}$ > 30 μM

μ-Antagonism vs. Cyprodine
ED$_{50}$ < 3 μM

Controls for Functional Assays with μ-Receptors
DAMGO Agonism: 100% @ 0.03 μM
Cyprodine Antagonism: 68% @ 0.05 μM

Fig. 33

Results of Agonist and Antagonist Functional Assays of μ-Opioid Receptors Using Field-Stimulated Guinea Pig Ileum (% Activity vs. Control)

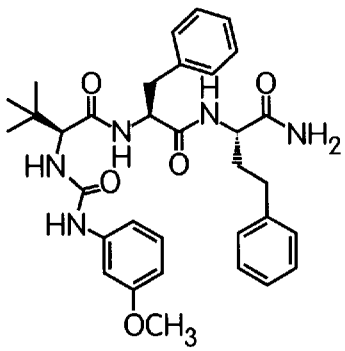 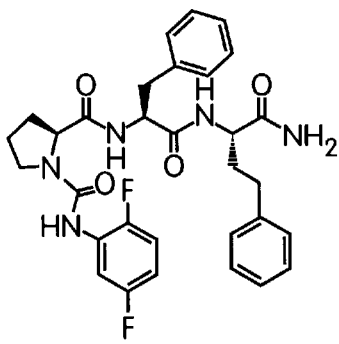

$IC_{50}$ Values
μ < 1 μM
κ < 10 μM
δ > 10 μM

$IC_{50}$ Values
μ < 10 μM
κ < 5 μM
δ > 10 μM

μ-Agonism vs. DAMGO
$ED_{50}$ > 30 μM

μ-Agonism vs. DAMGO
$ED_{50}$ > 30 μM

μ-Antagonism vs. Cyprodine
$ED_{50}$ > 30 μM

μ-Antagonism vs. Cyprodine
$ED_{50}$ > 30 μM

Controls for Functional Assays with μ-Receptors
DAMGO Agonism: 100% @ 0.03 μM
Cyprodine Antagonism: 68% @ 0.05 μM

Fig. 34

Syntheses of Endomorphin Analogues Comprising an Aminobenzamide Linker
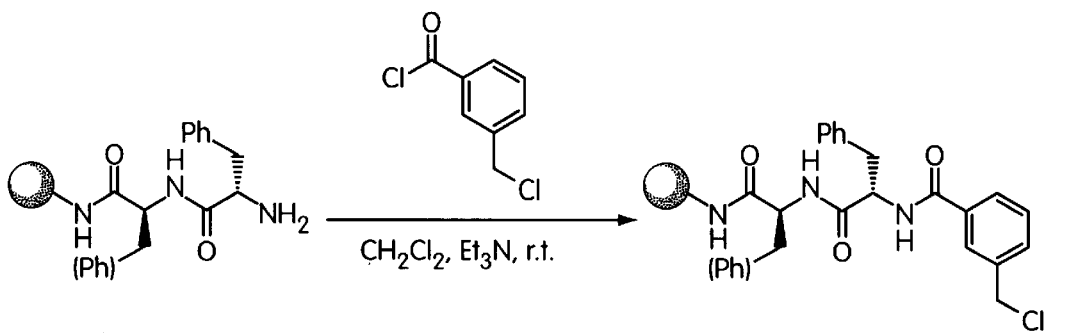
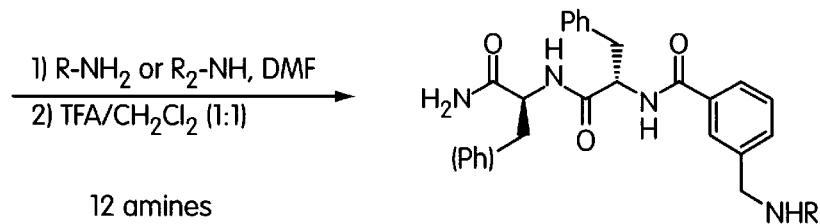
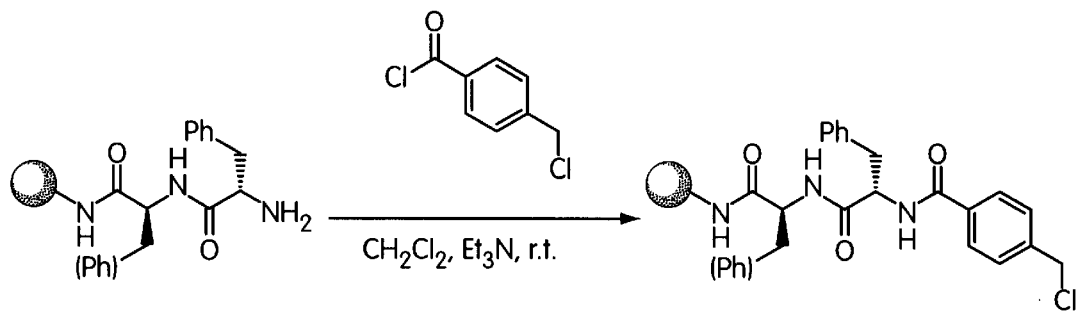
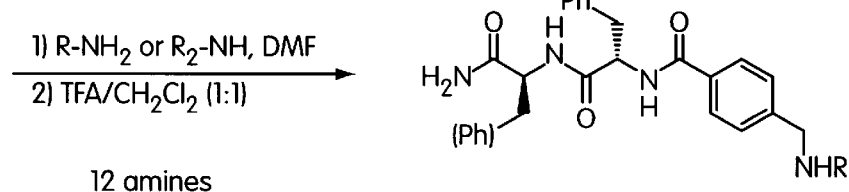
Fig. 35

Early and Intermediate Steps in the Synthesis of Endomorphin Analogues Comprising Amine Functionality
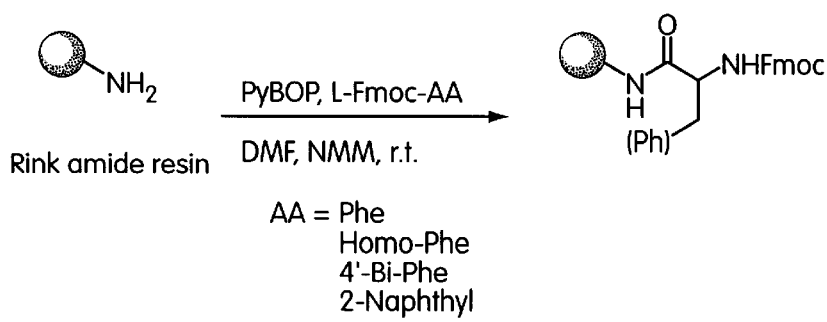
AA = Phe
Homo-Phe
4'-Bi-Phe
2-Naphthyl
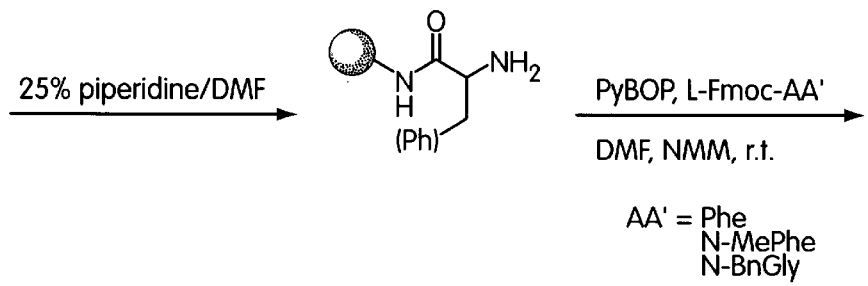
AA' = Phe
N-MePhe
N-BnGly
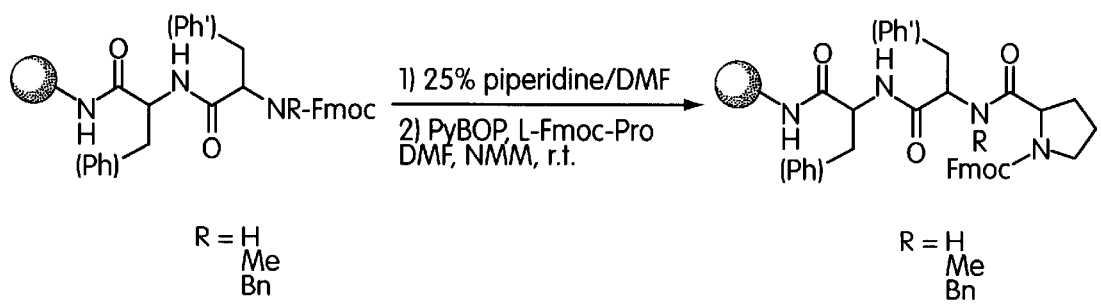
R = H
Me
Bn
R = H
Me
Bn
Fig. 38

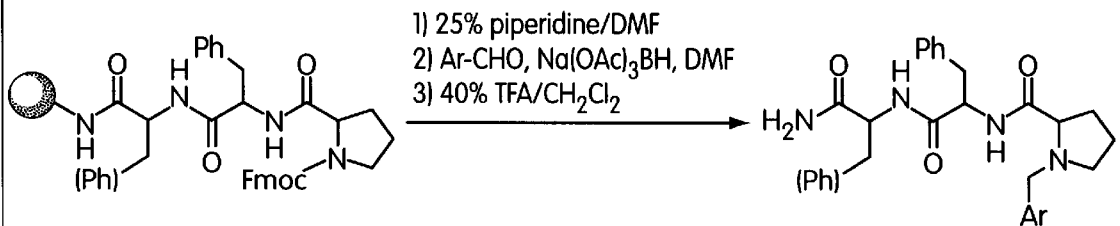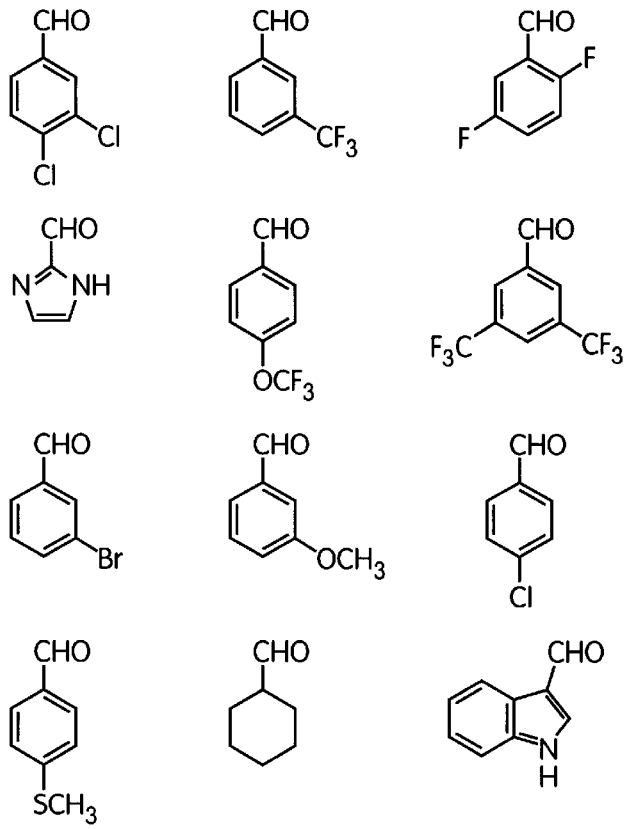
Fig. 39

LIGANDS FOR OPIOID RECEPTORS

RELATED APPLICATIONS

This application claims priority to U.S. Provisional Patent Application No. 60/089,792, filed Jun. 18, 1998.

BACKGROUND OF THE INVENTION

Millions of people suffer from chronic or intractable pain. Persistent pain varies in etiology and presentation. In some cases, symptoms and signs may be evident within a few weeks to a few months after the occurrence of an injury or the onset of disease, e.g. cancer or AIDS. Like many illnesses that at one time were not well understood, pain and its many manifestations may be poorly treated and seriously underestimated. Inappropriately treated pain seriously compromises the patient's quality of life, causing emotional suffering and increasing the risk of lost livelihood and disrupted social integration. Severe chronic pain affects both the pediatric and adult population, and often leads to mood disorders, including depression and, in rare cases, suicide.

In the last several years, health policy-makers, health professionals, regulators, and the public have become increasingly interested in the provision of better pain therapies. This interest is evidenced, in part, by the U.S. Department of Health and Human Services' dissemination of Clinical Practice Guidelines for the management of acute pain and cancer pain. These publications state that opioids are an essential part of a pain management plan. There is currently no nationally accepted consensus for the treatment of chronic pain not due to cancer, yet the economic and social costs of chronic pain are substantial, with estimates ranging in the tens of billions of dollars annually.

Opioids are the major class of analgesics used in the management of moderate to severe pain because of their effectiveness, ease of titration, and favorable risk-to-benefit ratio. Opioids produce analgesia by binding to specific receptors both within and outside the CNS. Opioid analgesics are classified as full agonists, partial agonists, or mixed agonist-antagonists, depending on the specific receptors to which they bind and their intrinsic activity at that receptor.

Three subclasses of opioid receptor have been identified in humans, namely the $\delta$-, $\kappa$-, and $\mu$-opioid receptors. Analgesia is thought to involve activation of both $\mu$ and $\kappa$ receptors. Notwithstanding their low selectivity for $\mu$ over $\kappa$ receptors, it is likely that morphine and morphine-like opioid agonists produce analgesia primarily through interaction with $\mu$ receptors; selective agonists of $\kappa$ receptors in humans produce analgesia, but rather than the euphoria associated with morphine and congeners, these compounds produce dysphoria and psychotomimetic effects. The consequences of activating $\delta$ receptors in humans remain unclear.

Commonly used full agonists include morphine, hydromorphone, meperidine, methadone, levorphanol, and fentanyl. These opioids are classified as full agonists because there is not a ceiling to their analgesic efficacy, nor will they reverse or antagonize the effects of other opioids within this class when given simultaneously. Side effects include constipation, nausea, urinary retention, confusion, sedation, and respiratory depression. Morphine is the most commonly used opioid for moderate to severe pain because of its availability in a wide variety of dosage forms, its well-characterized pharmacokinetics and pharmacodynamics, and its relatively low cost. Meperidine may be useful for brief courses (e.g., a few days) to treat acute pain and to manage rigors (shivering) induced by medication, but it generally should be avoided in patients with cancer because of its short duration of action (2.5 to 3.5 hours) and its toxic metabolite, normeperidine. This metabolite accumulates, particularly when renal function is impaired, and causes CNS stimulation, which may lead to dysphoria, agitation, and seizures; meperidine, therefore, should not be used if continued opioid use is anticipated.

Buprenorphine is an example of a partial agonist. Buprenorphine has a relatively low intrinsic efficacy at the opioid receptor in comparison to full opioid agonists, and it displays a ceiling effect to analgesia. Clinical studies found buprenorphine to be effective in the treatment of heroin addiction and to have some advantages over methadone in terms of relative safety. Buprenorphine also reduces cocaine abuse in individuals who are dependent on both heroin and cocaine. The dual effects of buprenorphine provide new insight into the mechanisms of cocaine and heroin dependence; these observations suggest, furthermore, that the underlying mechanisms of these dependencies may be similar.

Mixed agonist-antagonists in clinical use include pentazocine, butorphanol tartrate, and nalbuphine hydrochloride. These drugs have an analgesic ceiling. In contrast to full agonists, these drugs block opioid analgesia at one type of opioid receptor ($\mu$) or are neutral at the $\mu$ receptor while simultaneously activating a different opioid receptor ($\kappa$). Patients receiving full opioid agonists should not be given a mixed agonist-antagonist because doing so may precipitate a withdrawal syndrome and increase pain.

The development of physical dependence with repeated use is a characteristic feature of the opioid drugs, and the possibility of developing drug dependence is one of the major limitations of their clinical use. Almost all opioid users rapidly develop drug dependency which can lead to apathy, weight loss, loss of sex drive, anxiety, insomnia, and drug cravings.

Historically, the development of analgesic tolerance was believed to limit the ability to use opioids efficaciously on a long-term basis for pain management. Tolerance, or decreasing pain relief with the same dosage over time, has not proven to be a prevalent limitation to long-term opioid use. Experience with treating cancer pain has shown that what initially appears to be tolerance is usually progression of the disease. Furthermore, for most opioids, there does not appear to be an arbitrary upper dosage limit, as was once thought.

Cessation of opioid administration may result in withdrawal. Symptoms of withdrawal are often the opposite of the effects achieved by the drug; withdrawal from morphine, however, results in complex symptoms that may seem unrelated to its effects. Misunderstanding of addiction and mislabeling of patients as addicts result in unnecessary withholding of opioid medications. Addiction is a compulsive disorder in which an individual becomes preoccupied with obtaining and using a substance, the continued use of which results in a decreased quality of life. Studies indicate that the de novo development of addiction is low when opioids are used for the relief of pain. Furthermore, even opioid addicts can benefit from the carefully supervised, judicious use of opioids for the treatment of pain due to cancer, surgery, or recurrent painful illnesses such as sickle cell disease.

Zadina et al. recently reported the isolation and characterization of endomorphins 1 (1) and 2 (2) (Nature 1997, 386, 499–502). The endomorphins are tetrapeptides, isolated from bovine frontal cortex, that selectively bind in vitro to the μ-opioid receptor; 1 (Seq. ID No.1) and 2 (Seq. ID No.2) select for μ over δ receptors by factors of 4,183 and 13,381, respectively; and 1 (Seq. ID No.1) and 2 (Seq. ID No.2) select for μ over κ receptors by factors of 15,077 and 7,594, respectively. Additionally, 1 (Seq. ID No.1) and 2 (Seq. I.D. No.2) are potent analgesics in vivo; intracerebroventricular injections to mice of 1 (Seq. ID No.1) and 2 (Seq. ID No.2) established $ED_{50}$ values of 8.4 μg and 2.9 μg, respectively. Finally, the analgesic effects of the endomorphins were antagonized by naloxone and β-funaltrexamine.

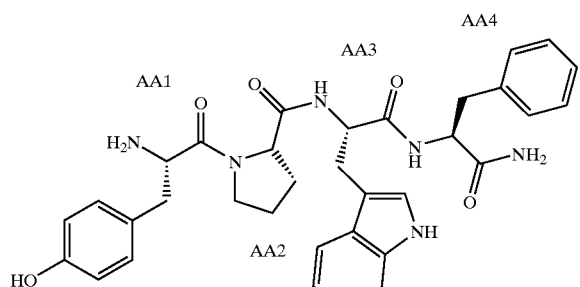

Endomorphin 1(1) [Tyr-Pro-Trp-Phe-NH$_2$] (Seq ID No. 1)

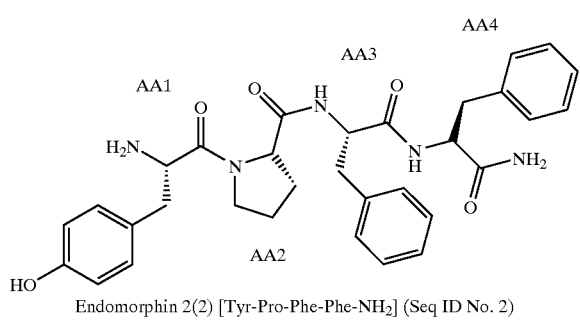

Endomorphin 2(2) [Tyr-Pro-Phe-Phe-NH$_2$] (Seq ID No. 2)

Oligopeptides do not easily cross the GI/blood and blood/brain barriers. This problem cannot be attributed solely to a lack of metabolic stability. Crossing both the GI/blood and blood/brain barriers are key steps when considering using a peptide as a drug. While several peptides have been successfully stabilized against degradation, their bioavailability, namely their ability to cross the blood/brain barrier remained problematic.

In particular, neuropeptides, e.g. the endomorphins, undergo fast proteolytic degradation in the gastrointestinal tract, in blood and in other tissues. The pharmacokinetics of neuropeptides in the synapse are distinct from those of a peptide elsewhere. In the synapse, the time required for the neuropeptides to accomplish their function is very short in part due to the short distances involved. The endogenous proteases which are responsible for terminating the activity of a given neuropeptide are the only ones present in the vicinity, and they degrade the peptide immediately after completion of its function. In order to devise a therapeutic peptide for this setting, its structure should be stabilized against the synaptic proteases responsible for its degradation, as well as against other proteases present in the GI tract, blood and other tissues.

Moreover, biologically active oligopeptides exist in solution as a mixture of rapidly interconverting conformers (Kessler, H., Angew. Chem., Int. Ed. Eng., 21, 512 (1982); this fact may lead to a lack of receptor selectivity and unanticipated susceptibility to proteolysis (Veber, D. F. and Freidinger, R. M., Trends in Neurosci. 8, 392 (1985). Furthermore, the numerous conformational equilibria can obscure the identities of the biologically active conformers of the oligopeptide. Structural modifications of an oligopeptide that reduce the conformational space available to it have the potential to mitigate side-effects, and/or its degradation, by eliminating the conformations responsible for the side-effects, and/or those required by the degradation enzymes, respectively. These characteristics of naturally occurring peptides, e.g. neuropeptides, are of great significance and constitute major challenges in applying the peptide as a drug, as well as understanding the pharmacological and molecular interaction between the peptide and its receptor. For example, analgesic peptidomimetic opiates, which are "imitations" of endogenous enkephalins, were developed through research which was more random than rational and did not take into consideration all the factors described above.

In many cases, the peptidomimetics that result from a peptide structural lead using the "rational" approach comprise unnatural α-amino acids. Recently, fundamental research on the use of norpeptidic scaffolds, such as steroidal or sugar structures, to anchor specific receptor-binding groups in fixed geometric relationships have been described (see for example Hirschmann, R. et al., 1992 J. Am. Chem. Soc., 114:9699–9701; and Hirschmann, R. et al., 1992 J. Am. Chem. Soc., 114:9217–9218).

SUMMARY OF THE INVENTION

There exists a need to provide alternative and improved agents for the treatment of pain, particularly for the treatment of chronic pain, e.g. pain associated with cancer and AIDS. Opioids, specifically ligands for the μ-opioid receptor, are the major class of analgesics used in the management of moderate to severe pain because of their effectiveness, ease of titration, and favorable risk-to-benefit ratio. Unfortunately, the opioids currently available are addictive to varying degrees. Research into the development of new, selective ligands for opioid receptors holds the promise of yielding potent analgesics that lack the addictive characteristics of morphine and its congeners.

The present invention is directed to the use of organic molecules—e.g. tetrapeptides, derivatives and analogs thereof, and the respective pharmaceutical formulations thereof—in the treatment of chronic pain. Specifically proposed as analgesic agents are compounds, and pharmaceutical formulations thereof, based on endomorphin 1 (1) (Tyr-Pro-Trp-Phe-NH$_2$)(Seq. ID No.1), endomorphin 2 (2) (Tyr-Pro-Phe-Phe-NH$_2$)(Seq. ID No.2), and analogs and derivatives thereof (for the disclosure of the endomorphins, see: Zadina et al. Nature 1997, 386, 499–502). The wide range of novel analgesic compounds disclosed herein enables the potential to tailor potency, specificity, solubility, bioavailability, stability, toxicity, and other physical properties to suit specific purposes.

BRIEF DESCRIPTION OF THE FIGURES

FIG. 4 depicts the structures of twenty endomorphin analogues of the present invention.

FIG. 5 consists of a table of the activities ($IC_{50}$s) against $\mu$- and $\kappa$-opioid receptors of the twenty endomorphnin analogues depicted in FIG. 4.

FIG. 6 consists of a table of the structures and activities ($IC_{50}$s) against $\mu$- and $\kappa$- and $\delta$-opioid receptors of five endomorphin analogues of the present invention.

FIG. 7 consists of a table of the structures and activities ($IC_{50}$s) against $\mu$- and $\kappa$- and $\delta$-opioid receptors of five endomorphin analogues of the present invention.

FIG. 8 consists of a table of the structures and activities ($IC_{50}$s) against $\mu$- and $\kappa$- and $\delta$-opioid receptors of five endomorphin analogues of the present invention.

FIG. 9 consists of a table of the structures and activities ($IC_{50}$s) against $\mu$- and $\kappa$- and $\delta$-opioid receptors of five endomorphin analogues of the present invention.

FIG. 10 consists of a table of the structures and activities ($IC_{50}$s) against $\mu$- and $\kappa$- and $\delta$-opioid receptors of five endomorphin analogues of the present invention.

FIG. 11 consists of a table of the structures and activities ($IC_{50}$s) against $\mu$- and $\kappa$- and $\delta$-opioid receptors of five endomorphin analogues of the present invention.

FIG. 12 consists of a table of the structures and activities ($IC_{50}$s) against $\mu$- and $\kappa$- and $\delta$-opioid receptors of five endomorphin analogues of the present invention.

FIG. 13 consists of a table of the structures and activities ($IC_{50}$s) against $\mu$- and $\kappa$- and $\delta$-opioid receptors of five endomorphin analogues of the present invention.

FIG. 14 consists of a table of the structures of five endomorphin analogues of the present invention and their percent inhibition at 1 $\mu$M of $\mu$- and $\kappa$- and $\delta$-opioid receptors.

FIG. 15 consists of a table of the structures of five endomorphin analogues of the present invention and their percent inhibition at 1 $\mu$M of $\mu$- and $\kappa$- and $\delta$-opioid receptors.

FIG. 16 consists of a table of the structures of five endomorphin analogues of the present invention and their percent inhibition at 1 $\mu$M of $\mu$- and $\kappa$- and $\delta$-opioid receptors.

FIG. 17 consists of a table of the structures of five endomorphin analogues of the present invention and their percent inhibition at 1 $\mu$M of $\mu$- and $\kappa$- and $\delta$-opioid receptors.

FIG. 18 consists of a table of the structures of five endomorphin analogues of the present invention and their percent inhibition at 1 $\mu$M of $\mu$- and $\kappa$- and $\delta$-opioid receptors.

FIG. 19 consists of a table of the structures of five endomorphin analogues of the present invention and their percent inhibition at 1 $\mu$M of $\mu$- and $\kappa$- and $\delta$-opioid receptors.

FIG. 20 consists of a table of the structures of five endomorphin analogues of the present invention and their percent inhibition at 1 $\mu$M of $\mu$- and $\kappa$- and $\delta$-opioid receptors.

FIG. 21 consists of a table of the structures of five endomorphin analogues of the present invention and their percent inhibition at 1 $\mu$M of $\mu$- and $\kappa$- and $\delta$-opioid receptors.

FIG. 22 consists of a table of the structures of five endomorphin analogues of the present invention and their percent inhibition at 1 $\mu$M of $\mu$- and $\kappa$- and $\delta$-opioid receptors.

FIG. 23 consists of a table of the structures of five endomorphin analogues of the present invention and their percent inhibition at 1 $\mu$M of $\mu$- and $\kappa$- and $\delta$-opioid receptors.

FIG. 24 consists of a table of the structures of five endomorphin analogues of the present invention and their percent inhibition at 1 $\mu$M of $\mu$- and $\kappa$- and $\delta$-opioid receptors.

FIG. 25 consists of a table of the structures of five endomorphin analogues of the present invention and their percent inhibition at 1 $\mu$M of $\mu$- and $\kappa$- and $\delta$-opioid receptors.

FIG. 26 consists of a table of the structures of five endomorphin analogues of the present invention and their percent inhibition at 1 $\mu$M of $\mu$- and $\kappa$- and $\delta$-opioid receptors.

FIG. 27 consists of a table of the structures of five endomorphin analogues of the present invention and their percent inhibition at 1 $\mu$M of $\mu$- and $\kappa$- and $\delta$-opioid receptors.

FIG. 28 consists of a table of the structures of five endomorphin analogues of the present invention and their percent inhibition at 1 $\mu$M of $\mu$- and $\kappa$- and $\delta$-opioid receptors.

FIG. 29 consists of a table of the structures of five endomorphin analogues of the present invention and their percent inhibition at 1 $\mu$M of $\mu$- and $\kappa$- and $\delta$-opioid receptors.

FIG. 30 consists of a table of the structures of five endomorphin analogues of the present invention and their percent inhibition at 1 $\mu$M of $\mu$- and $\kappa$- and $\delta$-opioid receptors.

FIG. 31 consists of a table of the structures of five endomorphin analogues of the present invention and their percent inhibition at 1 $\mu$M of $\mu$- and $\kappa$- and $\delta$-opioid receptors.

FIG. 32 consists of a table of the structures of two endomorphin analogues of the present invention and their percent inhibition at 1 $\mu$M of $\mu$- and $\kappa$- and $\delta$-opioid receptors.

FIG. 33 depicts the results of agonist and antagonist functional assays of two endomorphin analogues against $\mu$-opioid receptors.

FIG. 34 depicts the results of agonist and antagonist functional assays of two endomorphin analogues against $\mu$-opioid receptors.

FIG. 35 depicts a synthetic strategy utilized to prepare endomorphin analogues comprising an aminobenzamide linker.

FIG. 38 depicts the early and intermediate steps in a synthetic strategy utilized to prepare endomorphin analogues comprising an amine functional group.

FIG. 39 depicts the final steps in a synthetic strategy utilized to prepare endomorphin analogues comprising an amine functional group.

DETAILED DESCRIPTION OF THE INVENTION

Figure 1:
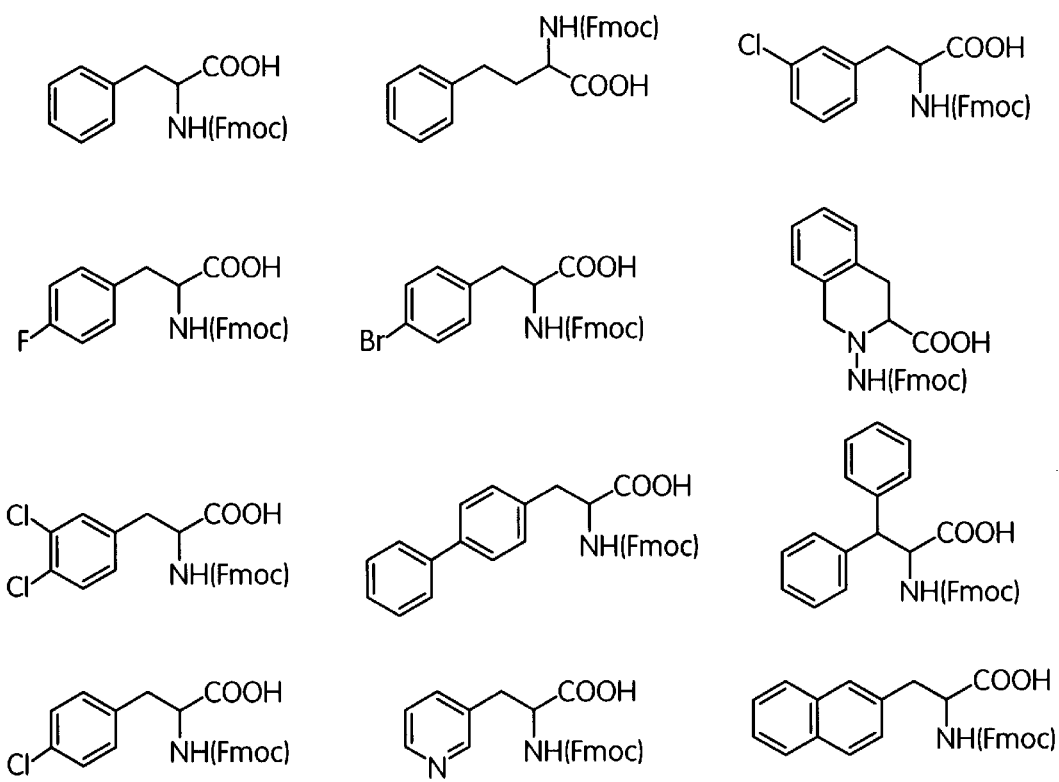
FIG. 1 depicts attachment to the solid support of the first amino acid residue of certain endomorphin analogues, including the structures of twelve amino acids used in this step.
Figure 2:
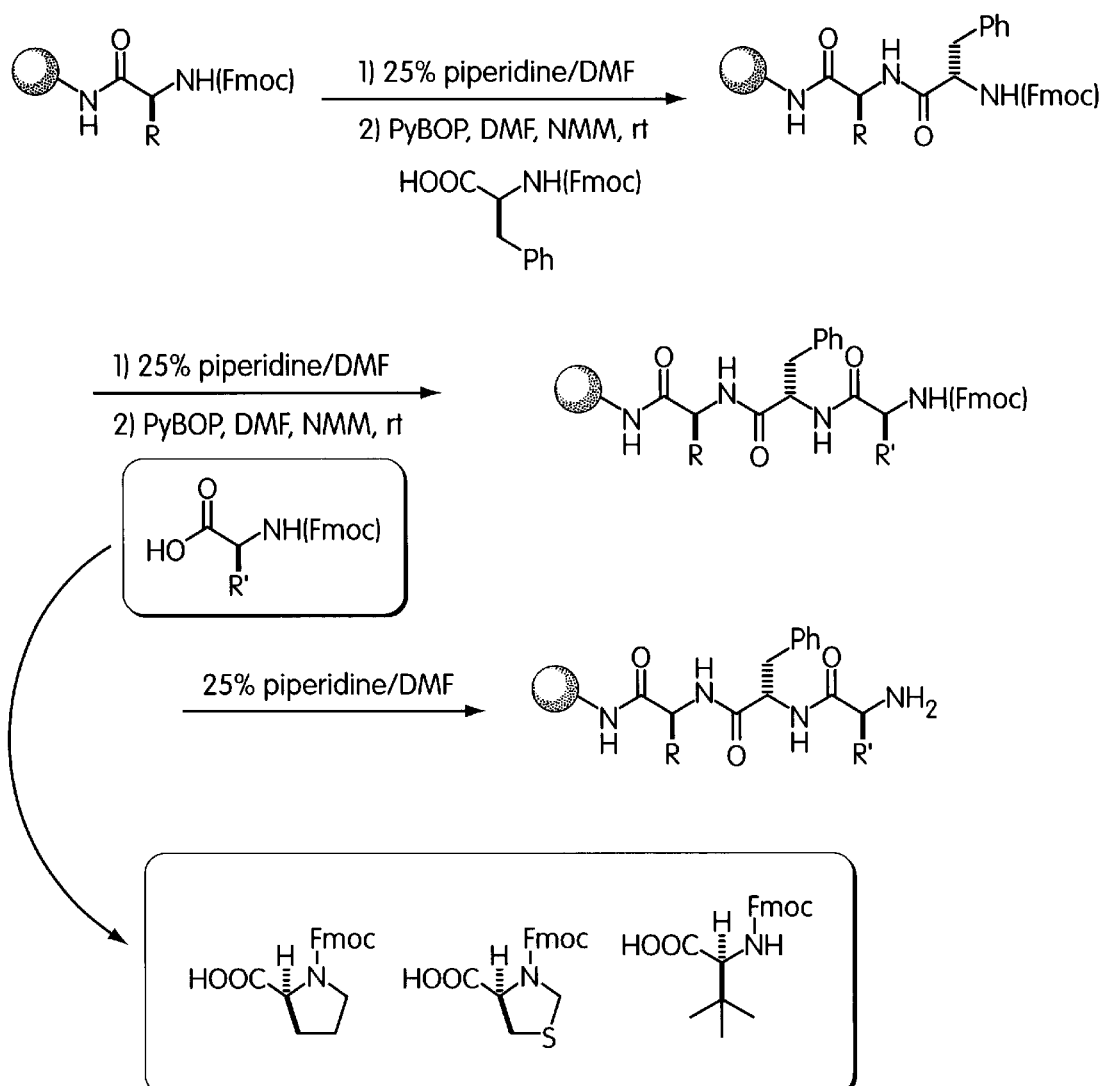
FIG. 2 depicts attachment of the second and third amino acid residues to the solid-bound first amino acid residue of certain endomorphin analogues, including the structures of three amino acids used as the third residue of the analogues (the second residue is Phe in each of these structures).
Figure 3:
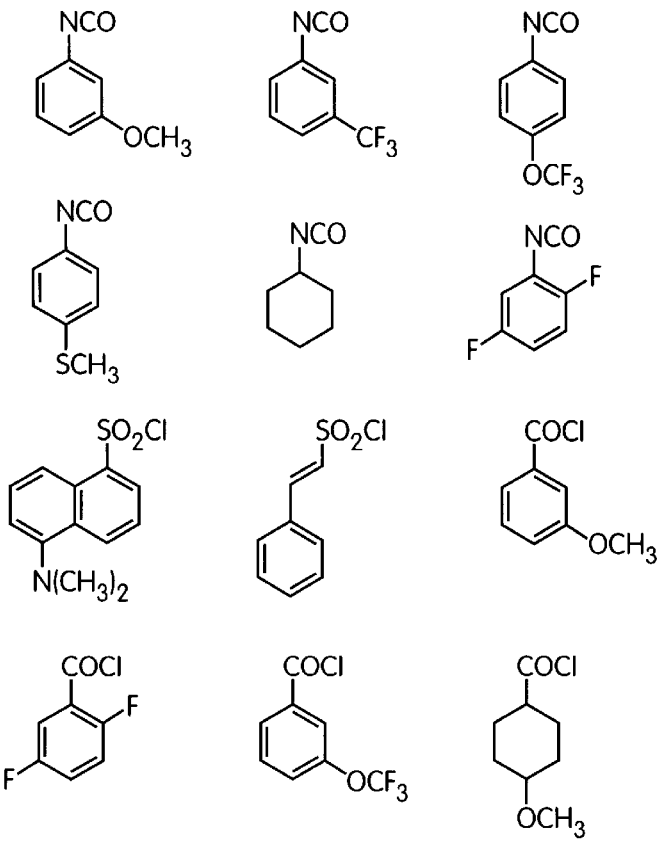
FIG. 3 depicts attachment of a group serving as a surrogate for the fourth amino acid residue of an endomorphin to the aforementioned solid-bound tripeptide of certain endomorphin analogues, including the structures of six isocyanates, two sulphonyl chlorides, and four acid chlorides used in this step.
Figure 36:
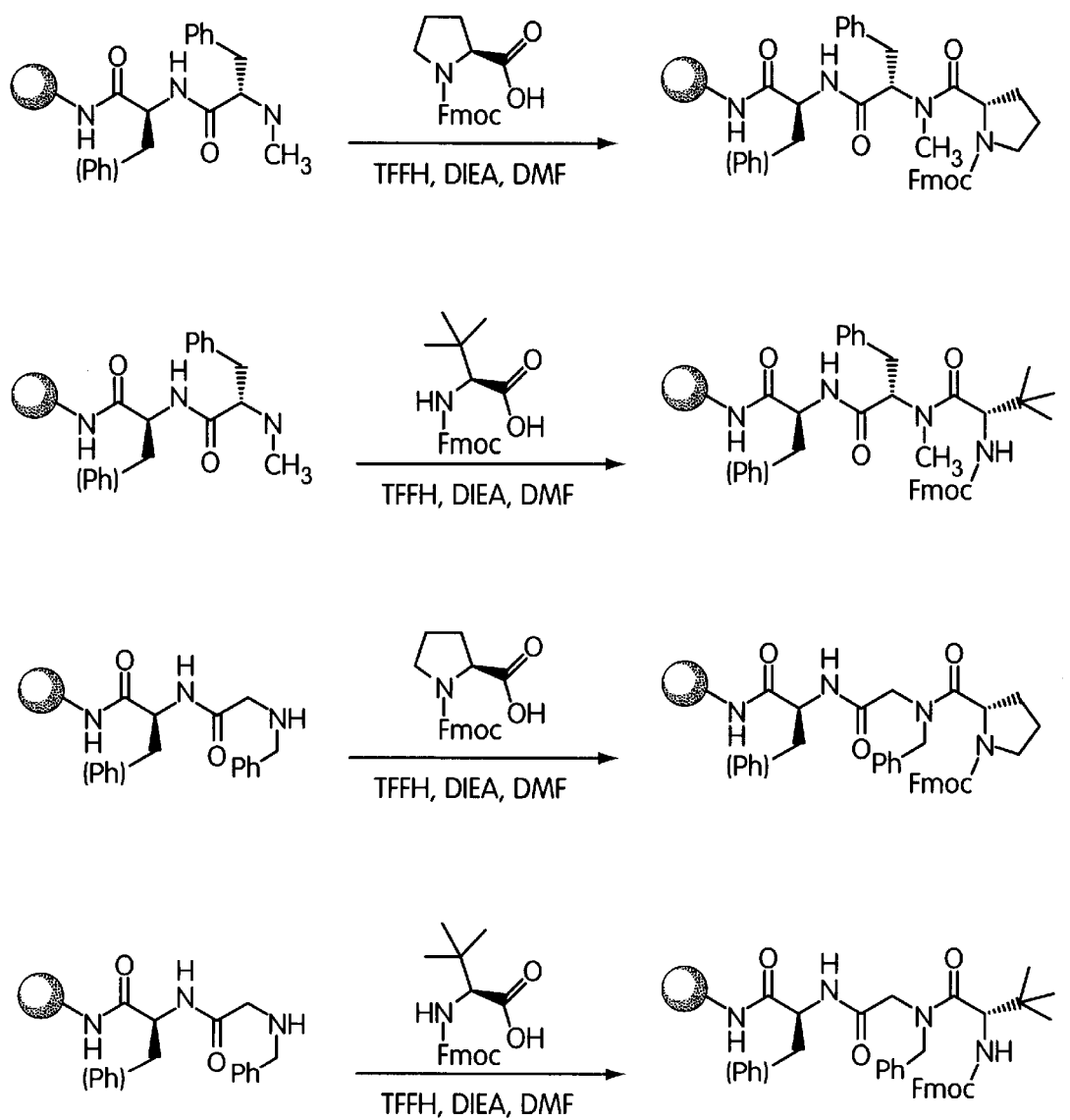
FIG. 36 depicts the intermediate steps in a synthetic strategy utilized to prepare endomorphin analogues comprising an N-alkylamide functional group.
Figure 37:
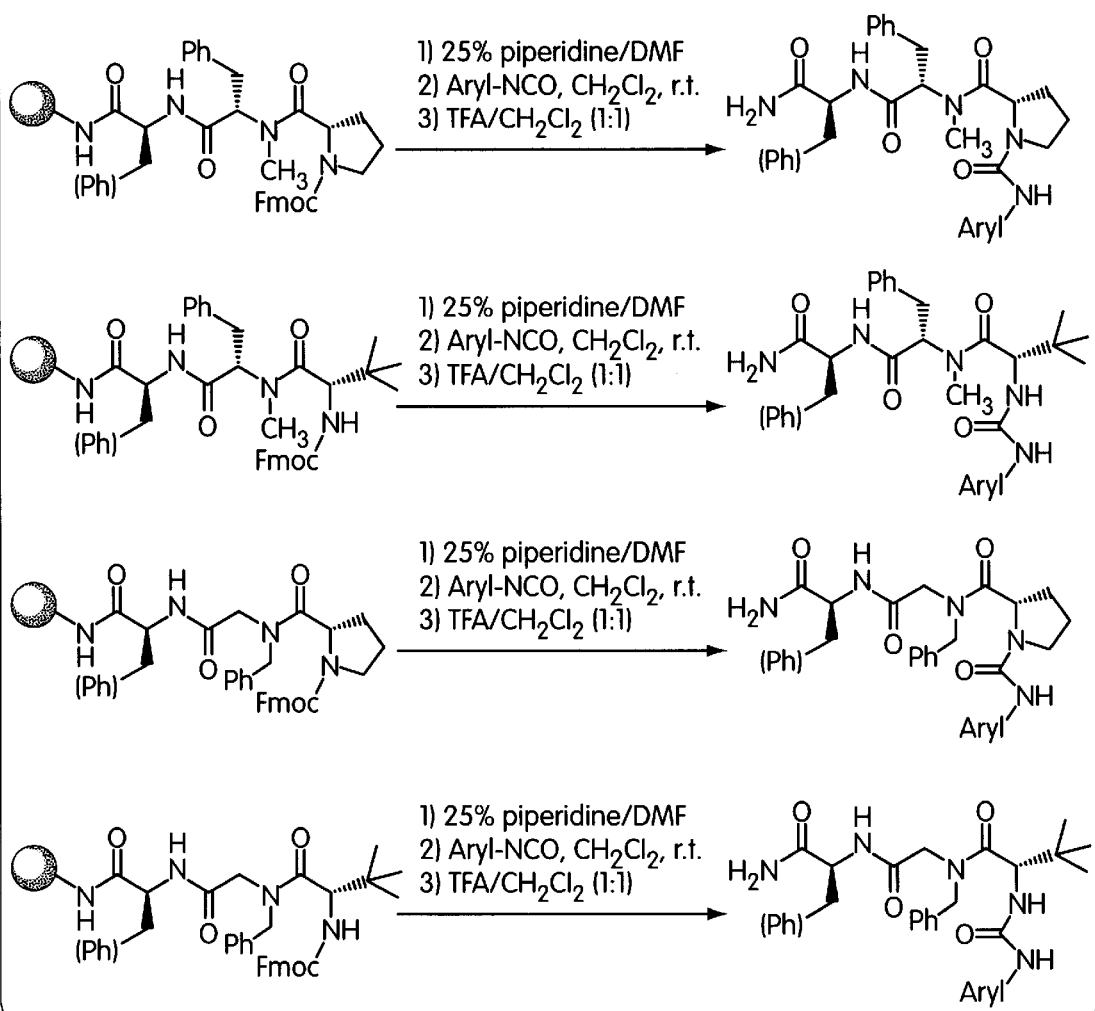
FIG. 37 depicts the final steps in a synthetic strategy utilized to prepare endomnorphin analogues comprising an N-alkylamide functional group.
Figure 40:
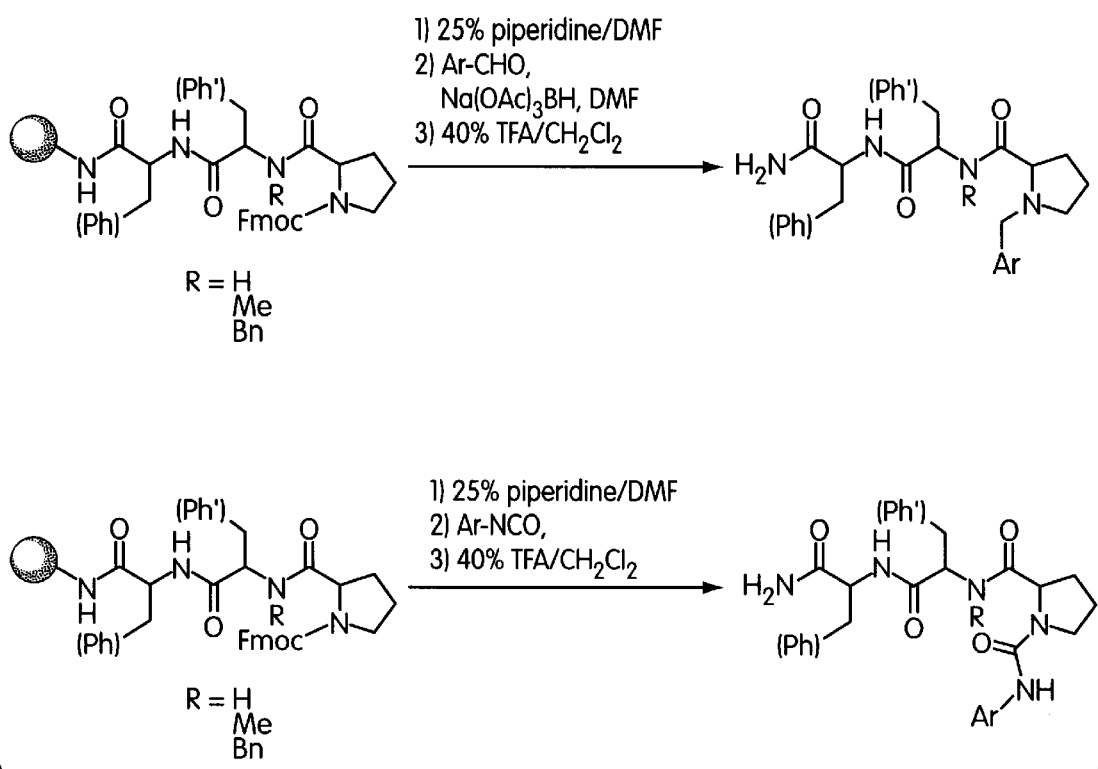
FIG. 40 depicts the final steps in a synthetic strategy utilized to prepare endomorphin analogues comprising either an amine or urea functional group.

Opioids, specifically ligands for the μ-opioid receptor, are the major class of analgesics used in the management of moderate to severe pain because of their effectiveness, ease of titration, and favorable risk-to-benefit ratio. Unfortunately, the opioids currently available are addictive to varying degrees.

Research into the development of new, selective ligands for opioid receptors holds the promise of yielding potent analgesics that lack the addictive characteristics of morphine and its congeners. Applicants herein disclose novel, selective ligands for opioid receptors. Specifically proposed as analgesic agents are compounds based on endomorphin-1 (Tyr-Pro-Trp-Phe-$NH_2$)(Seq. ID No.1), endomorphin-2 (Tyr-Pro-Phe-Phe-$NH_2$)(Seq. ID No.2), and analogs and derivatives thereof. Individual compounds described herein promise to have agonistic, antagonistic, and hybrid effects on opioid receptors. Additionally, new compounds reported herein may possess analgesic properties free from the reward-seeking behavior and potential for physical dependence associated with morphine and heroin.

I. Definitions

For convenience, certain terms employed in the specification, examples, and appended claims are collected here.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251–259. The Hammett constant values are generally negative for electron donating groups (σ[P]=−0.66 for $NH_2$) and positive for electron withdrawing groups (σ[P]=0.78 for a nitro group), σ[P] indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromnatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

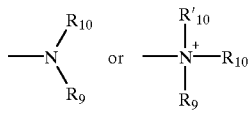

wherein $R_9$, $R_{10}$ and $R'_{10}$ each independently represent a hydrogen, an alkyl, an alkenyl, —(CH$_2$)$_m$—R$_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

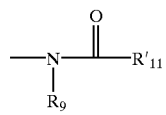

wherein $R_9$ is as defined above, and $R'_{11}$ represents a hydrogen, an alkyl, an alkenyl or —(CH$_2$)$_m$—R$_8$, where m and $R_8$ are as defined above.

The term "amido" is art recognized as an amino-substituted carbonyl and includes a moiety that can be represented by the general formula:

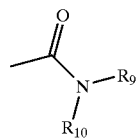

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and $R_8$ are defined above. Representative alkylthio groups include methylthio, ethyl thio, and the like.

The term "carbonyl" is art recognized and includes such moieties as can be represented by the general formula:

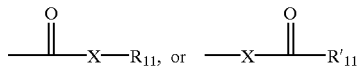

wherein X is a bond or represents an oxygen or a sulfur, and $R_{11}$ represents a hydrogen, an alkyl, an alkenyl, —(CH$_2$)$_m$—R$_8$ or a pharmaceutically acceptable salt, $R'_{11}$ represents a hydrogen, an alkyl, an alkenyl or —(CH$_2$)$_m$—R$_8$, where m and $R_8$ are as defined above. Where X is an oxygen and $R_{11}$ or $R'_{11}$ is not hydrogen, the formula represents an "ester".

Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

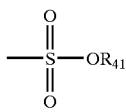

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively, A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

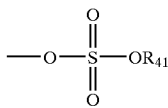

in which $R_{41}$ is as defined above.

The term "sulfonamido" is art recognized and includes a moiety that can be represented by the general formula:

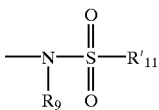

in which $R_9$ and $R'_{11}$ are as defined above.

The term "sulfamoyl" is art-recognized and includes a moiety that can be represented by the general formula:

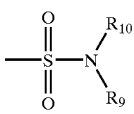

in which $R_9$ and $R_{10}$ are as defined above.

The term "sulfonyl", as used herein, refers to a moiety that can be represented by the general formula:

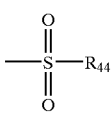

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

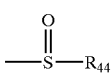

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

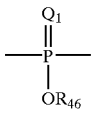

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

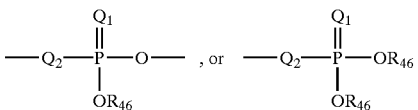

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

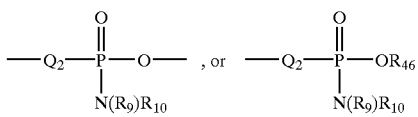

wherein $R_9$ and $R_{10}$ are as defined above, and $Q_2$ represents O, S or N.

A "phosphonarnidite" can be represented in the general formula:

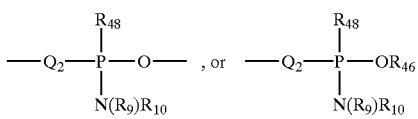

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-RYB Commission on Biochemical Nomenclature (see Biochemistry (1972) 11:1726–1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —CH($NH_2$)COOH portion, as defined by K. D. Kopple, "Peptides and Amino Acids", W. A. Benjamin Inc., New York and Amsterdam, 1966, pages 2 and 33; examples of such side chains of the common amino acids are —$CH_2CH_2SCH_3$ (the side chain of methionine), —$CH_2$($CH_3$)—$CH_2CH_3$ (the side chain of isoleucine), —$CH_2CH$($CH_3$)$_2$ (the side chain of leucine) or H-(the side chain of glycine).

In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs which have been identified as constituents of peptidylglycan bacterial cell walls.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, omithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers. D- and L-α-Amino acids are represented by the following Fischer projections and wedge-and-dash drawings. In the majority of cases, D- and L-amino acids have R- and S-absolute configurations, respectively.

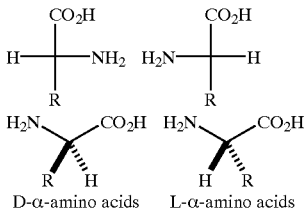

D-α-amino acids    L-α-amino acids

The names of the natural amino acids are abbreviated herein in accordance with the recommendations of IUPAC-IUB.

Among others, the following abbreviations of compound names are utilized herein: Fmoc-L-2-FPA=Fmoc-L-2-Fluorophenylalanine; Fmoc-L-3-FPA=Fmoc-L-3-Fluorophenylalanine; Fmoc-L-4-FPA=Fmoc-L-4-Fluorophenylalanine; Fmoc-L-3-CPA=Fmoc-L-3-Chlorophenylalanine; Fmoc-L-3,4-DCP=Fmoc-L-3,4-Dichlorophenylalanine; Fmoc-L-4-BPA=Fmoc-L-4-Bromophenylalanine; Fmoc-L-BIP=Fmoc-L-4,4'-Biphenylalanine; Fmoc-L-HPA=Fmoc-L-Homophenylalanine; Fmoc-L-1-NAL=Fmoc-L-1-Naphthylalanine; Fmoc-L-2-NAL=Fmoc-L-2-Naphthylalanine; Fmoc-L-4-TAZ=Fmoc-L-4-Thiazoylalanine; Fmoc-L-3-PAL=Fmoc-L-3-Pyridylalanine; Fmoc-L-DIP=Fmoc-L-3,3-Diphenylalanine; Fmoc-L-BAL=Fmoc-3-Benzothienylalanine; Fmoc-L-Thz-OH=Fmoc-L-thiazolidine-4-carboxylic acid; Fmoc-L-tert-Leu=Fmoc-L-α-tert-butyl-Gly; Rink Amide resin=4-(2',4'-Dimethoxyphenyl-Fmoc-aminomethyl)-phenoxy resin; PyBOP®=Benzotriazol-1-yloxy-tris-pyrrolidinophosphonium hexafluorophosphate; and NMM=N-Methylmorpholine.

A "reversed" or "retro" peptide sequence as disclosed herein refers to that part of an overall sequence of covalently-bonded amino acid residues (or analogs or mimetics thereof) wherein the normal carboxyl-to amino direction of peptide bond formation in the amino acid backbone has been reversed such that, reading in the conventional left-to-right direction, the amino portion of the peptide bond precedes (rather than follows) the carbonyl portion. See, generally, Goodman, M. and Chorev, M. Accounts of Chem. Res. 1979, 12, 423.

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention can be formed by utilizing an appropriate amino acid mimetic moiety to link the two adjacent portions of the sequences depicted above utilizing a reversed peptide (reversed amide) bond. In case (a) above, a central residue of a diketo compound may conveniently be utilized to link structures with two amide bonds to achieve a peptidomimetic structure. In case (b) above, a central residue of a diamino compound will likewise be useful to link structures with two amide bonds to form a peptidomimetic structure.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is preferably (D), and the configuration of the non-reversed portion is preferably (L). Opposite or mixed configurations are acceptable when appropriate to optimize a binding activity.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g. the ability to bind to opioid receptors), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

II. Compounds of the Invention

Accordingly, the present invention makes available ligands for opioid receptors which are represented by the general formula 3:

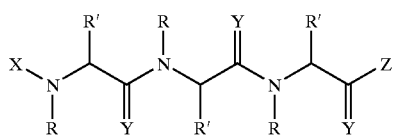

3 wherein
- X represents, independently for each occurrence, —C(O)R, —S(O)$_2$R, or —C(O)N(R)$_2$;
- Y represents, independently for each occurrence, O, S, NR, H$_2$, or (R)$_2$;
- Z represents, independently for each occurrence, —OR, —SR, —N(R)$_2$, or R;
- R represents, independently for each occurrence, H, Me, lower alkyl, lower heteroalkyl, aryl, heteroaryl, aralkyl, or heteroaralkyl;
- R' represents, independently for each occurrence, H, Me, lower alkyl, alkyl, aryl, heteroaryl, or the side chain of any of the naturally occurring α-amino acids;
- R and R' taken together, when attached to adjacent nitrogen and carbon atoms, respectively, may represent a ring; said ring comprising a total of 5–7 backbone atoms inclusive; said ring further comprising at least one nitrogen—the nitrogen bearing this instance of R—and at most two additional heteroatoms selected from the set comprising O, S, N, Se, and P; said ring may be further substituted, and/or fused to another ring; and
- the configuration at any stereocenter of a compound represented by 3 may be R, S, or a mixture of these configurations.

In certain preferred embodiments, the subject compounds are represented by 3 and the above description, wherein
- X represents, independently for each occurrence, —C(O)R", —S(O)$_2$R", or —C(O)N(R")$_2$;
- Y represents, independently for each occurrence, O or (R)$_2$;
- Z represents, independently for each occurrence, —N(R)$_2$, —OR, or —R;
- R represents, independently for each occurrence, H, Me, or lower alkyl;
- R' represents, independently for each occurrence, the side chain of any of the naturally occurring α-amino acids, tert-butyl, 2-, 3-, or 4-halobenzyl, 2-, 3-, or 4-phenylbenzyl, dihalobenzyl, 2-phenylethyl, di- or tri -phenylmethyl, 1- or 2-naphthylmethyl, 2-, 3-, or 4-pyridylmethyl, or 2-, 4-, or 5-thiazolylmethyl; and
- R" represents, independently for each occurrence, H, dihalophenyl, 3,4-dichlorophenyl, 2-, 3-, or 4-anisyl, 2-, 3-, or 4-thioanisyl, 2-, 3-, or 4-trifluoromethylphenyl, 2-, 3, or 4-(trifluoromethoxy) phenyl, β-styrenyl, cyclohexyl, 2-, 3-, or 4-methoxycyclohexyl, 4-hydroxy-2,6-dimethylphenyl, 2-acetylamino-4-methyl-5-thiazolyl, 5-dimethylamino-1-naphthyl, or 2-quinoxalinyl.

In assays based on opioid receptors from mammalian brain, compounds according to general structure 3 preferably have IC$_{50}$ values less than 10 μM against at least one subclass of opioid receptor, more preferably less than 5 μM, and most preferably less than 1 μM.

In certain preferred embodiments, the subject compounds are represented by general structure 4:

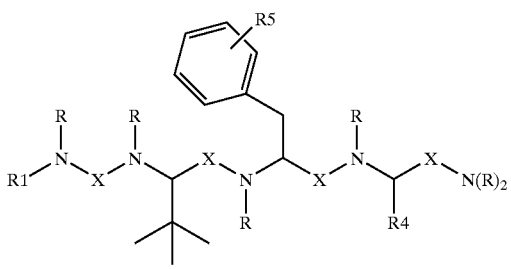

4 wherein
- X represents, independently for each occurrence, —C(O)—, —C(R)$_2$—, —S(O)$_2$—, or —P(O)(OR)—;
- R represents, independently for each occurrence, H, Me, lower alkyl, lower heteroalkyl, aryl, heteroaryl, aralkyl, or heteroaralkyl;
- R1 is selected from the group comprising 2-, 3-, and 4-anisyl, dihalophenyl, 3,4-dichlorophenyl, 4-hydroxy-2,6-dimethylphenyl, 2-, 3-, and 4-trifluoromethylphenyl, 2-, 3-, and 4-thioanisyl;
- R4 is selected from the group comprising 2-, 3-, and 4-halobenzyl, 2-, 3-, and 4-phenylbenzyl, benzyl, diphenylmethyl, triphenylmethyl, dihalobenzyl, 2-phenylethyl, 2-, 3-, and 4-pyridylmethyl;
- R5 is absent, or present between one and five times;
- R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and
- the stereochemical configuration at any stereocenter of a compound represented by 4 is R, S, or a mixture of these configurations.

In assays based on opioid receptors from mammalian brain, compounds according to general structure 4 preferably have IC$_{50}$ values less than 10 μM against at least one subclass of opioid receptor, more preferably less than 5 μM, and most preferably less than 1 μM.

In certain preferred embodiments, the subject compounds are represented by general structure 5:

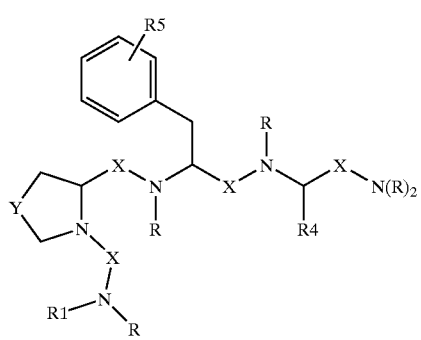

5 wherein
- X represents, independently for each occurrence, —C(O)—, —C(R)$_2$—, —S(O)$_2$-, or —P(O)(OR)—;
- Y represents [C(R)$_2$]$_p$, [O(CR$_2$)$_n$], or [S(CR$_2$)$_n$];
- R represents, independently for each occurrence, H, Me, lower alkyl, lower heteroalkyl, aryl, heteroaryl, aralkyl, or heteroaralkyl;

R1 is selected from the group comprising 2-, 3-, and 4-anisyl, dihalophenyl, 3,4-dichlorophenyl, 4-hydroxy-2,6-dimethylphenyl, 2-, 3-, and 4-trifluoromethylphenyl, 2-, 3-, and 4-thioanisyl;

R4 is selected from the group comprising 2-, 3-, and 4-halobenzyl, 2-, 3-, and 4-phenylbenzyl, benzyl, diphenylmethyl, triphenylmethyl, dihalobenzyl, 2-phenylethyl, 2-, 3-, and 4-pyridylmethyl;

R5 is absent, or present between one and five times;

R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 0 to 2 inclusive;

p is an integer in the range 1 to 3 inclusive; and the stereochemical configuration at any stereocenter of a compound represented by 5 is R, S, or a mixture of these configurations.

In assays based on opioid receptors from mammalian brain, compounds according to general structure 5 preferably have IC$_{50}$ values less than 10 μM against. at least one subclass of opioid receptor, more preferably less than 5 μM, and most preferably less than 1 μM.

In certain preferred embodiments, the subject compounds are represented by the general structure 6:

AA1—AA2—AA3—AA4—NR$_2$ wherein

AA1 represents tyrosine, or a side chain-modified analogue of tyrosine;

AA2 represents proline, or an analogue of proline;

AA3 represents tryptophan, phenylalanine, an analogue of tryptophan, or an analogue of phenylalanine;

AA4 represents phenylalanine, or an analogue of phenylalanine;

the linkages between the individual amino acids are, independently for each occurrence, amide bonds, N-methylamide bonds, or —CH$_2$NR—;

R represents, independently for each occurrence, H, Me, lower alkyl, lower heteroalkyl, aryl, heteroaryl, aralkyl, or heteroaralkyl; and the stereochemical configuration at any stereocenter of a compound represented by 6 is R, S, or a mixture of these configurations.

In further preferred embodiments, the subject compounds are represented by general formula 6, wherein:

AA1 represents phenylalanine, or an analogue of phenylalanine;

AA2 represents tryptophan, phenylalanine, an analogue of tryptophan, or an analogue of phenylalanine;

AA3 represents proline, or an analogue of proline;

AA4 represents tyrosine, or an analogue of tyrosine;

the linkages between the individual amino acids are, independently for each occurrence, amide bonds, N-methylamide bonds, or —CH$_2$NR—;

R represents, independently for each occurrence, H, Me, lower alkyl, lower heteroalkyl, aryl, heteroaryl, aralkyl, or heteroaralkyl; and the stereochemical configuration at any stereocenter of a compound represented by 6 may be R, S, or a mixture of these configurations.

In assays based on opioid receptors from mammalian brain, compounds according to general structure 6 preferably have IC$_{50}$ values less than 10 μM against at least one subclass of opioid receptor, more preferably less than 5 μM, and most preferably less than 1 μM.

In more preferred embodiments, the subject compounds are represented by the general structure 7:

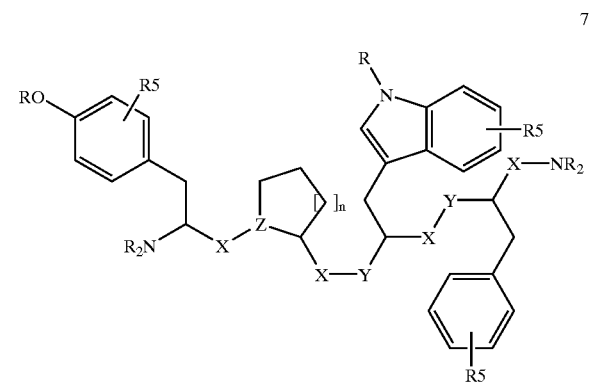

7 wherein

R represents, independently for each occurrence, H, Me, lower alkyl, lower heteroalkyl, aryl, heteroaryl, aralkyl, or heteroaralkyl;

X represents, independently for each occurrence, —C(O)—, —C(S)—, —CH$_2$—, —S(O)$_2$—, or —P(O)(OR)—;

Y represents, independently for each occurrence, NR, O, S, or C(R)$_2$;

Z represents N, or CR;

R5, independently for each occurrence, is absent, or present between one and the maximum number of times permitted by the additional substitution on the relevant aromatic ring;

R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 1 to 3 inclusive; and the stereochemical configuration at any stereocenter of a compound represented by 7 may be R, S, or a mixture of these configurations.

Additional preferred embodiments of the subject compounds are represented by 7, and the definitions above, wherein X—Y taken together represents, independently for each occurrence, (E)—CH=CH, (Z)—CF=CH, (Z)—CH=CF, or —C(O)CH(F)—.

In assays based on opioid receptors from mammalian brain, compounds according to general structure 7 preferably have IC$_{50}$ values less than 10 μM against at least one subclass of pioid receptor, more preferably less than 5 μM, and most preferably less than 1 μM.

In more preferred embodiments, the subject compounds are represented by the general structure 8:

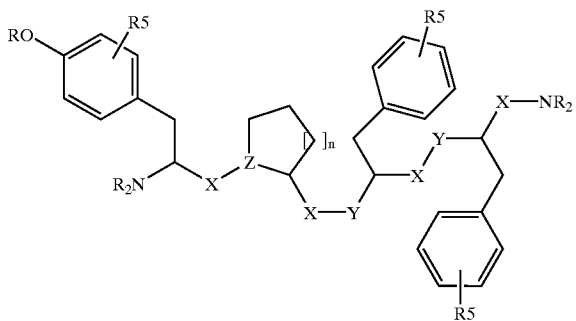

8 wherein

R represents, independently for each occurrence, H, Me, lower alkyl, lower heteroalkyl, aryl, heteroaryl, aralkyl, or heteroaralkyl;

X represents, independently for each occurrence, —C(O)—, —C(S)—, —CH$_2$—, —S(O)$_2$—, or —P(O)(OR)—;

Y represents, independently for each occurrence, NR, O, S, or C(R)$_2$;

Z represents N, or CR;

R5, independently for each occurrence, is absent, or present between one and the maximum number of times permitted by the additional substitution on the relevant aromatic ring;

R$_5$, when present, is selected independently for each occurrence from the set consisting of Me, lower alkyl, lower heteroalkyl, aryl, heteroaryl, aratkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 1 to 3 inclusive; and the stereochemical configuration at any stereocenter of a compound represented by 8 may be R, S, or a mixture of these configurations.

Additional preferred embodiments of the subject compounds are represented by 8, and the definitions above, wherein X—Y taken together represents, independently for each occurrence, (E)—CH═CH, (Z)—CF═CH, (Z)—CH═CF, or —C(O)CH(F)—.

In assays based on opioid receptors from mammalian brain, compounds according to general structure 8 preferably have IC$_{50}$ values less than 10 µM against at least one subclass of opioid receptor, more preferably less than 5 µM, and most preferably less than 1 µM.

In additional preferred embodiments, the subject compounds are represented by general structure 9:

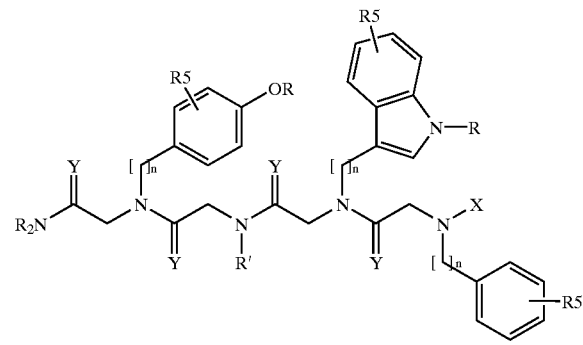

9 wherein

R represents, independently for each occurrence, H, Me, lower alkyl, lower heteroalkyl, aryl, heteroaryl, aralkyl, or heteroaralkyl;

R' represents Me, lower alkyl, aryl, aralkyl, heteroalkyl, or heteroaryl;

Y represents, independently for each occurrence, O, S, NR, or H$_2$;

X represents H, Me, lower alkyl, aryl, aralkyl, heteroalkyl, heteroaryl, acyl, sulfonyl, —C(O)OR, or —C(O)N(R)$_2$;

R5, independently for each occurrence, is absent, or present between one and the maximum number of times permitted by the additional substitution on the relevant aromatic ring;

R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and n represents, independently for each occurrence, an integer in the range 0 to 3 inclusive.

In assays based on opioid receptors from mammalian brain, compounds according to general structure 9 preferably have IC$_{50}$ values less than 10 µM against at least one subclass of opioid receptor, more preferably less than 5 µM, and most preferably less than 1 µM.

In additional preferred embodiments, the subject compounds are represented by general structure 10:

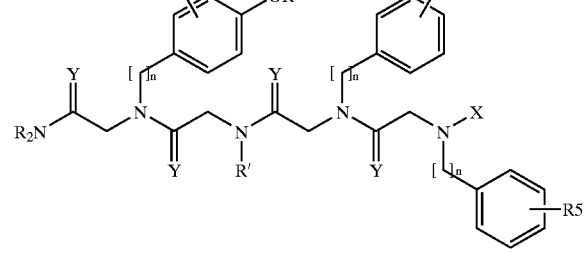

10 wherein
- R represents, independently for each occurrence, H, Me, lower alkyl, lower heteroalkyl, aryl, heteroaryl, aralkyl, or heteroaralkyl;
- R' represents Me, lower alkyl, aryl, aralkyl, heteroalkyl, or heteroaryl;
- Y represents, independently for each occurrence, O, S, NR, or $H_2$; and
- X represents H, Me, lower alkyl, aryl, aralkyl, heteroalkyl, heteroaryl, acyl, sulfonyl, —C(O)OR, or —C(O)N(R)$_2$;
- R5, independently for each occurrence, is absent, or present between one and the maximum number of times permitted by the additional substitution on the relevant aromatic ring;
- $R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and
- n represents, independently for each occurrence, an integer in the range 0 to 3 inclusive.

In assays based on opioid receptors from mammalian brain, compounds according to general structure 10 preferably have $IC_{50}$ values less than 10 µM against at least one subclass of opioid receptor, more preferably less than 5 µM, and most preferably less than 1 µM.

In additional preferred embodiments, the subject compounds are represented by general structure 11:

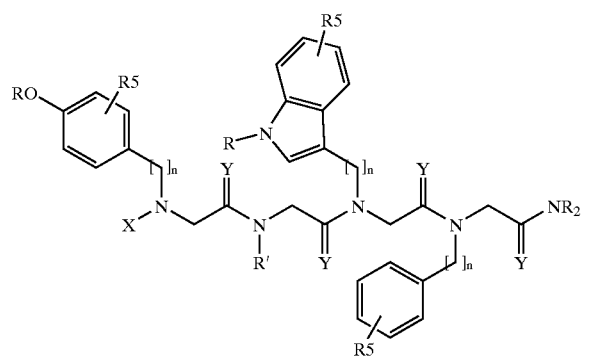

11 wherein
- R represents, independently for each occurrence, H, Me, lower alkyl, lower heteroalkyl, aryl, heteroaryl, aralkyl, or heteroaralkyl;
- R' represents Me, lower alkyl, aryl, aralkyl, heteroalkyl, or heteroaryl;
- Y represents, independently for each occurrence, O, S, NR, or $H_2$;
- X represents H, Me, lower alkyl, aryl, aralkyl, heteroalkyl, heteroaryl, acyl, sulfonyl, —C(O)OR, or —C(O)N(R)$_2$;
- R5, independently for each occurrence, is absent, or present between one and the maximum number of times permitted by the additional substitution on the relevant aromatic ring;
- $R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and
- n represents, independently for each occurrence, an integer in the range 0 to 3 inclusive.

In assays based on opioid receptors from mammalian brain, compounds according to general structure 11 preferably have $IC_{50}$ values less than 10 µM against at least one subclass of opioid receptor, more preferably less than 5 µM, and most preferably less than 1 µM.

In additional preferred embodiments, the subject compounds are represented by general structure 12:

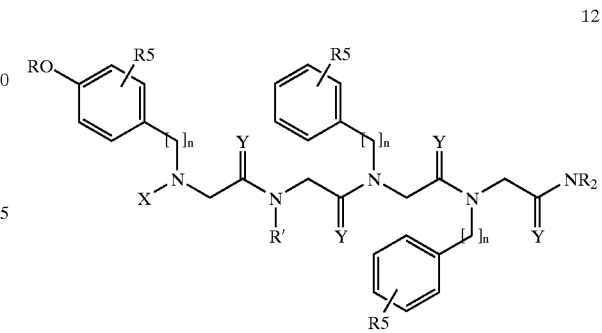

12 wherein
- R represents, independently for each occurrence, H, Me, lower alkyl, lower heteroalkyl, aryl, heteroaryl, aralkyl, or heteroaralkyl;
- R' represents Me, lower alkyl, aryl, aralkyl, heteroalkyl, or heteroaryl;
- Y represents, independently for each occurrence, O, S, NR, or $H_2$;
- X represents H, Me, lower alkyl, aryl, aralkyl, heteroalkyl, heteroaryl, acyl, sulfonyl, —C(O)OR, or —C(O)N(R)$_2$;
- R5, independently for each occurrence, is absent, or present between one and the maximum number of times permitted by the additional substitution on the relevant aromatic ring;
- $R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and
- n represents, independently for each occurrence, an integer in the range 0 to 3 inclusive.

In assays based on opioid receptors from mammalian brain, compounds according to general structure 12 preferably have $IC_{50}$ values less than 10 µM against at least one subclass of opioid receptor, more preferably less than 5 µM, and most preferably less than 1 µM.

In further preferred embodiments, the subject compounds are represented by general structure 13:

13

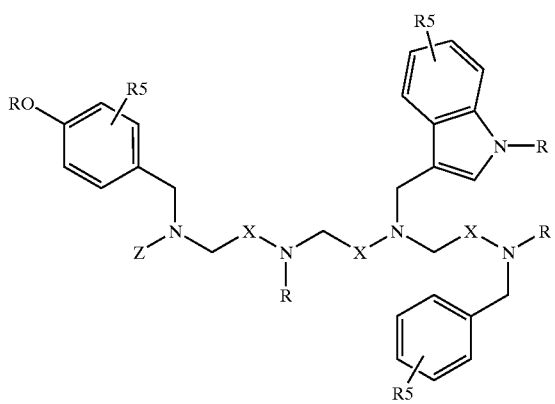

wherein
- X represents, independently for each occurrence, —C(O)—, —C(S)—, —C(R)$_2$—, —S(O)$_2$—, or —P(O)(OR)—;
- Z represents H, Me, lower alkyl, —C(O)R, —C(O)OR, or —C(O)N(R)$_2$;
- R represents, independently for each occurrence, H, Me, lower alkyl, lower heteroalkyl, aryl, heteroaryl, aralkyl, or heteroaralkyl;
- R5, independently for each occurrence, is absent, or present between one and the maximum number of times permitted by the additional substitution on the relevant aromatic ring; and
- R$_5$, when present, is selected independently for each occurrence from the set consisting of Me, lower alkyl, lower heteroalkyl, aryl, heteroaryl, aralkyl, heteroaratkyl, cycloalkyl, heterocycloalkyl, halogen, hydroxyl, alkoxyl, nitro, nitroso, cyano, acyl, acylamino, amido, sulfonyl, sulfonamido, and acyloxy.

In assays based on opioid receptors from mammalian brain, compounds according to general structure 13 preferably have IC$_{50}$ values less than 10 μM against at least one subclass of opioid receptor, more preferably less than 5 μM, and most preferably less than 1 μM.

In further preferred embodiments, the subject compounds are represented by general structure 14:

14

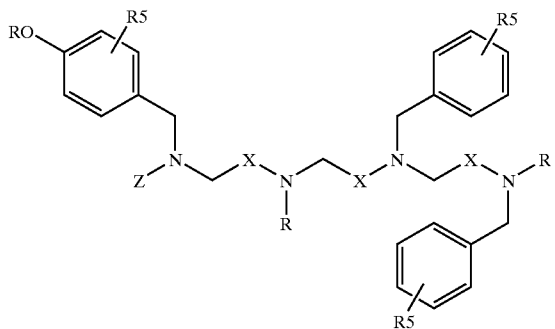

wherein
- X represents, independently for each occurrence, —C(O)—, —C(S)—, —C(R)$_2$—, —S(O)$_2$—, or —P(O)(OR)—;
- Z represents H, Me, lower alkyl, —C(O)R, —C(O)OR, or —C(O)N(R)$_2$; and
- R represents, independently for each occurrence, H, Me, lower alkyl, lower heteroalkyl, aryl, heteroaryl, aralkyl, or heteroaralkyl;
- R5, independently for each occurrence, is absent, or present between one and the maximum number of times permitted by the additional substitution on the relevant aromatic ring; and
- R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy.

In assays based on opioid receptors from mammalian brain, compounds according to general structure 14 preferably have IC$_{50}$ values less than 10 μM against at least one subclass of opioid receptor, more preferably less than 5 μM, and most preferably less than 1 μM.

In further preferred embodiments, the subject compounds are represented by general structure 15:

15

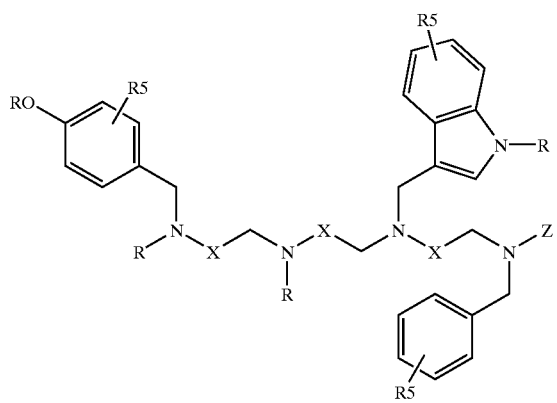

wherein
- X represents, independently for each occurrence, —C(O)—, —C(S)—, —C(R)$_2$—, —S(O)$_2$—, or —P(O)(OR)—;
- Z represents H, Me, lower alkyl, —C(O)R, —C(O)OR, or —C(O)N(R)$_2$; and
- R represents, independently for each occurrence, H, Me, lower alkyl, lower heteroalkyl, aryl, heteroaryl, aralkyl, or heteroaralkyl;
- R5, independently for each occurrence, is absent, or present between one and the maximum number of times permitted by the additional substitution on the relevant aromatic ring; and
- R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy.

In assays based on opioid receptors from mammalian brain, compounds according to general structure 15 preferably have IC$_{50}$ values less than 10 μM against at least one subclass of opioid receptor, more preferably less than 5 μM, and most preferably less than 1 μM.

In further preferred embodiments, the subject compounds are represented by general structure 16:

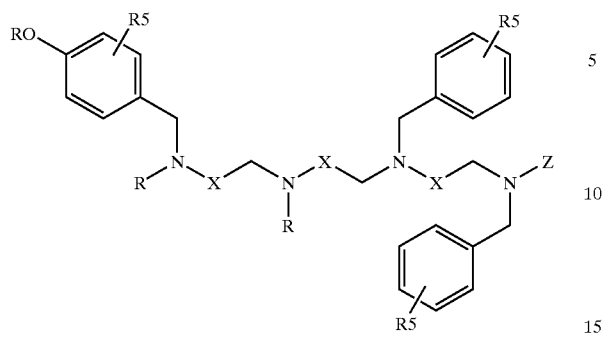

16 wherein
- X represents, independently for each occurrence, —C(O)—, —C(S)—, —C(R)$_2$—, —S(O)$_2$—, or —P(O)(OR)—;
- Z represents H, Me, lower alkyl, —C(O)R, —C(O)OR, or —C(O)N(R)$_2$; and
- R represents, independently for each occurrence, H, Me, lower alkyl, lower heteroalkyl, aryl, heteroaryl, aralkyl, or heteroaralkyl;
- R5, independently for each occurrence, is absent, or present between one and the maximum number of times permitted by the additional substitution on the relevant aromatic ring; and
- R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy.

In assays based on opioid receptors from mammalian brain, compounds according to general structure 16 preferably have IC$_{50}$ values less than 10 $\mu$M against at least one subclass of opioid receptor, more preferably less than 5 $\mu$M, and most preferably less than 1 $\mu$M.

In yet another preferred embodiment, the subject compound is provided as a retro-inverso peptidomimetic such as 17:

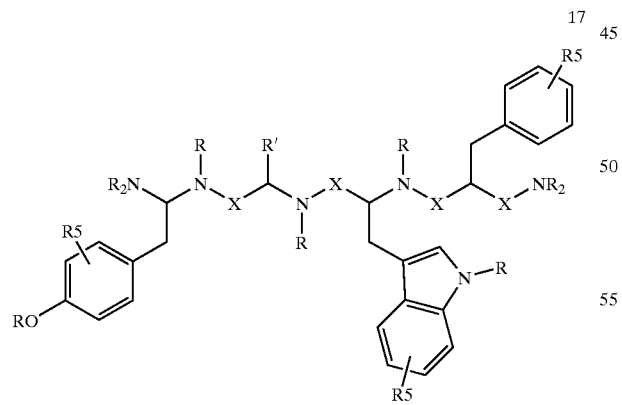

17 wherein
- X represents, independently for each occurrence, —C(O)—, —C(S)—, —C(R)$_2$—, —S(O)$_2$—, or —P(O)(OR)—;
- R represents, independently for each occurrence, H, Me, lower alkyl, lower heteroalkyl, aryl, heteroaryl, aralkyl, or heteroaralkyl;
- R' represents H, Me, lower alkyl, aryl, heteroalkyl, heteroaryl, or the side chain of any naturally-occurring α-amino acid; or R' and the occurrence of R on the nitrogen bonded directly to the carbon bearing R' taken together form a ring, comprising between 5 and 7 ring atoms inclusive;
- R5, independently for each occurrence, is absent, or present between one and the maximum number of times permitted by the additional substitution on the relevant aromatic ring;
- R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and
- the stereochemical configuration at any stereocenter of a compound represented by 17 may be R, S, or a mixture of these configurations.

In more preferred embodiments, the subject compounds are represented by 17 and the attendant definitions, wherein X represents, independently for each occurrence, —C(O)—, or —C(R)$_2$—.

In assays based on opioid receptors from mammalian brain, compounds according to general structure 17 preferably have IC$_{50}$ values less than 10 $\mu$M against at least one subclass of opioid receptor, more preferably less than 5 $\mu$M, and most preferably less than 1 $\mu$M.

In yet another preferred embodiment, the subject compound is provided as a retro-inverso peptidomimetic such as 18:

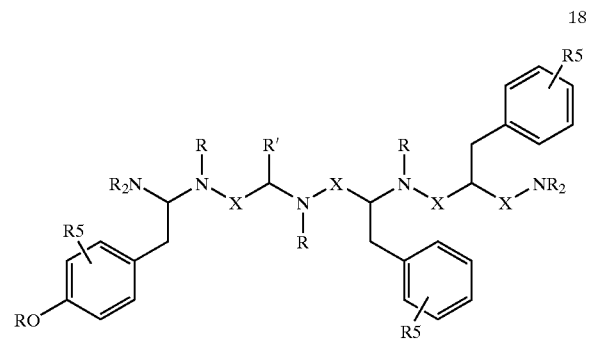

18 wherein
- X represents, independently for each occurrence, —C(O)—, —C(S)—, —C(R)$_2$—, —S(O)$_2$—, or —P(O)(OR)—;
- R represents, independently for each occurrence, H, Me, lower alkyl, lower heteroalkyl, aryl, heteroaryl, aralkyl, or heteroaralkyl;
- R' represents H, Me, lower alkyl, aryl, heteroalkyl, heteroaryl, or the side chain of any naturally-occurring α-amino acid; or R' and the occurrence of R on the nitrogen bonded directly to the carbon bearing R' taken together form a ring, comprising between 5 and 7 ring atoms inclusive;
- R5, independently for each occurrence, is absent, or present between one and the maximum number of times permitted by the additional substitution on the relevant aromatic ring;
- R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and the stereochemical configuration at any stereocenter of a compound represented by 18 may be R, S, or a mixture of these configurations.

In more preferred embodiments, the subject compounds are represented by 18 and the attendant definitions, wherein X represents, independently for each occurrence, —C(O)—, or —C(R)$_2$—.

In assays based on opioid receptors from mammalian brain, compounds according to general structure 18 preferably have IC$_{50}$ values less than 10 $\mu$M against at least one subclass of opioid receptor, more preferably less than 5 $\mu$M, and most preferably less than 1 $\mu$M.

In additional preferred embodiments, the subject compound is provided as a benzodiazepine peptidomimetic such as 19:

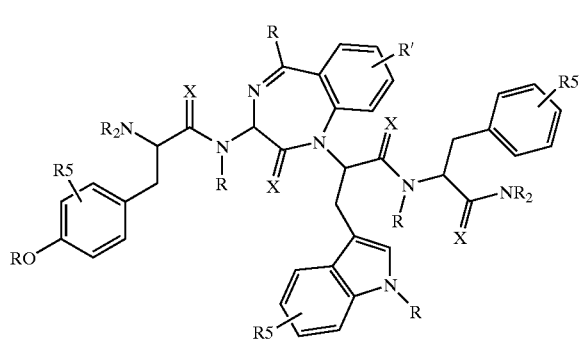

19 wherein

X represents, independently for each occurrence, O, S, H$_2$, or NR;

R represents, independently for each occurrence, H, Me, lower alkyl, lower heteroalkyl, aryl, heteroaryl, aralkyl, or heteroaralkyl;

R' may be absent, or present between one and four times inclusive;

R' represents, independently for each occurrence, is selected from the set comprising H, Me, lower alkyl, halogen, nitro, nitroso, cyano, acyl, acylamino, amido, sulfonyl, and acyloxy;

R5, independently for each occurrence, is absent, or present between one and the maximum number of times permitted by the additional substitution on the relevant aromatic ring;

R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and the stereochemical configuration at any stereocenter of a compound represented by 19 may be R, S, or a mixture of these configurations.

In assays based on opioid receptors from mammalian brain, compounds according to general structure 19 prefer ably have IC$_{50}$ values less than 10 $\mu$M against at least one subclass of opioid receptor, more preferably less than 5 $\mu$M, and most preferably less than 1 $\mu$M.

In additional preferred embodiments, the subject compound is provided as a benzodiazepine peptidomimetic such as 20:

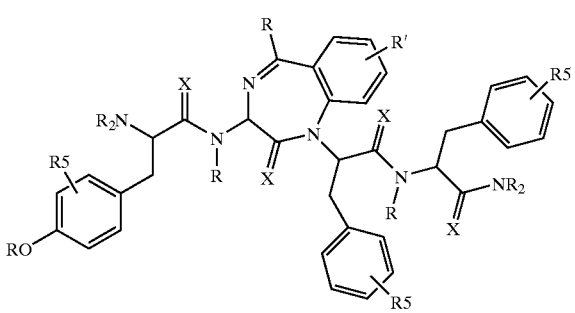

20 wherein

X represents, independently for each occurrence, O, S, H$_2$, or NR;

R represents, independently for each occurrence, H, Me, lower alkyl, lower heteroalkyl, aryl, heteroaryl, aralkyl, or heteroaralkyl;

R' may be absent, or present between one and four times inclusive;

R', independently for each occurrence, is selected from the set comprising H, Me, lower alkyl, halogen, nitro, nitroso, cyano, acyl, acylamino, amido, sulfonyl, and acyloxy;

R5, independently for each occurrence, is absent, or present between one and the maximum number of times permitted by the additional substitution on the relevant aromatic ring;

R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and the stereochemical configuration at any stereocenter of a compound represented by 20 may be R, S, or a mixture of these configurations.

In assays based on opioid receptors from mammalian brain, compounds according to general structure 20 preferably have IC$_{50}$ values less than 10 $\mu$M against at least one subclass of opioid receptor, more preferably less than 5 $\mu$M, and most preferably less than 1 $\mu$M.

In additional preferred embodiments, the subject compounds are represented by general structure 21 (for other compounds incorporating the 1-azabicyclo[4.3.0]nonane surrogate for proline, see: Kim and Germanas J. Org. Chem. 1997, 62, 2847):

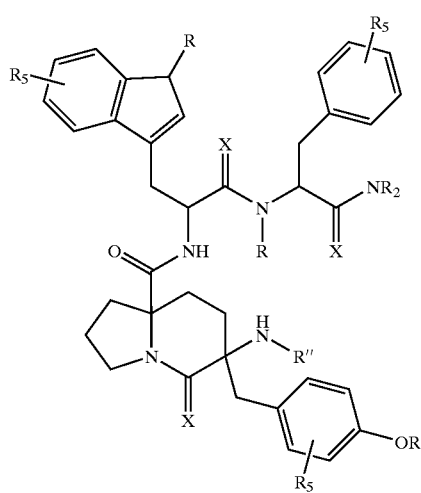

21

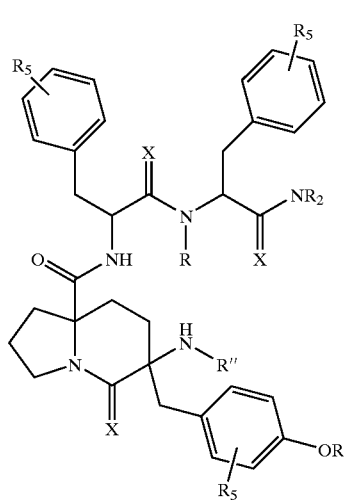

22 wherein

X represents, independently for each occurrence, O, S, $H_2$, or NR;

R represents, independently for each occurrence, H, Me, lower alkyl, lower heteroalkyl, aryl, heteroaryl, aralkyl, or heteroaralkyl;

R" represents H, acyl, thioacyl, sulfonyl, phosphonyl, —C(O)Oalkyl, —C(O)Oaryl, or —C(O)$NR_2$;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and the stereochemical configuration at any stereocenter of a compound represented by 21 may be R, S, or a mixture of these configurations.

In assays based on opioid receptors from mammalian brain, compounds according to general structure 21 preferably have $IC_{50}$ values less than 10 µM against at least one subclass of opioid receptor, more preferably less than 5 µM, and most preferably less than 1 µM.

In additional preferred embodiments, the subject compounds are represented by general structure 22:

wherein

X represents, independently for each occurrence, O, S, $H_2$, or NR;

R represents, independently for each occurrence, H, Me, lower alkyl, lower heteroalkyl, aryl, heteroaryl, aralkyl, or heteroaralkyl;

R" represents H, acyl, thioacyl, sulfonyl, phosphonyl, —C(O)Oalkyl, —C(O)Oaryl, or —C(O)$NR_2$;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and the stereochemical configuration at any stereocenter of a compound represented by 22 may be R, S, or a mixture of these configurations.

In assays based on opioid receptors from mammalian brain, compounds according to general structure 22 preferably have $IC_{50}$ values less than 10 µM against at least one subclass of opioid receptor, more preferably less than 5 µM, and most preferably less than 1 µM.

In additional preferred embodiments, the subject compounds are represented by general structure 23 (for speculation on the potential of N-acyl piperazic acids as surrogates for proline, see: Xi, Alemany, and Ciufolini J. Am. Chem. Soc. 1998, 120, 80):

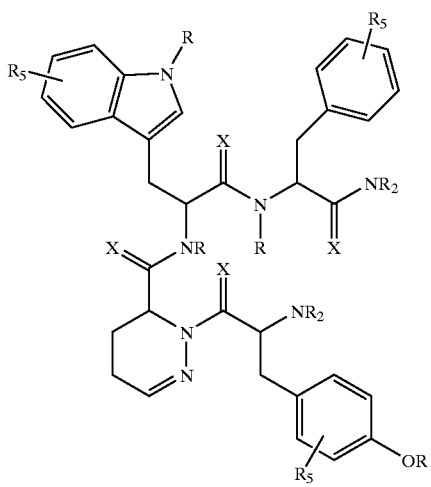

23

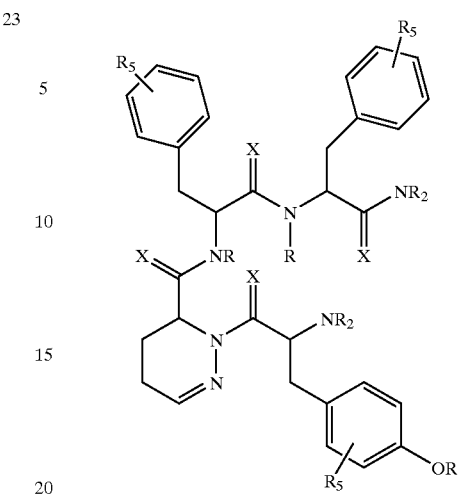

24 wherein

X represents, independently for each occurrence, O, S, $H_2$, or NR;

R represents, independently for each occurrence, H, Me, lower alkyl, lower heteroalkyl, aryl, heteroaryl, aralkyl, or heteroaralkyl;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and the stereochemical configuration at any stereocenter of a compound represented by 23 may be R, S, or a mixture of these configurations.

In assays based on opioid receptors from mammalian brain, compounds according to general structure 23 preferably have $IC_{50}$ values less than 10 $\mu$M against at least one subclass of opioid receptor, more preferably less than 5 $\mu$M, and most preferably less than 1 $\mu$M.

In additional preferred embodiments, the subject compounds are represented by general structure 24:

wherein

X represents, independently for each occurrence, O, S, $H_2$, or NR;

R represents, independently for each occurrence, H, Me, lower alkyl, lower heteroalkyl, aryl, heteroaryl, aralkyl, or heteroaralkyl;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and the stereochemical configuration at any stereocenter of a compound represented by 24 may be R, S, or a mixture of these configurations.

In assays based on opioid receptors from mammalian brain, compounds according to general structure 24 preferably have $IC_{50}$ values less than 10 $\mu$M against at least one subclass of opioid receptor, more preferably less than 5 $\mu$M, and most preferably less than 1 $\mu$M.

In additional preferred embodiments, the subject compounds are represented by general structure 25:

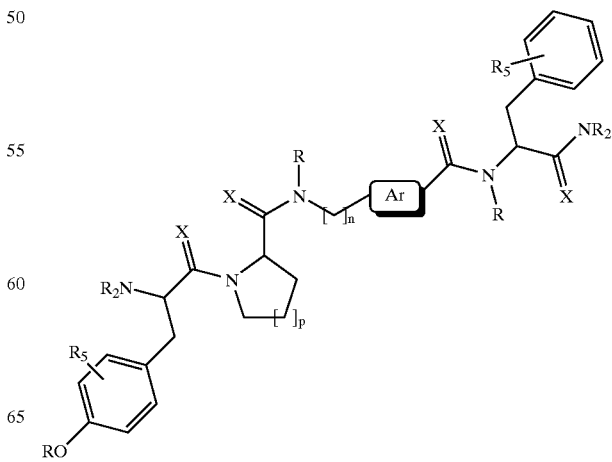

25 wherein
X represents, independently for each occurrence, O, S, $H_2$, or NR;

R represents, independently for each occurrence, H, Me, lower alkyl, lower heteroalkyl, aryl, heteroaryl, aralkyl, or heteroaralkyl;

Ar represents a monocyclic or bicyclic aromatic or heteroaromatic nucleus, or a biaromatic, aromatic-heteroaromatic, or biheteroaromatic nucleus;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 0 to 3 inclusive;

p is an integer in the range 1 to 3 inclusive; and the stereochemical configuration at any stereocenter of a compound represented by 25 may be R, S, or a mixture of these configurations.

In assays based on opioid receptors from mammalian brain, compounds according to general structure 25 preferably have $IC_{50}$ values less than 10 μM against at least one subclass of opioid receptor, more preferably less than 5 μM, and most preferably less than 1 μM.

In certain preferred embodiments, the subject compounds are represented by 25 and the definitions above, wherein Ar represents phenylene; and n is 0 or 1.

In additional preferred embodiments, the subject compounds are compounds represented by general structure 26:

26

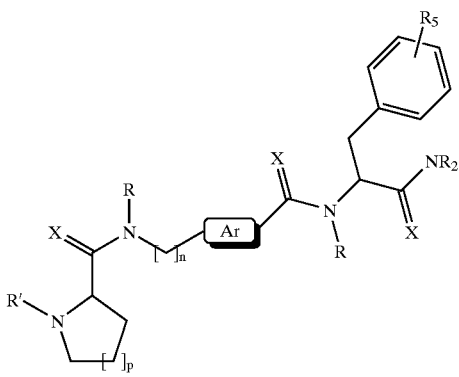

wherein
X represents, independently for each occurrence, O, S, $H_2$, or NR;

R represents, independently for each occurrence, H, Me, lower alkyl, lower heteroalkyl, aryl, heteroaryl, aralkyl, or heteroaralkyl;

Ar represents a monocyclic or bicyclic aromatic or heteroaromatic nucleus, or a biaromatic, aromatic-heteroaromatic, or biheteroaromatic nucleus;

R' represents H, Me, lower alkyl, aryl, aralkyl, heteroalkyl, heteroaryl, acyl, sulfonyl, —C(O)OR, or —C(O)N(R)$_2$;

$R_5$ is absent, or present between one and five times;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 0 to 3 inclusive;

p is an integer in the range 1 to 3 inclusive; and the stereochemical configuration at any stereocenter of a compound represented by 26 may be R, S, or a mixture of these configurations.

In assays based on opioid receptors from mammalian brain, compounds according to general structure 26 preferably have $IC_{50}$ values less than 10 μM against at least one subclass of opioid receptor, more preferably less than 5 μM, and most preferably less than 1 μM.

In certain preferred embodiments, the subject compounds are represented by 26 and the definitions above, wherein Ar represents phenylene; R' represents acyl, sulfonyl, —C(O)NR$_2$, or —C(O)OR; and n is 0 or 1.

In additional preferred embodiments, the subject compounds are compounds represented by general structure 27:

27

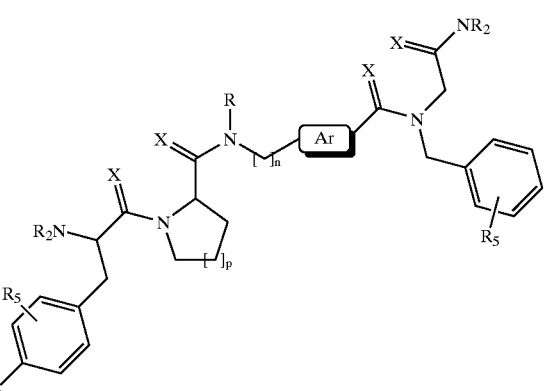

wherein
X represents, independently for each occurrence, O, S, $H_2$, or NR;

R represents, independently for each occurrence, H, Me, lower alkyl, lower heteroalkyl, aryl, heteroaryl, aralkyl, or heteroaralkyl;

Ar represents a monocyclic or bicyclic aromatic or heteroaromatic nucleus, or a biaromatic, aromatic-heteroaromatic, or biheteroaromatic nucleus;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 0 to 3 inclusive;

p is an integer in the range 1 to 3 inclusive; and the stereochemical configuration at any stereocenter of a compound represented by 27 may be R, S, or a mixture of these configurations.

In assays based on opioid receptors from mammalian brain, compounds according to general structure 27 preferably have $IC_{50}$ values less than 10 μM against at least one subclass of opioid receptor, more preferably less than 5 μM, and most preferably less than 1 μM.

In certain preferred embodiments, the subject compounds are represented by 27 and the definitions above, wherein Ar represents phenylene; and n is 0 or 1.

In additional preferred embodiments, the subject compounds are peptidomimetics represented by general structure 28:

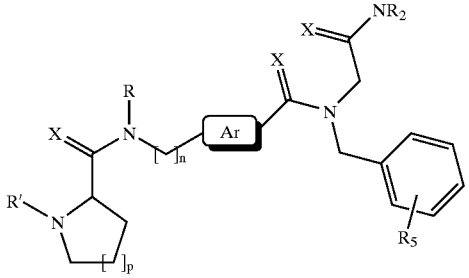

28 wherein

X represents, independently for each occurrence, O, S, H$_2$, or NR;

R represents, independently for each occurrence, H, Me, lower alkyl, lower heteroalkyl, aryl, heteroaryl, aralkyl, or heteroaralkyl;

Ar represents a monocyclic or bicyclic aromatic or heteroaromatic nucleus, or a biaromatic, aromatic-heteroaromatic, or biheteroaromatic nucleus;

R' represents H, Me, lower alkyl, aryl, aralkyl, heteroalkyl, heteroaryl, acyl, sulfonyl, —C(O)OR, or —C(O)N(R)$_2$;

R$_5$ is absent, or present between one and five times;

R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 0 to 3 inclusive;

p is an integer in the range 1 to 3 inclusive; and the stereochemical configuration at any stereocenter of a compound represented by 28 may be R, S, or a mixture of these configurations.

In assays based on opioid receptors from mammalian brain, compounds according to general structure 28 preferably have IC$_{50}$ values less than 10 μM against at least one subclass of opioid receptor, more preferably less than 5 μM, and most preferably less than 1 μM.

In certain preferred embodiments, the subject compounds are represented by 28 and the definitions above, wherein Ar represents phenylene; R' represents acyl, sulfonyl, —C(O)NR$_2$, or —C(O)OR; and n is 0 or 1.

In additional preferred embodiments, the subject compounds are represented by general structure 29:

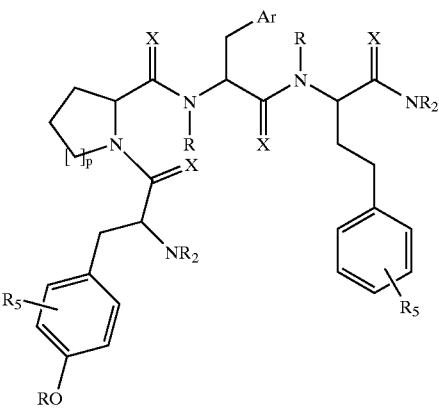

29 wherein

X represents, independently for each occurrence, O, S, H$_2$, or NR;

R represents, independently for each occurrence, H, Me, lower alkyl, lower heteroalkyl, aryl, heteroaryl, aralkyl, or heteroaralkyl;

Ar represents phenyl or 1-R-3-indolyl;

R$_5$, independently for each occurrence, is absent, or present between one and the maximum number of times permitted by the additional substitution on the relevant aromatic ring;

R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

p is an integer in the range 1 to 3 inclusive; and the stereochemical configuration at any stereocenter of a compound represented by 29 may be R, S, or a mixture of these configurations.

In assays based on opioid receptors from mammalian brain, compounds according to general structure 29 preferably have IC$_{50}$ values less than 10 μM against at least one subclass of opioid receptor, more preferably less than 5 μM, and most preferably less than 1 μM.

In additional preferred embodiments, the subject compounds are peptidomimetics resented by general structure 30:

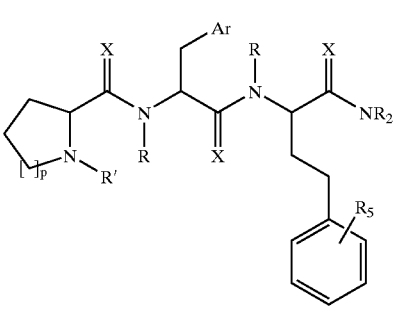

30 wherein

X represents, independently for each occurrence, O, S, H$_2$, or NR;

R represents, independently for each occurrence, H, Me, lower alkyl, lower heteroalkyl, aryl, heteroaryl, aralkyl, or heteroaralkyl;

Ar represents phenyl or 1-R-3-indolyl;

R' represents H, Me, lower alkyl, aryl, aralkyl, heteroalkyl, heteroaryl, acyl, sulfonyl, —C(O)OR, or —C(O)N(R)$_2$;

$R_5$ is absent, or present between one and five times;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

p is an integer in the range 1 to 3 inclusive; and the stereochemical configuration at any stereocenter of a compound represented by 30 may be R, S, or a mixture of these configurations.

In assays based on opioid receptors from mammalian brain, compounds according to general structure 30 preferably have IC$_{50}$ values less than 10 $\mu$M against at least one subclass of opioid receptor, more preferably less than 5 $\mu$M, and most preferably less than 1 $\mu$M.

In certain preferred embodiments, the subject compounds are represented by 30 and the definitions above, wherein R' represents acyl, sulfonyl, —C(O)NR$_2$, or —C(O)OR.

In certain preferred embodiments, the subject compounds are represented by general structure 31:

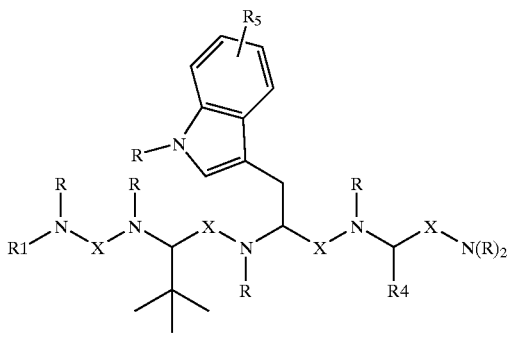

31 wherein

X represents, independently for each occurrence, —C(O)—, —C(R)$_2$—, —S(O)$_2$—, or —P(O)(OR)—;

R represents, independently for each occurrence, H, Me, lower alkyl, lower heteroalkyl, aryl, heteroaryl, aralkyl, or heteroaralkyl;

R1 is selected from the group comprising 2-, 3-, and 4-anisyl, dihalophenyl, 3,4-dichlorophenyl, 4-hydroxy-2,6-dimethylphenyl, 2-, 3-, and 4-trifluoromethylphenyl, 2-, 3-, and 4-thioanisyl;

R4 is selected from the group comprising 2-, 3-, and 4-halobenzyl, 2-, 3-, and 4-phenylbenzyl, benzyl, diphenylmethyl, triphenylmethyl, dihalobenzyl, 2-phenylethyl, 2-, 3-, and 4-pyridylmethyl;

$R_5$ is absent, or present between one and four times;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and the stereochemical configuration at any stereocenter of a compound represented by 31 is R, S, or a mixture of these configurations.

In assays based on opioid receptors from mammalian brain, compounds according to general structure 31 preferably have IC$_{50}$ values less than 10 $\mu$M against at least one subclass of opioid receptor, more preferably less than 5 $\mu$M, and most preferably less than 1 $\mu$M.

In certain preferred embodiments, the subject compounds are represented by general structure 32:

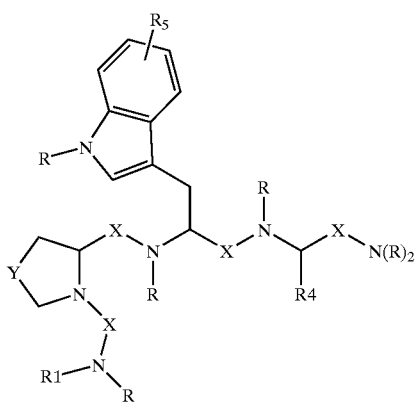

32 wherein

X represents, independently for each occurrence, —C(O)—, —C(R)$_2$—, —S(O)$_2$—, or —P(O)(OR)—;

Y represents [C(R)$_2$]$_p$, [O(CR$_2$)$_n$], or [S(CR$_2$)$_n$];

R represents, independently for each occurrence, H, Me, lower alkyl, lower heteroalkyl, aryl, heteroaryl, aralkyl, or heteroaralkyl;

R1 is selected from the group comprising 2-, 3-, and 4-anisyl, dihalophenyl, 3,4-dichlorophenyl, 4-hydroxy-2,6-dimethylphenyl, 2-, 3-, and 4-trifluoromethylphenyl, 2-, 3-, and 4-thioanisyl;

R4 is selected from the group comprising 2-, 3-, and 4-halobenzyl, 2-, 3-, and 4-phenylbenzyl, benzyl, diphenylmethyl, triphenylmethyl, dihalobenzyl, 2-phenylethyl, 2-, 3-, and 4-pyridylmethyl;

$R_5$ is absent, or present between one and four times;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 0 to 2 inclusive;

p is an integer in the range 1 to 4 inclusive; and the stereochemical configuration at any stereocenter of a compound represented by 32 is R, S, or a mixture of these configurations.

In assays based on opioid receptors from mammalian brain, compounds according to general structure 32 preferably have $IC_{50}$ values less than 10 μM against at least one subclass of opioid receptor, more preferably less than 5 μM, and most preferably less than 1 μM.

In certain preferred embodiments, the subject compounds are represented by general structure 33:

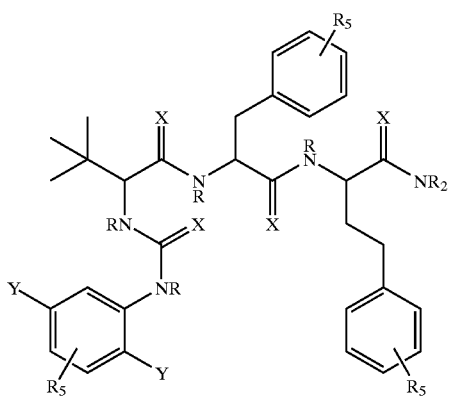

33 wherein

X represents, independently for each occurrence, O, S, $H_2$, or NR;

Y represents, independently for each occurrence, F, Cl, Br, or I;

R represents, independently for each occurrence, H, Me, lower alkyl, lower heteroalkyl, aryl, heteroaryl, aralkyl, or heteroaralkyl;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and the stereochemical configuration at any stereocenter of a compound represented by 33 may be R, S, or a mixture of these configurations.

In assays based on opioid receptors from mammalian brain, compounds according to general structure 33 preferably have $IC_{50}$ values less than 10 μM against at least one subclass of opioid receptor, more preferably less than 5 μM, and most preferably less than 1 μM.

In certain preferred embodiments, the subject compounds are represented by general structure 34:

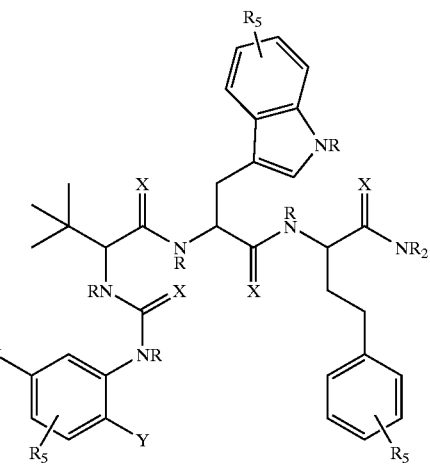

34 wherein

X represents, independently for each occurrence, O, S, $H_2$, or NR;

Y represents, independently for each occurrence, F, Cl, Br, or I;

R represents, independently for each occurrence, H, Me, lower alkyl, lower heteroalkyl, aryl, heteroaryl, aralkyl, or heteroaralkyl;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and the stereochemical configuration at any stereocenter of a compound represented by 34 may be R, S, or a mixture of these configurations.

In assays based on opioid receptors from mammalian brain, compounds according to general structure 34 preferably have $IC_{50}$ values less than 10 μM against at least one subclass of opioid receptor, more preferably less than 5 μM, and most preferably less than 1 μM.

In certain preferred embodiments, the subject compounds are represented by general structure 35:

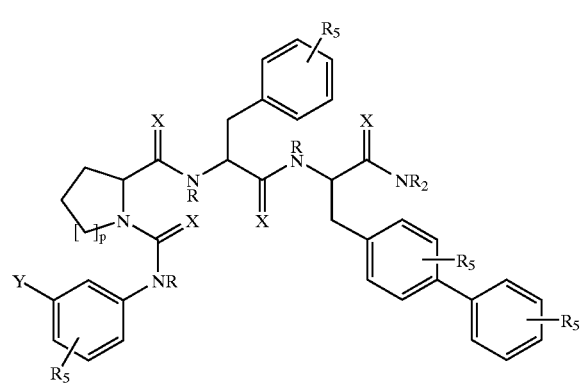

35 wherein

X represents, independently for each occurrence, O, S, $H_2$, or NR;

Y represents —OR;

R represents, independently for each occurrence, H, Me, lower alkyl, lower heteroalkyl, aryl, heteroaryl, aralkyl, or heteroaralkyl;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

p is an integer in the range 1 to 3 inclusive; and the stereochemical configuration at any stereocenter of a compound represented by 35 may be R, S, or a mixture of these configurations.

In assays based on opioid receptors from mammalian brain, compounds according to general structure 35 preferably have $IC_{50}$ values less than 10 $\mu$M against at least one subclass of opioid receptor, more preferably less than 5 $\mu$M, and most preferably less than 1 $\mu$M.

In certain preferred embodiments, the subject compounds are represented by general structure 36:

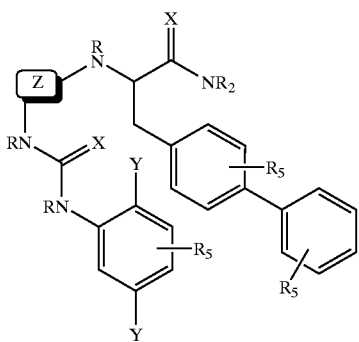

36 wherein

X represents, independently for each occurrence, O, S, $H_2$, or NR;

Y represents, independently for each occurrence, F, Cl, Br, or I;

Z represents a spatially-defined template, dipeptide peptidomimetic, or a linker group;

R represents, independently for each occurrence, H, Me, lower alkyl, lower heteroalkyl, aryl, heteroaryl, aralkyl, or heteroaralkyl;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

the stereochemical configuration at any stereocenter of a compound represented by 36 may be R, S, or a mixture of these configurations.

In assays based on opioid receptors from mammalian brain, compounds according to general structure 36 preferably have $IC_{50}$ values less than 10 $\mu$M against at least one subclass of opioid receptor, more preferably less than 5 $\mu$M, and most preferably less than 1 $\mu$M.

In preferred embodiments, the subject compounds are peptidomimetics of 1 or 2, comprising a 2-substituted piperazine moiety as a constrained amino acid analogue (for a report of the use of 2-substituted piperazine as constrained amino acid analogues, see: Williams et al. *J Med. Chem.* 1996, 39, 1345–1348). In certain preferred embodiments, compounds of this type are represented by general structure 37:

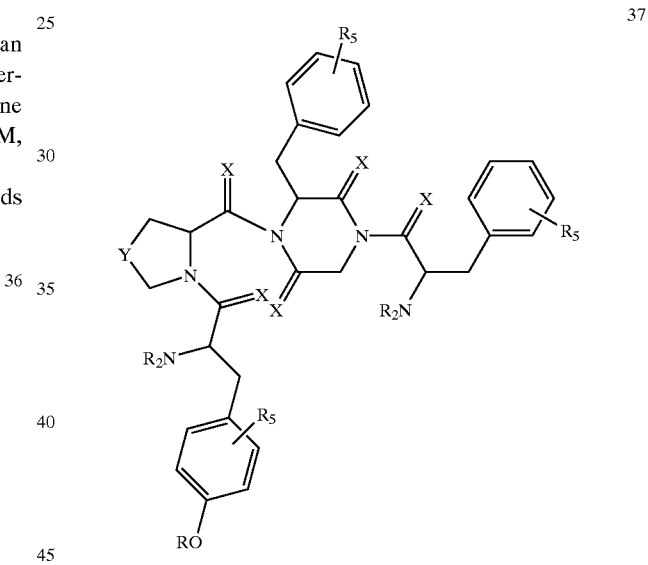

37 wherein

X represents, independently for each occurrence, O, S, $H_2$, or NR;

Y represents $[C(R)_2]_p$, $[O(CR_2)_n]$, or $[S(CR_2)_n]$;

R represents, independently for each occurrence, H, Me, lower alkyl, lower heteroalkyl, aryl, heteroaryl, aralkyl, or heteroaralkyl;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 0 to 2 inclusive;

p is an integer in the range 1 to 3 inclusive; and the stereochemical configuration at any stereocenter of a compound represented by 37 may be R, S, or a mixture of these configurations.

In assays based on opioid receptors from mammalian brain, compounds according to general structure 37 preferably have $IC_{50}$ values less than 10 μM against at least one subclass of opioid receptor, more preferably less than 5 μM, and most preferably less than 1 μM.

In additional preferred embodiments, the subject compounds are represented by general structure 38:

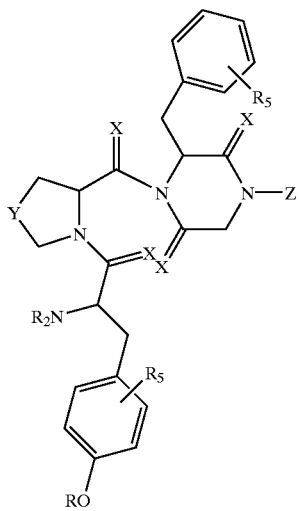

38 wherein

X represents, independently for each occurrence, O, S, $H_2$, or NR;

Y represents $[C(R)_2]_p$, $[O(CR_2)_n]$, or $[S(CR_2)_n]$;

Z represents —C(O)R, —S(O)$_2$R, or —C(O)NR$_2$;

R represents, independently for each occurrence, H, Me, lower alkyl, lower heteroalkyl, aryl, heteroaryl, aralkyl, or heteroaralkyl;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 0 to 2 inclusive;

p is an integer in the range 1 to 3 inclusive; and the stereochemical configuration at any stereocenter of a compound represented by 38 may be R, S, or a mixture of these configurations.

In assays based on opioid receptors from mammalian brain, compounds according to general structure 38 preferably have $IC_{50}$ values less than 10 μM against at least one subclass of opioid receptor, more preferably less than 5 μM, and most preferably less than 1 μM.

In certain preferred embodiments, the subject compounds are represented by general structure 39:

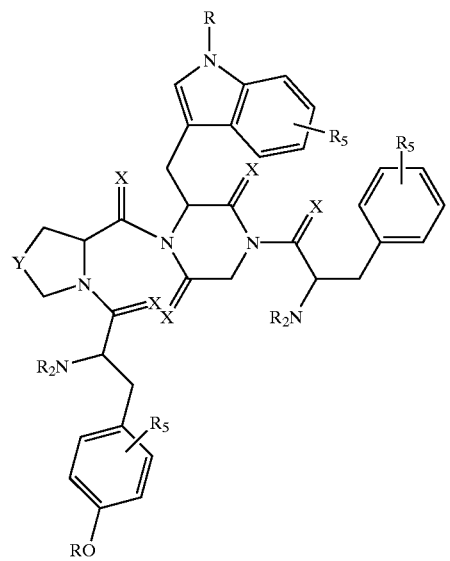

39 wherein

X represents, independently for each occurrence, O, S, $H_2$, or NR;

Y represents $[C(R)_2]_p$, $[O(CR_2)_n]$, or $[S(CR_2)_n]$;

R represents, independently for each occurrence, H, Me, lower alkyl, lower heteroalkyl, aryl, heteroaryl, aralkyl, or heteroaralkyl;

$R_5$, independently for each occurrence, is absent, or present between one and the maximum number of times permitted by the additional substitution on the relevant aromatic ring;

$R_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 0 to 2 inclusive;

p is an integer in the range 1 to 3 inclusive; and the stereochemical configuration at any stereocenter of a compound represented by 39 may be R, S, or a mixture of these configurations.

In assays based on opioid receptors from mammalian brain, compounds according to general structure 39 preferably have $IC_{50}$ values less than 10 μM against at least one subclass of opioid receptor, more preferably less than 5 μM, and most preferably less than 1 μM.

In additional preferred embodiments, the subject compounds are represented by general structure 40:

40

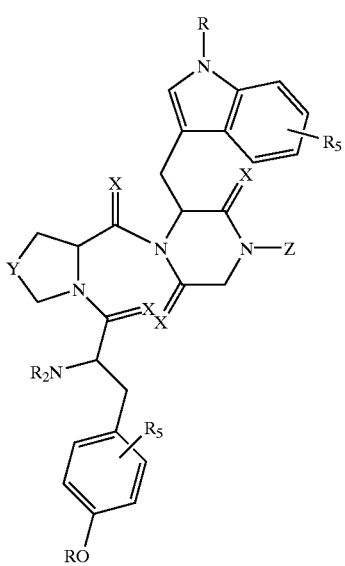

wherein

X represents, independently for each occurrence, O, S, H$_2$, or NR;

Y represents [C(R)$_2$]$_p$, [O(CR$_2$)$_n$], or [S(CR$_2$)$_n$];

Z represents —C(O)R, —S(O)$_2$R, or —C(O)NR$_2$;

R represents, independently for each occurrence, H, Me, lower alkyl, lower heteroalkyl, aryl, heteroaryl, aralkyl, or heteroaralkyl;

R$_5$, independently for each occurrence, is absent, or present between one and the maximum number of times permitted by the additional substitution on the relevant aromatic ring;

R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 0 to 2 inclusive;

p is an integer in the range 1 to 3 inclusive; and the stereochemical configuration at any stereocenter of a compound represented by 40 may be R, S, or a mixture of these configurations.

In assays based on opioid receptors from mammalian brain, compounds according to general structure 40 preferably have IC$_{50}$ values less than 10 μM against at least one subclass of opioid receptor, more preferably less than 5 μM, and most preferably less than 1 μM.

In additional preferred embodiments, the subject compounds are represented by general structure 41:

41

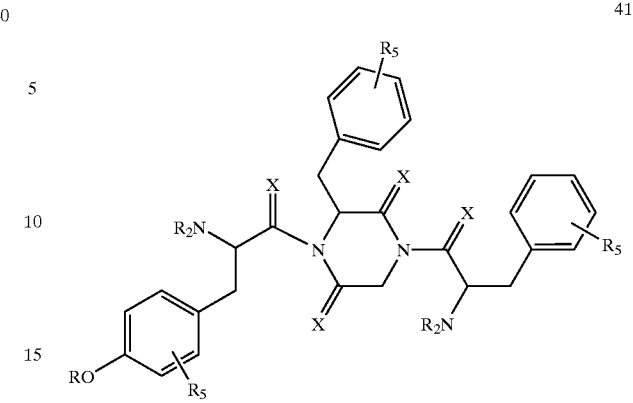

wherein

X represents, independently for each occurrence, O, S, H$_2$, or NR;

R represents, independently for each occurrence, H, Me, lower alkyl, lower heteroalkyl, aryl, heteroaryl, aralkyl, or heteroaralkyl;

R$_5$, independently for each occurrence, is absent, or present between one and the maximum number of times permitted by the additional substitution on the relevant aromatic ring;

R$_5$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and the stereochemical configuration at any stereocenter of a compound represented by 41 may be R, S, or a mixture of these configurations.

In assays based on opioid receptors from mammalian brain, compounds according to general structure 41 preferably have IC$_{50}$ values less than 10 μM against at least one subclass of opioid receptor, more preferably less than 5 μM, and most preferably less than 1 μM.

In additional preferred embodiments, the subject compounds are represented by general structure 42:

42 wherein

X represents, independently for each occurrence, O, S, H$_2$, or NR;

Z represents —C(O)R, —S(O)₂R, or —C(O)NR₂;

R represents, independently for each occurrence, H, Me, lower alkyl, lower heteroalkyl, aryl, heteroaryl, aralkyl, or heteroaralkyl;

R₅, independently for each occurrence, is absent, or present between one and the maximum number of times permitted by the additional substitution on the relevant aromatic ring;

R₅, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

the stereochemical configuration at any stereocenter of a compound represented by 42 may be R, S, or a mixture of these configurations.

In assays based on opioid receptors from mammalian brain, compounds according to general structure 42 preferably have IC₅₀ values less than 10 μM against at least one subclass of opioid receptor, more preferably less than 5 μM, and most preferably less than 1 μM.

In certain preferred embodiments, the subject compounds are represented by general structure 43:

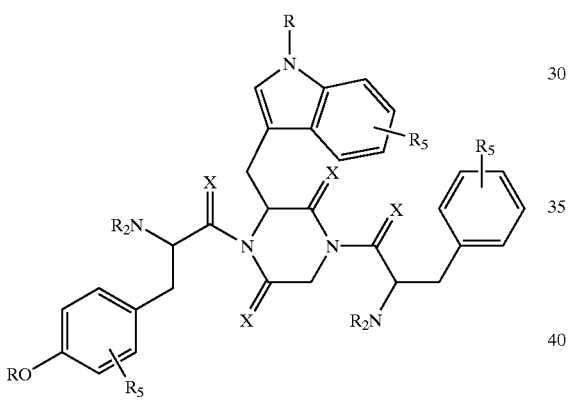

43 wherein

X represents, independently for each occurrence, O, S, H₂, or NR;

Y represents [C(R)₂]ₚ, O, or S;

R represents, independently for each occurrence, H, Me, lower alkyl, lower heteroalkyl, aryl, heteroaryl, aralkyl, or heteroaralkyl;

R₅, independently for each occurrence, is absent, or present between one and the maximum number of times permitted by the additional substitution on the relevant aromatic ring;

R₅, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

p is an integer in the range 1 to 4 inclusive; and the stereochemical configuration at any stereocenter of a compound represented by 43 may be R, S, or a mixture of these configurations.

In assays based on opioid receptors from mammalian brain, compounds according to general structure 43 preferably have IC₅₀ values less than 10 μM against at least one subclass of opioid receptor, more preferably less than 5 μM, and most preferably less than 1 μM.

In additional preferred embodiments, the subject compounds are represented by general structure 44:

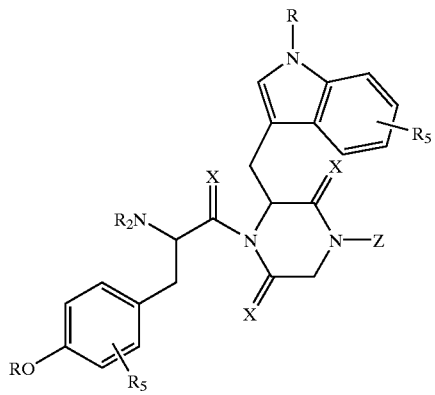

44 wherein

X represents, independently for each occurrence, O, S, H₂, or NR;

Z represents —C(O)R, —S(O)₂R, or —C(O)NR₂;

R represents, independently for each occurrence, H, Me, lower alkyl, lower heteroalkyl, aryl, heteroaryl, aralkyl, or heteroaralkyl;

R₅, independently for each occurrence, is absent, or present between one and the maximum number of times permitted by the additional substitution on the relevant aromatic ring;

R₅, when present, is selected independently for each occurrence from the set consisting of Me, lower alky, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and the stereochemical configuration at any stereocenter of a compound represented by 44 may be R, S, or a mixture of these configurations.

In assays based on opioid receptors from mammalian brain, compounds according to general structure 44 preferably have IC₅₀ values less than 10 μM against at least one subclass of opioid receptor, more preferably less than 5 μM, and most preferably less than 1 μM.

In additional preferred embodiments, the subject compounds are represented by general structure 45:

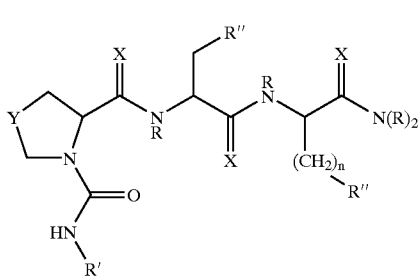

45 wherein

X independently for each occurrence represents O, S, H₂, or NR;

Y represents [C(R)$_2$]$_p$, [O(CR$_2$)$_m$], [S(CR$_2$)$_m$], [C(O)(CR$_2$)$_m$], [CH(OR)(CR$_2$)$_m$], or [CR(NR$_2$)(CR$_2$)$_m$];

R independently for each occurrence represents H, Me, lower alkyl, lower heteroalkyl, aryl, heteroaryl, aralkyl, heteroaralkyl, cycloalkyl, or heterocycloalkyl;

R' represents Me, lower alkyl, lower heteroalkyl, aryl, heteroaryl, aralkyl, heteroaralkyl, cycloalkyl, or heterocycloalkyl;

R" independently for each occurrence represents aryl, heteroaryl, aralkyl, or heteroaralkyl;

m is an integer in the range 0 to 2 inclusive;

p is an integer in the range 1 to 3 inclusive;

n is an integer in the range 0 to 3 inclusive; and the stereochemical configuration at any stereocenter of a compound represented by 45 is R, S, or a mixture of these configurations.

In certain embodiments, the compounds of the present invention are represented by general structure 45 and the attendant definitions, wherein X independently for each occurrence represents O or H$_2$.

In certain embodiments, the compounds of the present invention are represented by general structure 45 and the attendant definitions, wherein Y represents CR$_2$ or S.

In certain embodiments, the compounds of the present invention are represented by general structure 45 and the attendant definitions, wherein R independently for each occurrence represents H, Me, lower alkyl, lower heteroalkyl, aryl, heteroaryl, aralkyl, or heteroaralkyl.

In certain embodiments, the compounds of the present invention are represented by general structure 45 and the attendant definitions, wherein R" independently for each occurrence represents aryl or heteroaryl.

In certain embodiments, the compounds of the present invention are represented by general structure 45 and the attendant definitions, wherein X independently for each occurrence represents O or H$_2$; Y represents CR$_2$ or S; R independently for each occurrence represents H, Me, lower alkyl, lower heteroalkyl, aryl, heteroaryl, aralkyl, or heteroaralkyl; and R" independently for each occurrence represents aryl or heteroaryl.

In assays based on opioid receptors from mammalian brain, compounds according to general structure 45 preferably have IC$_{50}$ values less than 10 $\mu$M against at least one subclass of opioid receptor, more preferably less than 5 $\mu$M, and most preferably less than 1 $\mu$M.

In additional preferred embodiments, the subject compounds are represented by general structure 46:

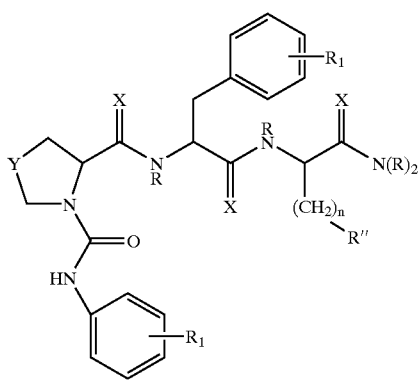

46 wherein

X independently for each occurrence represents O, S, H$_2$, or NR;

Y represents [C(R)$_2$]$_p$, [O(CR$_2$)$_m$], [S(CR$_2$)$_m$], [C(O)(CR$_2$)$_m$], [CH(OR)(CR$_2$)$_m$], or [CR(NR$_2$)(CR$_2$)$_m$];

R independently for each occurrence represents H, Me, lower alkyl, lower heteroalkyl, aryl, heteroaryl, aralkyl, heteroaralkyl, cycloalkyl, or heterocycloalkyl;

R" independently for each occurrence represents aryl, heteroaryl, aralkyl, or heteroaralkyl;

R$_1$, independently for each occurrence, is absent, or present between one and the maximum number of times permitted by the additional substitution on the relevant aromatic ring;

R$_1$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

p is an integer in the range 1 to 3 inclusive;

m is an integer in the range 0 to 2 inclusive;

n is an integer in the range 0 to 3 inclusive; and the stereochemical configuration at any stereocenter of a compound represented by 46 is R, S, or a mixture of these configurations.

In certain embodiments, the compounds of the present invention are represented by general structure 46 and the attendant definitions, wherein X independently for each occurrence represents O or H$_2$.

In certain embodiments, the compounds of the present invention are represented by general structure 46 and the attendant definitions, wherein Y represents CR$_2$ or S.

In certain embodiments, the compounds of the present invention are represented by general structure 46 and the attendant definitions, wherein R independently for each occurrence represents H, Me, lower alkyl, lower heteroalkyl, aryl, heteroaryl, aralkyl, or heteroaralkyl.

In certain embodiments, the compounds of the present invention are represented by general structure 46 and the attendant definitions, wherein R" represents aryl or heteroaryl.

In certain embodiments, the compounds of the present invention are represented by general structure 46 and the attendant definitions, wherein X independently for each occurrence represents O or H$_2$; Y represents CR$_2$ or S; R independently for each occurrence represents H, Me, lower alkyl, lower heteroalkyl, aryl, heteroaryl, aralkyl, or heteroaralkyl; and R" represents aryl or heteroaryl.

In assays based on opioid receptors from mammalian brain, compounds according to general structure 46 preferably have IC$_{50}$ values less than 10 $\mu$M against at least one subclass of opioid receptor, more preferably less than 5 $\mu$M, and most preferably less than 1 $\mu$M.

In additional preferred embodiments, the subject compounds are represented by general structure 47:

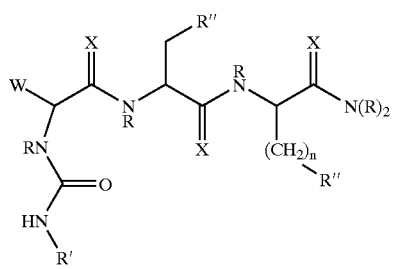

47 wherein

X independently for each occurrence represents O, S, H$_2$, or NR;

W represents Me or lower alkyl;

R independently for each occurrence represents H, Me, lower alkyl, lower heteroalkyl, aryl, heteroaryl, aralkyl, heteroaralkyl, cycloalkyl, or heterocycloalkyl;

R' represents Me, lower alkyl, lower heteroalkyl, aryl, heteroaryl, aralkyl, heteroaralkyl, cycloalkyl, or heterocycloalkyl;

R" independently for each occurrence represents aryl, heteroaryl, aralkyl, or heteroaralkyl;

n is an integer in the range 0 to 3 inclusive; and the stereochemical configuration at any stereocenter of a compound represented by 47 is R, S, or a mixture of these configurations.

In certain embodiments, the compounds of the present invention are represented by general structure 47 and the attendant definitions, wherein X independently for each occurrence represents O or H$_2$.

In certain embodiments, the compounds of the present invention are represented by general structure 47 and the attendant definitions, wherein W represents Me, Et, n-propyl, iso-propyl, or tert-butyl.

In certain embodiments, the compounds of the present invention are represented by general structure 47 and the attendant definitions, wherein R independently for each occurrence represents H, Me, lower alkyl, lower heteroalkyl, aryl, heteroaryl, aralkyl, or heteroaralkyl.

In certain embodiments, the compounds of the present invention are represented by general structure 47 and the attendant definitions, wherein R" independently for each occurrence represents aryl or heteroaryl.

In certain embodiments, the compounds of the present invention are represented by general structure 47 and the attendant definitions, wherein X independently for each occurrence represents O or H$_2$; W represents Me, Et, n-propyl, iso-propyl, or tert-butyl; R independently for each occurrence represents H, Me, lower alkyl, lower heteroalkyl, aryl, heteroaryl, aralkyl, or heteroaralkyl; and R" independently for each occurrence represents aryl or heteroaryl.

In assays based on opioid receptors from mammalian brain, compounds according to general structure 47 preferably have IC$_{50}$ values less than 10 µM against at least one subclass of opioid receptor, more preferably less than 5 µM, and most preferably less than 1 µM.

In additional preferred embodiments, the subject compounds are represented by general structure 48:

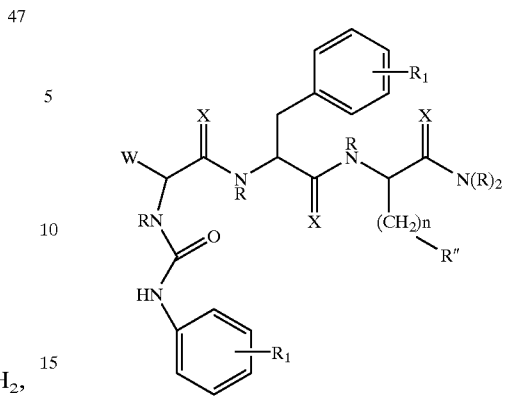

48 wherein

X independently for each occurrence represents O, S, H$_2$, or NR;

W represents Me or lower alkyl;

R independently for each occurrence represents H, Me, lower alkyl, lower heteroalkyl, aryl, heteroaryl, aralkyl, heteroaralkyl, cycloalkyl, or heterocycloalkyl;

R" independently for each occurrence represents aryl, heteroaryl, aralkyl, or heteroaralkyl;

R$_1$, independently for each occurrence, is absent, or present between one and the maximum number of times permitted by the additional substitution on the relevant aromatic ring;

R$_1$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 0 to 3 inclusive; and the stereochemical configuration at any stereocenter of a compound represented by 48 is R, S, or a mixture of these configurations.

In certain embodiments, the compounds of the present invention are represented by general structure 48 and the attendant definitions, wherein X independently for each occurrence represents O or H$_2$.

In certain embodiments, the compounds of the present invention are represented by general structure 48 and the attendant definitions, wherein W represents Me, Et, n-propyl, iso-propyl, or tert-butyl.

In certain embodiments, the compounds of the present invention are represented by general structure 48 and the attendant definitions, wherein R independently for each occurrence represents H, Me, lower alkyl, lower heteroalkyl, aryl, heteroaryl, aralkyl, or heteroaralkyl.

In certain embodiments, the compounds of the present invention are represented by general structure 48 and the attendant definitions, wherein R" independently for each occurrence represents aryl or heteroaryl.

In certain embodiments, the compounds of the present invention are represented by general structure 48 and the attendant definitions, wherein X independently for each occurrence represents O or H$_2$; W represents Me, Et, n-propyl, iso-propyl, or tert-butyl; R independently for each occurrence represents H, Me, lower alkyl, lower heteroalkyl, aryl, heteroaryl, aralkyl, or heteroaralkyl; and R" independently for each occurrence represents aryl or heteroaryl.

In assays based on opioid receptors from mammalian brain, compounds according to general structure 48 preferably have IC$_{50}$ values less than 10 μM against at least one subclass of opioid receptor, more preferably less than 5 μM, and most preferably less than 1 μM.

In additional preferred embodiments, the subject compounds are represented by general structure 49:

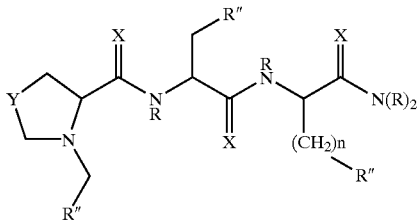

49 wherein

X independently for each occurrence represents O, S, H$_2$, or NR;

Y represents [C(R)$_2$]$_p$, [O(CR$_2$)$_m$], [S(CR$_2$)$_m$], [C(O)(CR$_2$)$_m$], [CH(OR)(CR$_2$)$_m$], or [CR(NR$_2$)(CR$_2$)$_m$];

R independently for each occurrence represents H, Me, lower alkyl, lower heteroalkyl, aryl, heteroaryl, aralkyl, heteroaralkyl, cycloalkyl, or heterocycloalkyl;

R" independently for each occurrence represents aryl, heteroaryl, aralkyl, or heteroaralkyl;

p is an integer in the range 1 to 3 inclusive;

m is an integer in the range 0 to 2 inclusive;

n is an integer in the range 0 to 3 inclusive; and the stereochemical configuration at any stereocenter of a compound represented by 49 is R, S, or a mixture of these configurations.

In certain embodiments, the compounds of the present invention are represented by general structure 49 and the attendant definitions, wherein X independently for each occurrence represents O or H$_2$.

In certain embodiments, the compounds of the present invention are represented by general structure 49 and the attendant definitions, wherein Y represents CR$_2$ or S.

In certain embodiments, the compounds of the present invention are represented by general structure 49 and the attendant definitions, wherein R independently for each occurrence represents H, Me, lower alkyl, lower heteroalkyl, aryl, heteroaryl, aralkyl, or heteroaralkyl.

In certain embodiments, the compounds of the present invention are represented by general structure 49 and the attendant definitions, wherein R" independently for each occurrence represents aryl or heteroaryl.

In certain embodiments, the compounds of the present invention are represented by general structure 49 and the attendant definitions, wherein X independently for each occurrence represents O or H$_2$; Y represents CR$_2$ or S; R independently for each occurrence represents H, Me, lower alkyl, lower heteroalkyl, aryl, heteroaryl, aralkyl, or heteroaralkyl; and R" independently for each occurrence represents aryl or heteroaryl.

In assays based on opioid receptors from mammalian brain, compounds according to general structure 49 preferably have IC$_{50}$ values less than 10 μM against at least one subclass of opioid receptor, more preferably less than 5 μM, and most preferably less than 1 μM.

In additional preferred embodiments, the subject compounds are represented by general structure 50:

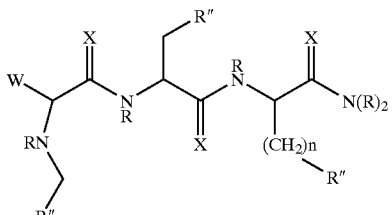

50 wherein

X independently for each occurrence represents O, S, H$_2$, or NR;

W represents Me or lower alkyl;

R independently for each occurrence represents H, Me, lower alkyl, lower heteroalkyl, aryl, heteroaryl, aralkyl, heteroaralkyl, cycloalkyl, or heterocycloalkyl;

R" independently for each occurrence represents aryl, heteroaryl, aralkyl, or heteroaralkyl;

n is an integer in the range 0 to 3 inclusive; and the stereochemical configuration at any stereocenter of a compound represented by 50 is R, S, or a mixture of these configurations.

In certain embodiments, the compounds of the present invention are represented by general structure 50 and the attendant definitions, wherein X independently for each occurrence represents O or H$_2$.

In certain embodiments, the compounds of the present invention are represented by general structure 50 and the attendant definitions, wherein W represents Me, Et, n-propyl, iso-propyl, or tert-butyl.

In certain embodiments, the compounds of the present invention are represented by general structure 50 and the attendant definitions, wherein R independently for each occurrence represents H, Me, lower alkyl, lower heteroalkyl, aryl, heteroaryl, aralkyl, or heteroaralkyl.

In certain embodiments, the compounds of the present invention are represented by general structure 50 and the attendant definitions, wherein R" independently for each occurrence represents aryl or heteroaryl.

In certain embodiments, the compounds of the present invention are represented by general structure 50 and the attendant definitions, wherein X independently for each occurrence represents O or H$_2$; W represents Me, Et, n-propyl, iso-propyl, or tert-butyl; R independently for each occurrence represents H, Me, lower alkyl, lower heteroalkyl, aryl, heteroaryl, aralkyl, or heteroaralkyl; and R" independently for each occurrence represents aryl or heteroaryl.

In assays based on opioid receptors from mammalian brain, compounds according to general structure 50 preferably have IC$_{50}$ values less than 10 μM against at least one subclass of opioid receptor, more preferably less than 5 μM, and most preferably less than 1 μM.

In additional preferred embodiments, the subject compounds are represented by general structure 51:

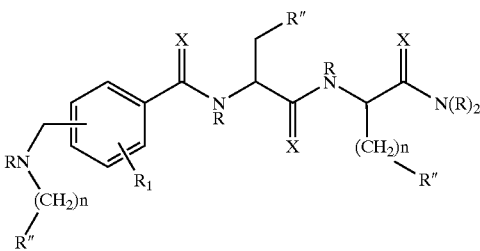

wherein
- X independently for each occurrence represents O, S, H$_2$, or NR;
- R independently for each occurrence represents H, Me, lower alkyl, lower heteroalkyl, aryl, heteroaryl, aralkyl, heteroaralkyl, cycloalkyl, or heterocycloalkyl;
- R" independently for each occurrence represents aryl, heteroaryl, aralkyl, or heteroaralkyl;
- one instance of the —(CH$_2$)N(R)—(CH$_2$)$_n$R" substitutent is present on the phenyl moiety explicitly depicted in 51; and said substituent has either a meta or para relationship to the —C(X)-substituent on said phenyl moiety;
- R$_1$, independently for each occurrence, is absent, or present between one and the maximum number of times permitted by the additional substitution on the relevant aromatic ring;
- R$_1$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;
- n independently for each occurrence is an integer in the range 0 to 3 inclusive; and
- the stereochemical configuration at any stereocenter of a compound represented by 51 is R, S, or a mixture of these configurations.

In certain embodiments, the compounds of the present invention are represented by general structure 51 and the attendant definitions, wherein X independently for each occurrence represents O or H$_2$.

In certain embodiments, the compounds of the present invention are represented by general structure 51 and the attendant definitions, wherein R independently for each occurrence represents H, Me, lower alkyl, lower heteroalkyl, aryl, heteroaryl, aralkyl, or heteroaralkyl.

In certain embodiments, the compounds of the present invention are represented by general structure 51 and the attendant definitions, wherein R" independently for each occurrence represents aryl or heteroaryl.

In certain embodiments, the compounds of the present invention are represented by general structure 51 and the attendant definitions, wherein R$_1$ is absent.

In certain embodiments, the compounds of the present invention are represented by general structure 51 and the attendant definitions, wherein X independently for each occurrence represents O or H$_2$; R independently for each occurrence represents H, Me, lower alkyl, lower heteroalkyl, aryl, heteroaryl, aralkyl, or heteroaralkyl; R" independently for each occurrence represents aryl or heteroaryl; and R$_1$ is absent.

In assays based on opioid receptors from mammalian brain, compounds according to general structure 51 preferably have IC$_{50}$ values less than 10 μM against at least one subclass of opioid receptor, more preferably less than 5 μM, and most preferably less than 1 μM.

In additional preferred embodiments, the subject compounds are represented by general structure 52:

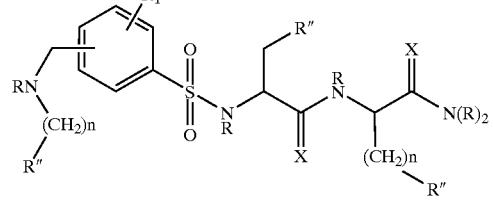

wherein
- X independently for each occurrence represents O, S, H$_2$, or NR;
- R independently for each occurrence represents H, Me, lower alkyl, lower heteroalkyl, aryl, heteroaryl, aralkyl, heteroaralkyl, cycloalkyl, or heterocycloalkyl;
- R" independently for each occurrence represents aryl, heteroaryl, aralkyl, or heteroaralkyl;
- one instance of the —(CH$_2$)N(R)—(CH$_2$)$_n$R" substitutent is present on the phenyl moiety explicitly depicted in 51; and said substituent has either a meta orpara relationship to the —S(O)$_2$-substituent on said phenyl moiety;
- R$_1$, independently for each occurrence, is absent, or present between one and the maximum number of times permitted by the additional substitution on the relevant aromatic ring;
- R$_1$, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;
- n independently for each occurrence is an integer in the range 0 to 3 inclusive; and
- the stereochemical configuration at any stereocenter of a compound represented by 52 is R, S, or a mixture of these configurations.

In certain embodiments, the compounds of the present invention are represented by general structure 52 and the attendant definitions, wherein X independently for each occurrence represents O or H$_2$.

In certain embodiments, the compounds of the present invention are represented by general structure 52 and the attendant definitions, wherein R independently for each occurrence represents H, Me, lower alkyl, lower heteroalkyl, aryl, heteroaryl, aralkyl, or heteroaralkyl.

In certain embodiments, the compounds of the present invention are represented by general structure 52 and the attendant definitions, wherein R" independently for each occurrence represents aryl or heteroaryl.

In certain embodiments, the compounds of the present invention are represented by general structure 52 and the attendant definitions, wherein R$_1$ is absent.

In certain embodiments, the compounds of the present invention are represented by general structure 52 and the attendant definitions, wherein X independently for each occurrence represents O or H$_2$; R independently for each occurrence represents H, Me, lower alkyl, lower heteroalkyl, aryl, heteroaryl, aralkyl, or heteroaralkyl; R" independently for each occurrence represents aryl or heteroaryl; and $R_1$ is absent.

In assays based on opioid receptors from mammalian brain, compounds according to general structure 52 preferably have $IC_{50}$ values less than 10 μM against at least one subclass of opioid receptor, more preferably less than 5 μM, and most preferably less than 1 μM.

III. Exemplary Synthetic Schemes

The subject compounds can be prepared readily from individual components by employing the standard methods of peptide synthesis, heterocyclic chemistry, and the like. These reactions are carried out under relatively mild conditions and tolerate a wide range of "spectator" functionality. A few illustrative examples are shown below.

a. Synthesis of a p-Aminobenzoic Acid-Based Peptidomimetic b. Synthesis of a Piperazic Acid-Containing Peptidomimetic c. Synthesis of a 2-Substituted Piperazine-Containing Peptidomimetic

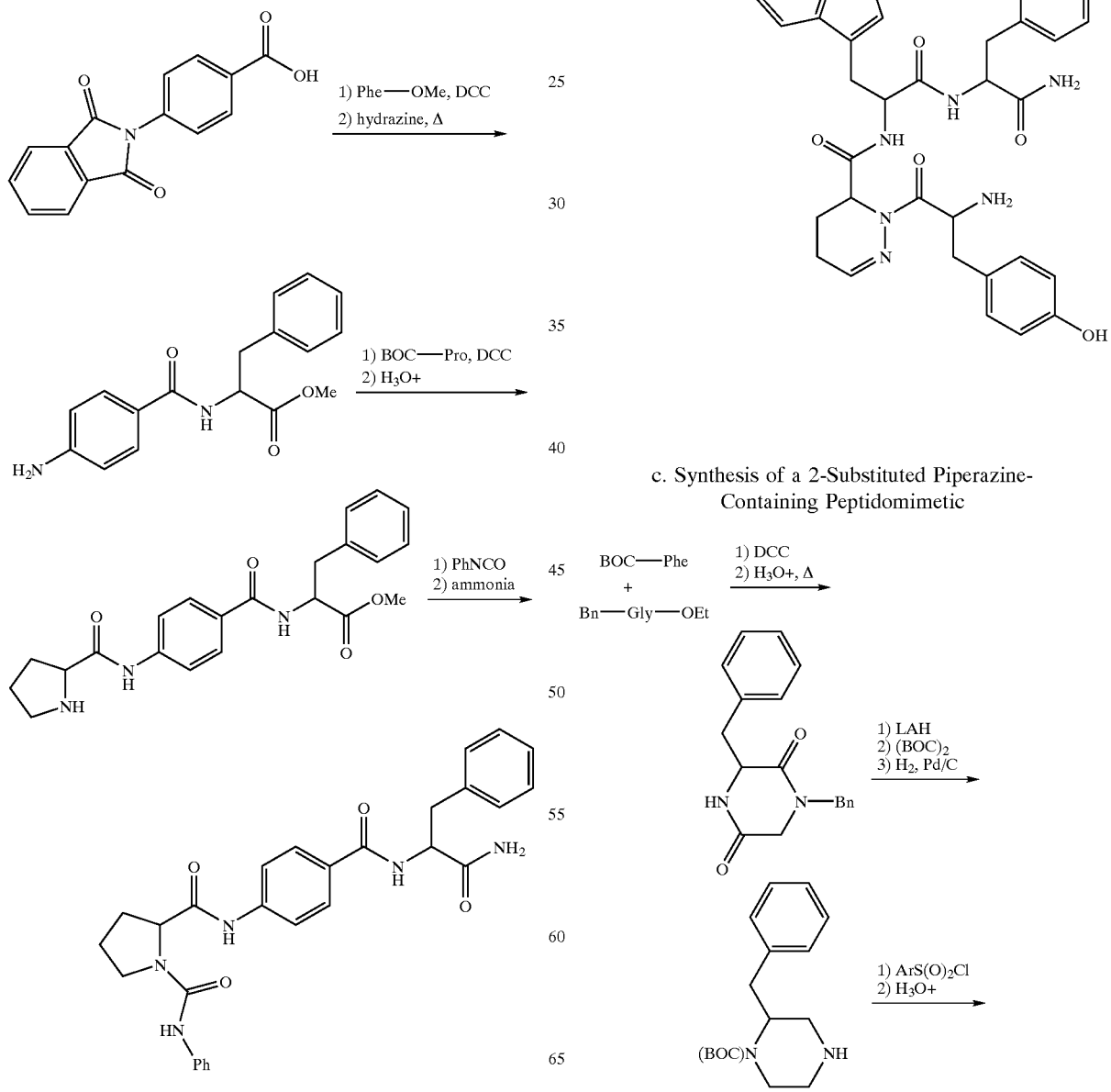

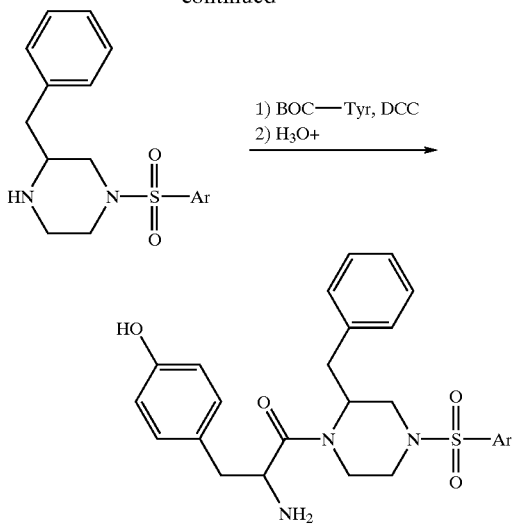

IV. Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject co,pounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Ore., U.S.A., 1977).

V. Combinatorial Libraries

High throughput screening of natural products and fermentation broths has resulted in the discovery of several new drugs. At present, generation and screening of chemical diversity is being utilized extensively as a major technique for the discovery of lead compounds, and this is certainly a major fundamental advance in the area of drug discovery. Peptide libraries present potential for producing millions of new peptide compounds for screening at a reasonable cost thus eliminating the time consuming, laborious and expensive procedures involved in the isolation, characterization, and synthesis of peptides obtained from natural sources (fermentation products) or conventional synthetic methods. It is not unusual to generate and screen tens of millions of peptides from a "peptide library". The combinatorial method permits incorporation of D-amino acid or unnatural amino acid residues as well as specific secondary structures.

The compounds of the present invention, particularly libraries of variants having various representative classes of substituents, can be generated using combinatorial chemistry (see, for example, PCT WO 94/08051) and screened rapidly in high throughput assays in order to identify potential lead compounds for inhibiting the growth of a particular bacterial species. For instance, simple turbidimetric assays (e.g. measuring the $A_{600}$ of a culture) can be used to assess the effects of a compound on a particular bacterial strain.

The subject compounds readily lend themselves to the creation of combinatorial libraries of ligands and the like. A combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the amino acids used in the combinatorial reactions can be diverse in terms of their sidechains or absolute configuration, e.g., a variegation in terms of the level of functionality in the sidechain, or the use of both enantiomers of a chiral amino acid.

A variety of techniques are available in the art for generating combinatorial libraries of small organic molecules such as the subject ligands. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject ligands can be synthesized and screened for particular activity or property.

In an exemplary embodiment, a library of candidate ligand diversomers can be synthesized utilizing a scheme adapted to the techniques described in the Still et al. PCT publication WO 94/08051, e.g., being linked to a polymer bead by a hydrolyzable or photolyzable group e.g., located at one of the positions of the candidate ligands or a substituent of a synthetic intermediate. According to the Still et al. technique, the library is synthesized on a set of beads, each bead including a set of tags identifying the particular diversomer on that bead. Detailed descriptions of a number of combinatorial methodologies are provided below.

A) Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a ligand library can be irradiated in a MALDI step in order to release the ligand from the matrix, and ionize the ligand for MS analysis.

B) Multipin Synthesis

The ligand library of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of ligands per week using the multipin method, and the tethered ligands may be reused in many assays. Appropriate linker moieties can also been appended to the pins so that the ligands may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of ligands can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the ligand library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where ligand synthesis occurs on resin sealed inside porous polypropylene bags (Houghten et al. (1986) *PNAS* 82:5131–5135). Substituents are coupled to the ligand-bearing resins by placing the bags in appropriate reaction solutions, while all common steps such as resin washing and deprotection are performed simultaneously in one reaction vessel. At the end of the synthesis, each bag contains a single ligand moiety.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each ligand is precisely known; hence, its interactions with other molecules can be directly assessed.

In a light-directed chemical synthesis, the products depend on the pattern of illumination and on the order of addition of reactants. By varying the lithographic patterns, many different sets of test ligands can be synthesized simultaneously; this characteristic leads to the generation of many different masking strategies.

E) Encoded Combinatorial Libraries

In yet another embodiment, the subject method utilizes a ligand library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) PNAS 89:5381–5383), and an example of such a library appeared the following year (Needles et al. (1993) PNAS 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, ligand libraries can be derived for use in the subject method, where the oligonucleotide sequence of the tag identifies the sequential combinatorial reactions that a particular bead underwent, and therefore provides the identity of the ligand on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test ligand library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529–2531), orthogonality in synthesis is achieved by employing acid-labile protection for the coding strand and base-labile protection for the ligand strand.

In an alternative approach (Nikolaiev et al. (1993) Pept Res 6:161–170), branched linkers are employed so that the coding unit and the test ligand can both be attached to the same functional group on the resin. In one embodiment, a cleavable linker can be placed between the branch point and the bead so that cleavage releases a molecule containing both code and the ligand (Ptek et al. (1991) Tetrahedron Lett 32:3891–3894). In another embodiment, the cleavable linker can be placed so that the test ligand can be selectively separated from the bead, leaving the code behind. This last construct is particularly valuable because it permits screening of the test ligand without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test ligand library employs a set of non-sequencable electrophoric tagging molecules that are used as a binary code (Ohlmeyer et al. (1993) PNAS 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the ligand would be attached to the solid support via the photocleavable linker and the tag is attached through a catechol ether linker via carbene insertion into the bead matrix (Nestler et al. (1994) J Org Chem 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027–6031) and provide guidance for generating the subject ligand library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, ligands are partially detached and transferred to assay plates; third, a metal binding assay identifies the active wells; fourth, the corresponding beads are rearrayed singly into new microtiter plates; fifth, single active ligands are identified; and sixth, the structures are decoded.

Exemplification

The invention now being generally described, it will be more readily understood by reference to the following examples, which are included merely for purposes of illustration of certain aspects and embodiments of the present invention, and are not intended to limit the invention.

Various abbreviations pertaining to the Examples, including abbreviations for natural and unnatural amino acids, are collected in the section above entitled "Definitions."

EXAMPLE 1

Non-Selective Opiate Radioligand Binding Assay

This assay measures binding of [$^3$H]Naloxone to opiate receptors. Whole brain (except cerebellum) membranes of male Wistar derived rats weighing 175±25 g are prepared in Tris-HCl pH 7.7 buffer using standard techniques. A 7.5 mg aliquot of membrane is incubated with 1 nM [$^3$H]Naloxone for 40 minutes at 25° C. Non-specific binding is estimated in the presence of 1 μM Naloxone. Membranes are filtered and washed 3 times, and the filters are counted to determine [$^3$H]Naloxone specifically bound. Compounds are screened at 1 μM.

EXAMPLE 2

Human Opiate μ Radioligand Binding Assay

This assay measures binding of [$^3$H]Diprenorphine (DPN) to human opiate 1 receptors. CHO-K$_1$ cells stably transfected with a plasmid encoding the human opiate μ receptor are used to prepare membranes in modified Tris-HCl pH 7.4 buffer using standard techniques. An 11 μg aliquot of membrane is incubated with 0.6 nM [$^3$H]DPN for 2.5 hours at 25° C. Nonspecific binding is estimated in the presence of 10 μM naloxone. Membranes are filtered and washed 3 times, and the filters are counted to determine [$^3$H]DPN specifically bound. Compounds are screened at 1 μM.

EXAMPLE 3

Human Opiate κ Radioligand Binding Assay

This assay measures binding of [$^3$H]Diprenorphine (DPN) to human opiate κ receptors. CHO cells stably transfected with a plasmid encoding the human opiate K receptor are used to prepare membranes in modified Tris-HCl pH 7.4 buffer using standard techniques. A 30 μg aliquot of membrane is incubated with 0.6 nM [$^3$H]DPN for 60 minutes at 25° C. Nonspecific binding is estimated in the presence of 10 μM naloxone. Membranes are filtered and washed 3 times, and the filters are counted to determine [$^3$H]DPN specifically bound. Compounds are screened at 1 μM.

EXAMPLE 4

Human Opiate δ Radioligand Binding Assay

This assay measures binding of [$^3$H]Naltrindole to human opiate δ receptors. CHO cells stably transfected with a plasmid encoding the human opiate δ receptor are used to prepare membranes in modified Tris-HCl pH 7.4 buffer using standard techniques. A 0.9 μg aliquot of membrane is incubated with 0.9 nM [$^3$H]Naltrindole for 120 minutes at 25° C. Nonspecific binding is estimated in the presence of 10 μM naloxone. Membranes are filtered and washed 3 times, and the filters are counted to determine [$^3$H]Naltrindole specifically bound. Compounds are screened at 1 μM.

EXAMPLE 5

Assays for μ-Opioid Receptor Agonism or Antagonism

A segment of ileum obtained from Duncan Hartley-derived male or female guinea pigs weighing 325±25 grams was used. The tissue was placed under 0.5 g tension in a 10 mL bath containing Krebs solution, pH 7.4 at 32° C., and subjected to field stimulation (70% of maximum voltage, 0.1 Hz, 0.3 msec). If within five minutes, the test substance (at 30 micromolar) induced reduction of isometrically recorded contraction by 50 percent or more (≧50%), relative to 0.03 micromolar DAMGO response, opioid-γ receptor agonist activity was indicated. At a test substance concentration where no significant agonist activity was seen, the ability to inhibit DAMGO-induced relaxant response by 50 percent or more (≧50%) indicated opioid-μ receptor antagonist activity. Each concentration was tested on two separate preparations.

EXAMPLE 6

Synthesis of Endomorphin 2 Analogue 57 (See FIG. 4)

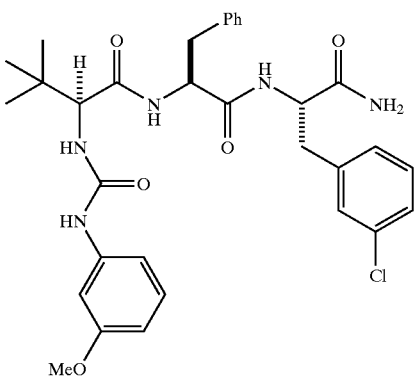

Step 1—Attachment of 3-Chlorophenylalanine to the Solid Support

N-Fmoc Rink Amide resin (1.0 g, 0.8 mmole g$^{-1}$) was treated with 25% piperidine in DMF (v/v), washed successively with DMF, MeOH, and DCM (three washes), and dried in vacuo. Fmoc-L-3-CPA was added to a solution of PyBOP (5 equiv.) in 0.1 M NMM in DMF (10 mL). This solution was then added to the dried resin, and the resin slurry was agitated for 3 hours on an orbital shaker. The resin was then washed successively with DMF, MeOH, and DCM (three washes).

Step 2—Synthesis of the Dipeptide on the Solid Support

Resin-bound Fmoc-L-3-CPA-resin was treated with 25% piperidine in DMF (v/v), washed successively with DMF, MeOH, and DCM (three washes), and dried in vacuo. Fmoc-L-Phe was added to a solution of PyBOP (5 equiv.) in 0.1 M NMM in DMF (10 mL). This solution was then added to the dried resin, and the resin slurry was agitated for 3 hours on an orbital shaker, and then washed successively with DMF, MeOH, and DCM (three times).

Step 3—Synthesis of the Tripeptide on the Solid Support

Resin-bound Fmoc-Phe-L-3-CPA-resin was treated with 25% piperidine in DMF (v/v), washed successively with DMF, MeOH, and DCM (three washes), and dried in vacuo. Fmoc-L-t-Leu was added to a solution of PyBOP (5 equiv.) in 0.1 M NMM in DMF (10 mL). This solution was then added to the dried resin, and the resin slurry was agitated for 3 hours on an orbital shaker, and then washed successively with DMF, MeOH, and DCM (three times).

Step 4—Synthesis of the Tetrapeptide on the Solid Support

Resin-bound Fmoc-t-Leu-Phe-L-3-CPA-resin was treated with 25% piperidine in DMF (v/v), washed successively with DMF, MeOH, and DCM (three times), and dried in vacuo. To the dried resin was added a solution of 3-methoxyphenyl isocyanate (0.119 g, 0.8 mmole). The resin slurry was agitated for 18 hours on an orbital shaker, and then washed successively with DMF, MeOH, and DCM (three times).

Step 5—Cleavage of Tetrapeptide (57) from the Solid Support

Resin-bound compound 57 was cleaved from the solid support by agitating the resin with 50% TFA in DCM (v/v) for 30 min followed by filtration and removal of the solvent in vacuo.

EXAMPLE 7

Synthesis of Rink resin-bound Fmoc-BIP

N-Fmoc protected Rink Amide resin (40.0 g, 0.8 mmole $g^{-1}$) was suspended in a solution (400 ml) of 25% piperidine in DMF (v/v) and agitated for 1 hour on an orbital shaker. The solution was removed by filtration, and the resin was washed successively with DMF, MeOH, and DCM (three washes) and then dried in vacuo. Fmoc-L-BIP (41.6 rnmole, 10 equiv.) was added to a solution of PyBOP® (10 equiv.) in 0.1M NMM in anhydrous DMF (50 ml). This solution was then added to a portion of the dried resin (5.2 g), and the resin slurry was agitated for 3 hours on an orbital shaker. The solution was removed by filtration, and the resin was washed successively with DMF, MeOH, and DCM (three washes) and then dried in vacuo.

EXAMPLE 8

Synthesis of Rink resin-bound Fmoc-2-FPA

This product was synthesized according to the procedure described in Example 7, utilizing 10 equiv. of Fmoc-L-2-FPA.

EXAMPLE 9

Synthesis of Rink resin-bound Fmoc-3-FPA

This product was synthesized according to the procedure described in Example 7, utilizing 10 equiv. of Fmoc-L-3-FPA.

EXAMPLE 10

Synthesis of Rink resin-bound Fmoc-4-FPA

This product was synthesized according to the procedure described in Example 7, utilizing 10 equiv. of Fmoc-L-4-FPA.

EXAMPLE 11

Synthesis of Rink resin-bound Fmoc-3-CPA

This product was synthesized according to the procedure described in Example 7, utilizing 10 equiv. of Fmoc-L-3-CPA.

EXAMPLE 12

Synthesis of Rink resin-bound Fmoc-3,4-DCP

This product was synthesized according to the procedure described in Example 7, utilizing 10 equiv. of Fmoc-L-3,4-DCP.

EXAMPLE 13

Synthesis of Rink resin-bound Fmoc-4-BPA

This product was synthesized according to the procedure described in Example 7, utilizing 10 equiv. of Fmoc-L-4-BPA.

EXAMPLE 14

Synthesis of Rink resin-bound Fmoc-HPA

This product was synthesized according to the procedure described in Example 7, utilizing 10 equiv. of Fmoc-L-HPA.

EXAMPLE 15

Synthesis of Rink resin-bound Fmoc-1-NAL

This product was synthesized according to the procedure described in Example 7, utilizing 10 equiv. of Fmoc-L-1-NAL.

EXAMPLE 16

Synthesis of Rink resin-bound Fmoc-2-NAL

This product was synthesized according to the procedure described in Example 7, utilizing 10 equiv. of Fmoc-L-2-NAL.

EXAMPLE 17

Synthesis of Rink resin-bound Fmoc-4-TAZ

This product was synthesized according to the procedure described in Example 7, utilizing 10 equiv. of Fmoc-L-4-TAZ.

EXAMPLE 18

Synthesis of Rink resin-bound Fmoc-3-PAL

This product was synthesized according to the procedure described in Example 7, utilizing 10 equiv. of Fmoc-L-3-PAL.

EXAMPLE 19

Synthesis of Rink resin-bound Fmoc-DIP

This product was synthesized according to the procedure described in Example 7, utilizing 10 equiv. of Fmoc-L-DIP.

EXAMPLE 20

Synthesis of Rink resin-bound Fmoc-BAL

This product was synthesized according to the procedure described in Example 7, utilizing 10 equiv. of Fmoc-L-BAL.

EXAMPLE 21

Synthesis of Rink resin-bound Fmoc-Phe-BIP

Rink resin-bound Fmoc-L-BIP (5.5 g) was suspended in a solution (50 ml) of 25% piperidine in DMF (v/v) and agitated for 1 hour on an orbital shaker. The solution was removed by filtration, and the resin was washed successively with DMF, MeOH, and DCM (three washes) and then dried in vacuo. Fmoc-L-Phe (38.4 mmole, 10 equiv.) was added to a solution of PyBOP® (10 equiv.) in 0.1M NMM in anhydrous DMF (50 ml). This solution was then added to the dried resin (4.8 g), and the resin slurry was agitated for 3 hours on an orbital shaker. The solution was removed by filtration, and the resin was then washed successively with DMF, MeOH, and DCM (three washes) and then dried in vacuo.

EXAMPLE 22

Synthesis of Rink resin-bound Fmoc-Phe-Xaa

Rink resin-bound Fmoc-Phe-Xaa was synthesized according to the procedure described in Example 21, utilizing Rink resin-bound Fmoc-Xaa.

EXAMPLE 23

Synthesis of Rink resin-bound Fmoc-Pro-Phe-BIP

Rink resin-bound Fmoc-Phe-BIP (2.5 g) was suspended in a solution (25 ml) of 25% piperidine in DMF (v/v) and agitated for 1 hour on an orbital shaker. The solution was removed by filtration, and the resin was then washed successively with DMF, MeOH, and DCM (three washes) and then dried in vacuo. Fmoc-L-Pro (2.0 mmole, 10 equiv.) was added to a solution of PyBOP® (10 equiv.) in 0.1M NMM in anhydrous DMF (25 ml). This solution was then added to the dried resin, and the resin slurry was agitated for 3 hours on an orbital shaker. The solution was removed by filtration, and the resin was then washed successively with DMF, MeOH, and DCM (three washes) and then dried in vacuo.

EXAMPLE 24

Synthesis of Rink resin-bound Fmoc-Thz-Phe-Xaa

Rink resin-bound Fmoc-Thz-Phe-Xaa was synthesized according to the procedure described in Example 23, utilizing 10 equiv. of Fmoc-L-Thz and Rink resin-bound Fmoc-Phe-Xaa.

EXAMPLE 25

Synthesis of Rink resin-bound Fmoc-tert-Leu-Phe-Xaa

Rink resin-bound Fmoc-tert-Leu-Phe-Xaa was synthesized according to the procedure described in Example 23, utilizing 10 equiv. of Fmoc-L-tert-Leu and Rink resin-bound Fmoc-Phe-Xaa.

EXAMPLE 26

Synthesis of Rink resin-bound Fmoc-Pip-Phe-Xaa

Rink resin-bound Fmoc-Pip-Phe-Xaa was synthesized according to the procedure described in Example 23, utilizing 10 equiv. of Fmoc-L-Pip and Rink resin-bound Fmoc-Phe-Xaa.

EXAMPLE 27

Synthesis of Rink resin-bound Fmoc-Tic-Phe-Xaa

Rink resin-bound Fmoc-Tic-Phe-Xaa was synthesized according to the procedure described in Example 23, utilizing 10 equiv. of Fmoc-L-Tic and Rink resin-bound Fmoc-Phe-Xaa.

EXAMPLE 28

Synthesis of N1-[[(3-Methoxyphenyl)amino]carbonyl]-Pro-Phe-BIP-$NH_2$

Rink resin-bound Fmoc-Pro-Phe-BIP prepared according to Example 8 was suspended in a solution (25 ml) of 25% piperidine in DMF (v/v) and agitated for 1 hour on an orbital shaker. The solution was removed by filtration, and the resin was then washed successively with DMF, MeOH, and DCM (three washes) and then dried in vacuo. To a portion of the dried resin (0.100 g) was added a solution of 3-methoxyphenyl isocyanate (0.15 g, 1.0 mmole, 12.5 equiv.) in anhydrous DMF (0.5 ml). The resin slurry was agitated for 18 hours on an orbital shaker, and then washed successively with DMF, MeOH, and DCM (three times). The Rink resin-bound compound was cleaved from the solid support by agitating the resin with 50% TFA in DCM (v/v) for 30 min followed by filtration and removal of the solvent in vacuo to give N1-[[(3-Methoxyphenyl)amino]carbonyl]-Pro-Phe-BIP-$NH_2$.

EXAMPLE 29

Synthesis of N1-[(3,4-Dichlorophenyl)methyl]-Pro-Phe-BIP-$NH_2$

Rink resin-bound Fmoc-Pro-Phe-BIP prepared according to Example 8 was suspended in a solution (25 ml) of 25% piperidine in DMF (v/v) and agitated for 1 hour on an orbital shaker. The solution was removed by filtration, and the resin was then washed successively with DMF, MeOH, and DCM (three washes) and then dried in vacuo. To a portion of the dried resin (0.100 g) was added a solution of 3,4-dichlorobenzaldehyde (0.21 g, 1.2 mmole, 15 equiv.) in anhydrous DMF (0.5 ml), and the resin slurry was then agitated for 1 hour. To this slurry was added sodium triacetoxyborohydride (2.4 mmole, 30 equiv.) in anhydrous DMF (200 µl) followed by acetic acid (20 µl). The resin slurry was agitated for 18 hours on an orbital shaker, and then washed successively with DMF, MeOH, and DCM (three times). The Rink resin-bound compound was cleaved from the solid support by agitating the resin with 50% TFA in DCM (v/v) for 30 min followed by filtration and removal of the solvent in vacuo to give N1-[(3,4-Dichlorophenyl)methyl]-Pro-Phe-BIP-$NH_2$.

EXAMPLE 30

Synthesis of N1-[(3,4-Dichlorophenyl)sulfonyl]-Pro-Phe-HPA-$NH_2$

Rink resin-bound Fmoc-Pro-Phe-HPA was suspended in a solution (25 ml) of 25% piperidine in DMF (v/v) and agitated for 1 hour on an orbital shaker. The solution was removed by filtration, and the resin was then washed successively with DMF, MeOH, and DCM (three washes) and then dried in vacuo. To a portion of the dried resin (0.100 g) was added a solution of 3,4-dichlorobenzenesulfonyl chloride (0.25 g, 1.0 mmole, 12.5 equiv.) in anhydrous DMF (0.5 ml) followed by N,N-diisopropylethylamine (0.13 g, 1.0 mmole, 12.5 equiv.). The resin slurry was agitated for 18 hours on an orbital shaker, and then washed successively with DMF, MeOH, and DCM (three times). The Rink resin-bound compound was cleaved from the solid support by agitating the resin with 50% TFA in DCM (v/v) for 30 min followed by filtration and removal of the solvent in vacuo to give N1-[(3,4-Dichlorophenyl)sulfonyl]-Pro-Phe-HPA-$NH_2$; MS (EI)=631 (M+).

EXAMPLE 31

Synthesis of N1-[[(2,5-Difluorophenyl)amino]carbonyl]-tert-Leu-Phe-HPA-$NH_2$

Rink resin-bound Fmoc-tert-Leu-Phe-HPA and 2,5-difluorophenyl isocyanate gave N1-[[(2,5-Difluorophenyl)amino]carbonyl]-tert-Leu-Phe-HPA-$NH_2$; MS (EI)=593 (M+).

EXAMPLE 32

Synthesis of N1-[[(3-Methoxyphenyl)amino]carbonyl]-Pro-Phe-DIP-$NH_2$

Rink resin-bound Fmoc-Pro-Phe-DIP and 3-methoxyphenyl isocyanate gave N1-[[(3-Methoxyphenyl)amino]carbonyl]-Pro-Phe-DIP-$NH_2$; MS (EI)=647 (M+).

EXAMPLE 33

Synthesis of N1-[[(3-Methoxyphenyl)amino]carbonyl]-Pro-Phe-4-FPA-NH$_2$

Rink resin-bound Fmoc-Pro-Phe-4-FPA and 3-methoxyphenyl isocyanate gave N1-[[(3-Methoxyphenyl)amino]carbonyl]-Pro-Phe-4-FPA-NH$_2$; MS (EI)=575 (M+).

EXAMPLE 34

Synthesis of N1-[[(2,5-Difluorophenyl)amino]carbonyl]-Thz-Phe-DIP-NH$_2$

Rink resin-bound Fmoc-Thz-Phe-DIP and 2,5-difluorophenyl isocyanate gave N1-[[(2,5-Difluorophenyl)amino]carbonyl]-Thz-Phe-DIP-NH$_2$; MS (EI)=671 (M+).

EXAMPLE 35

Synthesis of N1-[[(3-Methoxyphenyl)amino]carbonyl]-Thz-Phe-DIP-NH$_2$

Rink resin-bound Fmoc-Thz-Phe-DIP and 3-methoxyphenyl isocyanate gave N1-[[(3-Methoxyphenyl)amino]carbonyl]-Thz-Phe-DIP-NH$_2$; MS (EI)=665 (M+).

EXAMPLE 36

Synthesis of N1-[[(3-Methoxyphenyl)amino]carbonyl]-tert-Leu-Phe-3-CPA-NH$_2$

Rink resin-bound Fmoc-tert-Leu-Phe-3-CPA and 3-methoxyphenyl isocyanate gave N1-[[(3-Methoxyphenyl)amino]carbonyl]-tert-Leu-Phe-3-CPA-NH$_2$; MS (EI)=608 (M+).

EXAMPLE 37

Synthesis of N1-[[[3-(Trifluoromethyl)phenyl]amino]carbonyl-tert-Leu-Phe-3-CPA-NE$_2$ Rink resin-bound Fmoc-tert-Leu-Phe-3-CPA and 3-(trifluoromethyl)phenyl isocyanate gave N1-[[[3-(Trifluoromethyl)phenyl]amino]carbonyl]-tert-Leu-Phe-3-CPA-NH$_2$; MS (EI)=646 (M+).

EXAMPLE 38

Synthesis of N1-[[(2,5-Difluorophenyl)amino]carbonyl]-tert-Leu-Phe-3-CPA-NH$_2$

Rink resin-bound Fmoc-tert-Leu-Phe-3-CPA and 2,5-difluorophenyl isocyanate gave N1-[[(2,5-Difluorophenyl)amino]carbonyl]-tert-Leu-Phe-3-CPA-NH$_2$; MS (EI)=614 (M+).

EXAMPLE 39

Synthesis of N1-[[(3-Methoxyphenyl)amino]carbonyl]-tert-Leu-Phe-DIP-NH$_2$

Rink resin-bound Fmoc-tert-Leu-Phe-DIP and 3-methoxyphenyl isocyanate gave N1-[[(3-Methoxyphenyl)amino]carbonyl]-tert-Leu-Phe-DIP-NH$_2$; MS (EI)=663 (M+).

EXAMPLE 40

Synthesis of N1-[[[3-(Trifluoromethyl)phenyl]amino]carbonyl]-tert-Leu-Phe-DIP-NH$_2$ Rink resin-bound Fmoc-tert-Leu-Phe-DIP and 3-(trifluoromethyl)phenyl isocyanate gave N1-[[[3-(Trifluoromethyl)phenyl]amino]carbonyl]-tert-Leu-Phe-DIP-NH$_2$; MS (EI)=625 (M+).

EXAMPLE 41

Synthesis of N1-[[(2,5-Difluorophenyl)amino]carbonyl]-tert-Leu-Phe-DIP-NH$_2$

Rink resin-bound Fmoc-tert-Leu-Phe-DIP and 2,5-difluorophenyl isocyanate gave N1-[[(2,5-Difluorophenyl)amino]carbonyl]-tert-Leu-Phe-DIP-NH$_2$; MS (EI)=669 (M+).

EXAMPLE 42

Synthesis of N1-[[[4-(Methylthio)phenyl]amino]carbonyl]-tert-Leu-Phe-3,4-DCP-NH$_2$ Rink resin-bound Fmoc-tert-Leu-Phe-3,4-DCP and 4-(methylthio)phenyl isocyanate gave N1-[[[4-(Methylthio)phenyl]amino]carbonyl]-tert-Leu-Phe-3,4-DCP-NH$_2$; MS (EI)=658 (M+).

EXAMPLE 43

Synthesis of N1-[[(3-Methoxyphenyl)amino]carbonyl]-tert-Leu-Phe-3-PAL-NH$_2$

Rink resin-bound Fmoc-tert-Leu-Phe-3-PAL and 3-methoxyphenyl isocyanate gave N1-[[(3-Methoxyphenyl)amino]carbonyl]-tert-Leu-Phe-3-PAL-NH$_2$; MS (EI)=574 (M+).

EXAMPLE 44

Synthesis of N1-[[[4-(Methylthio)phenyl]amino]carbonyl]-tert-Leu-Phe-3-PAL-NH$_2$ Rink resin-bound Fmoc-tert-Leu-Phe-3-PAL and 4-(methylthio)phenyl isocyanate gave N1-[[[4-(Methylthio)phenyl]amino]carbonyl]-tert-Leu-Phe-3-PAL-NH$_2$; MS (EI)=590 (M+).

EXAMPLE 45

Synthesis of N1-[[[3-(Trifluoromethyl)phenyl]amino]carbonyl]-tert-Leu-Phe-HPA-NH$_2$ Rink resin-bound Fmoc-tert-Leu-Phe-HPA and 3-(trifluoromethyl)phenyl isocyanate gave N1-[[[3-(Trifluoromethyl)phenyl]amino]carbonyl]-tert-Leu-Phe-HPA-NH$_2$; MS (EI)=625 (M+).

EXAMPLE 46

Synthesis of N1-[[(3-Methoxyphenyl)amino]carbonyl]-tert-Leu-Phe-HPA-NH$_2$

Rink resin-bound Fmoc-tert-Leu-Phe-HPA and 3-methoxyphenyl isocyanate gave N1-[[(3-Methoxyphenyl)amino]carbonyl]-tert-Leu-Phe-HPA-NH$_2$; MS (EI)=587 (M+).

EXAMPLE 47

Synthesis of N1-[[(3-Methoxyphenyl)amino]carbonyl]-tert-Leu-Phe-BIP-NH$_2$

Rink resin-bound Fmoc-tert-Leu-Phe-BIP and 3-methoxyphenyl isocyanate gave N1-[[(3-Methoxyphenyl)amino]carbonyl]-tert-Leu-Phe-BIP-NH$_2$; MS (EI)=649 (M+).

EXAMPLE 48

Synthesis of N1-[[(3-Methoxyphenyl)amino]
carbonyl]-tert-Leu-Phe-3,4-DCP-NH$_2$

Rink resin-bound Fmoc-tert-Leu-Phe-3,4-DCP and 3-methoxyphenyl isocyanate gave N1-[[(3-Methoxyphenyl)amino]carbonyl]-tert-Leu-Phe-3,4-DCP-NH$_2$; MS (EI)=642 (M+).

EXAMPLE 49

Synthesis of N1-[[(3-Methoxyphenyl)amino]
carbonyl]-Pro-Phe-3,4-DCP-NH$_2$

Rink resin-bound Fmoc-Pro-Phe-3,4-DCP and 3-methoxyphenyl isocyanate gave N1-[[(3-Methoxyphenyl)amino]carbonyl]-Pro-Phe-3,4-DCP-NH$_2$; MS (EI)=626 (M+).

EXAMPLE 50

Synthesis of N1-[[(3-Methoxyphenyl)amino]
carbonyl]-Pro-Phe-BIP-NH$_2$

Rink resin-bound Fmoc-Pro-Phe-BIP and 3-methoxyphenyl isocyanate gave N1-[[(3-Methoxyphenyl)amino]carbonyl]-Pro-Phe-BIP-NH$_2$; MS (EI)=633 (M+).

EXAMPLE 51

Synthesis of N1-[[(3,4-Dichlorophenyl)amino]
carbonyl]-Pro-Phe-HPA-NH$_2$

Rink resin-bound Fmoc-Pro-Phe-HPA and 3,4-dichlorophenyl isocyanate gave N1-[[(3,4-Dichlorophenyl)amino]carbonyl]-Pro-Phe-HPA-NH$_2$; MS (EI)=610 (M+).

EXAMPLE 52

Synthesis of N1-[[(2,5-Difluorophenyl)amino]
carbonyl]-Pro-Phe-HPA-NH$_2$

Rink resin-bound Fmoc-Pro-Phe-HPA and 2,5-difluorophenyl isocyanate gave N1-[[(2,5-Difluorophenyl)amino]carbonyl]-Pro-Phe-HPA-NH$_2$; MS (EI)=577 (M+).

EXAMPLE 53

Synthesis of N1-[[(3,4-Dichlorophenyl)amino]
carbonyl]-Thz-Phe-HPA-NH$_2$

Rink resin-bound Fmoc-Thz-Phe-HPA and 3,4-dichlorophenyl isocyanate gave N1-[[(3,4-Dichlorophenyl)amino]carbonyl]-Thz-Phe-HPA-NH$_2$; MS (EI)=628 (M+).

EXAMPLE 54

Synthesis of N1-[[(2,5-Difluoronhenyl)amino]
carbonyl]-Thz-Phe-HPA-NH$_2$

Rink resin-bound Fmoc-Thz-Phe-HPA and 2,5-difluorophenyl isocyanate gave N1-[[(2,5-Difluorophenyl)amino]carbonyl]-Thz-Phe-HPA-NH$_2$; MS (EI)=595 (M+).

EXAMPLE 55

Synthesis of N1-[(3,4-Dichlorophenyl)sulfonyl]-
Pro-Phe-HPA-NH$_2$

Rink resin-bound Fmoc-Pro-Phe-HPA and 3,4-dichlorobenzenesulfonyl chloride gave N1-[(3,4-Dichlorophenyl)sulfonyl]-Pro-Phe-HPA-NH$_2$; MS (EI)=631 (M+).

EXAMPLE 56

Synthesis of N1-[(3,4-Dichlorophenyl)sulfonyl]-
Thz-Phe-HPA-NH$_2$

Rink resin-bound Fmoc-Thz-Phe-HPA and 3,4-dichlorobenzenesulfonyl chloride gave N1-[(3,4-Dichlorophenyl)sulfonyl]-Thz-Phe-HPA-NH$_2$; MS (EI)=649 (M+).

EXAMPLE 57

Synthesis of N1-[[(2,6-Dimethylnhenyl)amino]
carbonyl]-Pro-Phe-D-HPA-NH$_2$

Rink resin-bound Fmoc-Pro-Phe-D-HPA and 2,6-dimethylphenyl isocyanate gave N1-[[(2,6-Dimethylphenyl)amino]carbonyl]-Pro-Phe-D-HPA-NH$_2$; MS (EI)=569 (M+).

EXAMPLE 58

Synthesis of N1-[[(3,4-Dichlorophenyl)amino]
carbonyl]-Pro-Phe-D-HPA-NH$_2$

Rink resin-bound Fmoc-Pro-Phe-D-HPA and 3,4-dichlorophenyl isocyanate gave N1-[[(3,4-Dichlorophenyl)amino]carbonyl]-Pro-Phe-D-HPA-NH$_2$; MS (EI)=610 (M+).

EXAMPLE 59

Synthesis of N1-[[(3-Methoxyphenyl)amino]
carbonyl]-Pro-Phe-D-BIP-NH$_2$

Rink resin-bound Fmoc-Pro-Phe-D-BIP and 3-methoxyphenyl isocyanate gave N1-[[(3-Methoxyphenyl)amino]carbonyl]-Pro-Phe-D-BIP-NH$_2$; MS (EI)=633 (M+).

EXAMPLE 60

Synthesis of N1-[[(2,6-Dimethylphenyl)amino]
carbonyl]-tert-Leu-Phe-D-HPA-NH$_2$ Rink resin-bound Fmoc-tert-Leu-Phe-D-HPA and 2,6-dimethylphenyl isocyanate gave N1-[[(2,6-Dimethylphenyl)amino]carbonyl]-tert-Leu-Phe-D-HPA-NH$_2$; MS (EI)=585 (M+).

EXAMPLE 61

Synthesis of N1-[[(3,4-Dichlorophenyl)amino]
carbonyl]-tert-Leu-Phe-D-HPA-NH$_2$ Rink resin-bound Fmoc-tert-Leu-Phe-D-HPA and 3,4-dichlorophenyl isocyanate gave N1-[[(3,4-Dichlorophenyl)amino]carbonyl]-tert-Leu-Phe-D-HPA-NH$_2$; MS (EI)=626 (M+).

EXAMPLE 62

Synthesis of N1-[[(2,5-Difluorophenyl)amino]
carbonyl]-tert-Leu-Phe-D-HPA-NH$_2$ Rink resin-bound Fmoc-tert-Leu-Phe-D-HPA and 2,5-difluorophenyl isocyanate gave N1-[[(2,5-Difluorophenyl)amino]carbonyl]-tert-Leu-Phe-D-HPA-NH$_2$; MS (EI)=593 (M+).

EXAMPLE 63

Synthesis of N1-[[(3-Methoxyphenyl)amino]
carbonyl]-Pro-D-Phe-BIP-NH$_2$

Rink resin-bound Fmoc-Pro-D-Phe-BIP and 3-methoxyphenyl isocyanate gave N1-[[(3-Methoxyphenyl)amino]carbonyl]-Pro-D-Phe-BIP-NH$_2$; MS (EI)=633 (M+).

EXAMPLE 64

Synthesis of N1-[[(2,5-Difluoronhenyl)amino]carbonyl]-tert-Leu-D-Phe-HPA-NH$_2$

Rink resin-bound Fmoc-tert-Leu-D-Phe-HPA and 2,5-difluorophenyl isocyanate gave N1-[[(2,5-Difluorophenyl)amino]carbonyl]-tert-Leu-D-Phe-HPA-NH$_2$; MS (EI)=593 (M+).

EXAMPLE 65

Synthesis of N1-[[(3-Methoxyphenyl)amino]carbonyl]-D-Pro-Phe-BIP-NH$_2$

Rink resin-bound Fmoc-D-Pro-Phe-BIP and 3-methoxyphenyl isocyanate gave N1-[[(3-Methoxyphenyl)amino]carbonyl]-D-Pro-Phe-BIP-NH$_2$; MS (EI)=633 (M+).

EXAMPLE 66

Synthesis of N1-[[(2,5-Difluorophenyl)amino]carbonyl]-D-tert-Leu-Phe-HPA-NH$_2$

Rink resin-bound Fmoc-D-tert-Leu-Phe-HPA and 2,5-difluorophenyl isocyanate gave N1-[[(2,5-Difluorophenyl)amino]carbonyl]-D-tert-Leu-Phe-HPA-NH$_2$; MS (EI)=593 (M+).

EXAMPLE 67

Synthesis of N1-[[(2,5-Difluorophenyl)amino]carbonyl]-tert-Leu-D-Phe-D-HPA-NH$_2$ Rink resin-bound Fmoc-tert-Leu-D-Phe-D-HPA and 2,5-difluorophenyl isocyanate gave N1-[[(2,5-Difluorophenyl)amino]carbonyl]-tert-Leu-D-Phe-D-HPA-NH$_2$; MS (EI)=593 (M+).

EXAMPLE 68

Synthesis of N1-[[(2,5-Difluorophenyl)amino]carbonyl]-D-tert-Leu-Phe-D-HPA-NH$_2$ Rink resin-bound Fmoc-D-tert-Leu-Phe-D-HPA and 2,5-difluorophenyl isocyanate gave N1-[[(2,5-Difluorophenyl)amino]carbonyl]-D-tert-Leu-Phe-D-HPA-NH$_2$; MS (EI)=593 (M+).

EXAMPLE 69

Synthesis of N1-[[(2,5-Difluorophenyl)amino]carbonyl]-D-tert-Leu-D-Phe-HPA-NH$_2$ Rink resin-bound Fmoc-D-tert-Leu-D-Phe-HPA and 2,5-difluorophenyl isocyanate gave N1-[[(2,5-Difluorophenyl)amino]carbonyl]-D-tert-Leu-D-Phe-HPA-NH$_2$; MS (EI)=593 (M+).

EXAMPLE 70

Synthesis of N1-[[(2,5-Difluorophenyl)amino]carbonyl]-D-tert-Leu-D-Phe-D-HPA-NH$_2$ Rink resin-bound Fmoc-D-tert-Leu-D-Phe-D-HPA and 2,5-difluorophenyl isocyanate gave N1-[[(2,5-Difluorophenyl)amino]carbonyl]-D-tert-Leu-D-Phe-D-HPA-NH$_2$; MS (EI)=593 (M+).

EXAMPLE 71

Synthesis of N1-[(3,4-Dichlorophenyl)methyl]-tert-Leu-Phe-HPA-NH$_2$

Rink resin-bound Fmoc-tert-Leu-Phe-HPA and 3,4-dichlorobenzaldehyde gave N1-[(3,4-Dichlorophenyl)methyl]-tert-Leu-Phe-HPA-NH$_2$; MS (EI)=597 (M+).

EXAMPLE 72

Synthesis of N1-[[3-(Trifluoromethyl)phenyl]methyl]-tert-Leu-Phe-HPA-NH$_2$

Rink resin-bound Fmoc-tert-Leu-Phe-HPA and 3-(trifluoromethyl)benzaldehyde gave N1-[[3-(Trifluoroethyl)phenyl]methyl]-tert-Leu-Phe-HPA-NH$_2$; MS (EI)=596 (M+).

EXAMPLE 73

Synthesis of N1-[(2,5-Difluorophenyl)methyl]-tert-Leu-Phe-HPA-NH$_2$

Rink resin-bound Fmoc-tert-Leu-Phe-HPA and 2,5-difluorobenzaldehyde gave N1-[(2,5-Difluorophenyl)methyl]-tert-Leu-Phe-HPA-NH$_2$; MS (EI)=564 (M+).

EXAMPLE 74

Synthesis of N1-[(3-Methoxyphenyl)methyl]-tert-Leu-Phe-HPA-NH$_2$

Rink resin-bound Fmoc-tert-Leu-Phe-HPA and 3-methoxybenzaldehyde gave N1-[(3-Methoxyphenyl)methyl]-tert-Leu-Phe-HPA-NH$_2$; MS (EI)=558 (M+).

EXAMPLE 75

Synthesis of N1-[(3,4-Dichlorophenyl)methyl]-Pro-Phe-HPA-NH$_2$

Rink resin-bound Fmoc-Pro-Phe-HPA and 3,4-dichlorobenzaldehyde gave N1-[(3,4-Dichlorophenyl)methyl]-Pro-Phe-HPA-NH$_2$; MS (EI)=581 (M+).

EXAMPLE 76

Synthesis of N1-[[3-(Trifluoromethyl)phenyl]methyl]-Pro-Phe-HPA-NH$_2$

Rink resin-bound Fmoc-Pro-Phe-HPA and 3-(trifluoromethyl)benzaldehyde gave N1-[[3-(Trifluoromethyl)phenyl]methyl]-Pro-Phe-HPA-NH$_2$; MS (EI)=580 (M+).

EXAMPLE 77

Synthesis of N1-[(2,5-Difluorophenyl)methyl]-Pro-Phe-HPA-NH$_2$

Rink resin-bound Fmoc-Pro-Phe-HPA and 2,5-difluorobenzaldehyde gave N1-[(2,5-Difluorophenyl)methyl]-Pro-Phe-HPA-NH$_2$; MS (EI)=548 (M+).

EXAMPLE 78

Synthesis of N1-[(3-Methoxyphenyl)methyl]-Pro-Phe-HPA-NH$_2$

Rink resin-bound Fmoc-Pro-Phe-HPA and 3-methoxybenzaldehyde gave N1-[(3-Methoxyphenyl)methyl]-Pro-Phe-HPA-NH$_2$; MS (EI)=542 (M+).

EXAMPLE 79

Synthesis of N1-[(Imidazol-2-yl)methyl-tert-Leu-Phe-HPA-NH$_2$

Rink resin-bound Fmoc-tert-Leu-Phe-HPA and 2-imidazolecarboxaldehyde gave N1-[(Imidazol-2-yl)methyl]-tert-Leu-Phe-HPA-NH$_2$; MS (EI)=518 (M+).

EXAMPLE 80

Synthesis of N1-[(3-Indolyl)methyl]-tert-Leu-Phe-HPA-NH$_2$

Rink resin-bound Fmoc-tert-Leu-Phe-HPA and indole-3-carboxaldehyde gave N1-[(3-Indolyl)methyl]-tert-Leu-Phe-HPA-NH$_2$; MS (EI)=567 (M+).

EXAMPLE 81

Synthesis of N1-[(Imidazol-2-yl)methyl]-Pro-Phe-HPA-NH$_2$

Rink resin-bound Fmoc-Pro-Phe-HPA and 2-imidazolecarboxaldehyde gave N1-[(Imidazol-2-yl)methyl]-Pro-Phe-HPA-NH$_2$; MS (EI)=502 (M+).

EXAMPLE 82

Synthesis of N1-[(3-Indolyl)methyl]-Pro-Phe-HPA-NH$_2$

Rink resin-bound Fmoc-Pro-Phe-HPA and indole-3-carboxaldehyde gave N1-[(3-Indolyl)methyl]-Pro-Phe-HPA-NH$_2$; MS (EI)=551 (M+).

EXAMPLE 83

Synthesis of N1-[(3,4-Dichlorophenyl)methyl]-tert-Leu-Phe-BIP-NH$_2$

Rink resin-bound Fmoc-tert-Leu-Phe-BIP and 3,4-dichlorobenzaldehyde gave N1-[(3,4-Dichlorophenyl)methyl]-tert-Leu-Phe-BIP-NH$_2$; MS (EI)=659 (M+).

EXAMPLE 84

Synthesis of N1-[[3-(Trifluoromethyl)phenyl]methyl]-tert-Leu-Phe-BIP-NH$_2$

Rink resin-bound Fmoc-tert-Leu-Phe-BIP and 3-(trifluoromethyl)benzaldehyde gave N1-[[3-(Trifluoromethyl)phenyl]methyl]-tert-Leu-Phe-BIP-NH$_2$; MS (EI)=658 (M+).

EXAMPLE 85

Synthesis of N1-[(2,5-Difluorophenyl)methyl]-tert-Leu-Phe-BIP-NH$_2$

Rink resin-bound Fmoc-tert-Leu-Phe-BIP and 2,5-difluorobenzaldehyde gave N1-[(2,5-Difluorophenyl)methyl]-tert-Leu-Phe-BIP-NH$_2$; MS (EI)=626 (M+).

EXAMPLE 86

Synthesis of N1-[(3-Methoxyphenyl)methyl]-tert-Leu-Phe-BIP-NH$_2$

Rink resin-bound Fmoc-tert-Leu-Phe-BIP and 3-methoxybenzaldehyde gave N1-[(3-Methoxyphenyl)methyl]-tert-Leu-Phe-BIP-NH$_2$; MS (EI)=620 (M+).

EXAMPLE 87

Synthesis of N1-[(3,4-Dichlorophenyl)methyl]-Pro-Phe-BIP-NH$_2$

Rink resin-bound Fmoc-Pro-Phe-BIP and 3,4-dichlorobenzaldehyde gave N1-[(3,4-Dichlorophenyl)methyl]-Pro-Phe-BIP-NH$_2$; MS (EI)=643 (M+).

EXAMPLE 88

Synthesis of N1-[[3-(Trifluoromethyl)phenyl]methyl]-Pro-Phe-BIP-NH$_2$

Rink resin-bound Fmoc-Pro-Phe-BIP and 3-(trifluoromethyl)benzaldehyde gave N1-[[3-(Trifluoromethyl)phenyl]methyl]-Pro-Phe-BIP-NH$_2$; MS (EI)=642 (M+).

EXAMPLE 89

Synthesis of N1-[(2,5-Difluorophenyl)methyl]-Pro-Phe-BIP-NH$_2$

Rink resin-bound Fmoc-Pro-Phe-BIP and 2,5-difluorobenzaldehyde gave N1-[(2,5-Difluorophenyl)methyl]-Pro-Phe-BIP-NH$_2$; MS (EI)=610 (M+).

EXAMPLE 90

Synthesis of N1-[(3-Methoxyphenyl)methyl]-Pro-Phe-BIP-NH$_2$

Rink resin-bound Fmoc-Pro-Phe-BIP and 3-methoxybenzaldehyde gave N1-[(3-Methoxyphenyl)methyl]-Pro-Phe-BIP-NH$_2$; MS (EI)=604 (M+).

EXAMPLE 91

Synthesis of N1-[(Imidazol-2-yl)methyl]-tert-Leu-Phe-BIP-NH$_2$

Rink resin-bound Fmoc-tert-Leu-Phe-BIP and 2-imidazolecarboxaldehyde gave N1-[(Imidazol-2-yl)methyl]-tert-Leu-Phe-BIP-NH$_2$; MS (EI)=580 (M+).

EXAMPLE 92

Synthesis of N1-[(3-Indolyl)methyl]-tert-Leu-Phe-BIP-NH$_2$

Rink resin-bound Fmoc-tert-Leu-Phe-BIP and indole-3-carboxaldehyde gave N1-[(3-Indolyl)methyl]-tert-Leu-Phe-BIP-NH$_2$; MS (EI)=629 (M+).

EXAMPLE 93

Synthesis of N1-[(3-Indolyl)methyl]-Pro-Phe-BIP-NH$_2$

Rink resin-bound Fmoc-Pro-Phe-BIP and indole-3-carboxaldehyde gave N1-[(3-Indolyl)methyl]-Pro-Phe-BIP-NH$_2$; MS (EI)=613 (M+).

EXAMPLE 94

Synthesis of N1-[(Imidazol-2-yl)methyl]-Pro-Phe-BIP-NH$_2$

Rink resin-bound Fmoc-Pro-Phe-BIP and 2-imidazolecarboxaldehyde gave N1-[(Imidazol-2-yl)methyl]-Pro-Phe-BIP-NH$_2$; MS (EI)=564 (M+).

EXAMPLE 95

Synthesis of N1-[(3,4-Dichlorophenyl)methyl]-tert-Leu-Phe-2-NAL-NH$_2$

Rink resin-bound Fmoc-tert-Leu-Phe-2-NAL and 3,4-dichlorobenzaldehyde gave N1-[(3,4-Dichlorophenyl)methyl]-tert-Leu-Phe-2-NAL-NH$_2$; MS (EI)=633 (M+).

EXAMPLE 96

Synthesis of N1-[[3-(Trifluoromethyl)phenyl]
methyl]-tert-Leu-Phe-2-NAL-NH$_2$

Rink resin-bound Fmoc-tert-Leu-Phe-2-NAL and 3-(trifluoromethyl)benzaldehyde gave N1-[[3-(Trifluoromethyl)phenyl]methyl]-tert-Leu-Phe-2-NAL-NH$_2$; MS (EI)=632 (M+).

EXAMPLE 97

Synthesis of N1-[(2,5-Difluorophenyl)methyl]-tert-Leu-Phe-2-NAL-NH$_2$

Rink resin-bound Fmoc-tert-Leu-Phe-2-NAL and 2,5-difluorobenzaldehyde gave N1-[(2,5-Difluorophenyl)methyl]-tert-Leu-Phe-2-NAL-NH$_2$; MS (EI)=600 (M+).

EXAMPLE 98

Synthesis of N1-[(3-Methoxyphenyl)methyl]-tert-Leu-Phe-2-NAL-NH$_2$

Rink resin-bound Fmoc-tert-Leu-Phe-2-NAL and 3-methoxybenzaldehyde gave N1-[(3-Methoxyphenyl)methyl]-tert-Leu-Phe-2-NAL-NH$_2$; MS (EI)=594 (M+).

EXAMPLE 99

Synthesis of N1-[(3,4-Dichlorophenyl)methyl]-Pro-Phe-2-NAL-NH$_2$

Rink resin-bound Fmoc-Pro-Phe-2-NAL and 3,4-dichlorobenzaldehyde gave N1-[(3,4-Dichlorophenyl)methyl]-Pro-Phe-2-NAL-NH$_2$; MS (EI)=617 (M+).

EXAMPLE 100

Synthesis of N1-[[3-(Trifluoromethyl)phenyl]
methyl]-Pro-Phe-2-NAL-NH$_2$

Rink resin-bound Fmoc-Pro-Phe-2-NAL and 3-(trifluoromethyl)benzaldehyde gave N1-[[3-(Trifluoromethyl)phenyl]methyl]-Pro-Phe-2-NAL-NH$_2$; MS (EI)=616 (M+).

EXAMPLE 101

Synthesis of N1-[(2,5-Difluorophenyl)methyl]-Pro-Phe-2-NAL-NH$_2$

Rink resin-bound Fmoc-Pro-Phe-2-NAL and 2,5-difluorobenzaldehyde gave N1-[(2,5-Difluorophenyl)methyl]-Pro-Phe-2-NAL-NH$_2$; MS (EI)=584 (M+).

EXAMPLE 102

Synthesis of N1-[(3-Methoxyphenyl)methyl]-Pro-Phe-2-NAL-NH$_2$

Rink resin-bound Fmoc-Pro-Phe-2-NAL and 3-methoxybenzaldehyde gave N1-[(3-Methoxyphenyl)methyl]-Pro-Phe-2-NAL-NH$_2$; MS (EI)=578 (M+).

EXAMPLE 103

Synthesis of N1-[(Imidazol-2-yl)methyl]-tert-Leu-Phe-2-NAL-NH$_2$

Rink resin-bound Fmoc-tert-Leu-Phe-2-NAL and 2-imidazolecarboxaldehyde gave N1-[(Imidazol-2-yl)methyl]-tert-Leu-Phe-2-NAL-NH$_2$; MS (EI)=554 (M+).

EXAMPLE 104

Synthesis of N1-[(3-Indolyl)methyl]-tert-Leu-Phe-2-NAL-NH$_2$

Rink resin-bound Fmoc-tert-Leu-Phe-2-NAL and indole-3-carboxaldehyde gave N1-[(3-Indolyl)methyl]-tert-Leu-Phe-2-NAL-NH$_2$; MS (EI)=603 (M+).

EXAMPLE 105

Synthesis of N1-[(Imidazol-2-yl)methyl]-Pro-Phe-2-NAL-NH$_2$

Rink resin-bound Fmoc-Pro-Phe-2-NAL and 2-imidazolecarboxaldehyde gave N1-[(Imidazol-2-yl)methyl]-Pro-Phe-2-NAL-NH$_2$; MS (EI)=538 (M+).

EXAMPLE 106

Synthesis of N1-[(3-Indolyl)methyl]-Pro-Phe-2-NAL-NH$_2$

Rink resin-bound Fmoc-Pro-Phe-2-NAL and indole-3-carboxaldehyde gave N1-[(3-Indolyl)methyl]-Pro-Phe-2-NAL-NH$_2$; MS (EI)=587 (M+).

EXAMPLE 107

Synthesis of N1-[(3,4-Dichlorophenyl)methyl]-tert-Leu-Phe-Phe-NH$_2$

Rink resin-bound Fmoc-tert-Leu-Phe-Phe and 3,4-dichlorobenzaldehyde gave N1-[(3,4-Dichlorophenyl)methyl]-tert-Leu-Phe-Phe-NH$_2$; MS (EI)=583 (M+).

EXAMPLE 108

Synthesis of N1-[[3-(Trifluoromethyl)phenyl]
methyl]-tert-Leu-Phe-Phe-NH$_2$

Rink resin-bound Fmoc-tert-Leu-Phe-Phe and 3-(trifluoromethyl)benzaldehyde gave N1-[[3-(Trifluoromethyl)phenyl]methyl]-tert-Leu-Phe-Phe-NH$_2$; MS (EI)=582 (M+).

EXAMPLE 109

Synthesis of N1-[(2,5-Difluorophenyl)methyl]-tert-Leu-Phe-Phe-NH$_2$

Rink resin-bound Fmoc-tert-Leu-Phe-Phe and 2,5-difluorobenzaldehyde gave N1-[(2,5-Difluorophenyl)methyl]-tert-Leu-Phe-Phe-NH$_2$; MS (EI)=550 (M+).

EXAMPLE 110

Synthesis of N1-[(3-Methoxyphenyl)methyl]-tert-Leu-Phe-Phe-NH$_2$

Rink resin-bound Fmoc-tert-Leu-Phe-Phe and 3-methoxybenzaldehyde gave N1-[(3-Methoxyphenyl)methyl]-tert-Leu-Phe-Phe-NH$_2$; MS (EI)=544 (M+).

EXAMPLE 111

Synthesis of N1-[(3,4-Dichlorophenyl)methyl]-Pro-Phe-Phe-NH$_2$

Rink resin-bound Fmoc-Pro-Phe-Phe and 3,4-dichlorobenzaldehyde gave N1-[(3,4-Dichlorophenyl)methyl]-Pro-Phe-Phe-NH$_2$; MS (EI)=567 (M+).

EXAMPLE 112

Synthesis of N1-[[3-(Trifluoromethyl)phenyl]methyl]-Pro-Phe-Phe-NH$_2$

Rink resin-bound Fmoc-Pro-Phe-Phe and 3-(trifluoromethyl)benzaldehyde gave N1-[[3-(Trifluoromethyl)phenyl]methyl]-Pro-Phe-Phe-NH$_2$; MS (EI)=566 (M+).

EXAMPLE 113

Synthesis of N1-[(2,5-Difluorophenyl)methyl]-Pro-Phe-Phe-NH$_2$

Rink resin-bound Fmoc-Pro-Phe-Phe and 2,5-difluorobenzaldehyde gave N1-[(2,5-Difluorophenyl)methyl]-Pro-Phe-Phe-NH$_2$; MS (EI)=534 (M+).

EXAMPLE 114

Synthesis of N1-[(3-Methoxyphenyl)methyl]-Pro-Phe-Phe-NH$_2$

Rink resin-bound Fmoc-Pro-Phe-Phe and 3-methoxybenzaldehyde gave N1-[(3-Methoxyphenyl)methyl]-Pro-Phe-Phe-NH$_2$; MS (EI)=528 (M+).

EXAMPLE 115

Synthesis of N1-[(Imidazol-2-yl)methyl]-tert-Leu-Phe-Phe-NH$_2$

Rink resin-bound Fmoc-tert-Leu-Phe-Phe and 2-imidazolecarboxaldehyde gave N1-[(Imidazol-2-yl)methyl]-tert-Leu-Phe-Phe-NH$_2$; MS (EI)=504 (M+).

EXAMPLE 116

Synthesis of N1-[(3-Indolyl)methyl]-tert-Leu-Phe-Phe-NH$_2$

Rink resin-bound Fmoc-tert-Leu-Phe-Phe and indole-3-carboxaldehyde gave N1-[(3-Indolyl)methyl]-tert-Leu-Phe-Phe-NH$_2$; MS (EI)=553 (M+).

EXAMPLE 117

Synthesis of N1-[(Imidazol-2-yl)methyl]-Pro-Phe-Phe-NH$_2$

Rink resin-bound Fmoc-Pro-Phe-Phe and 2-imidazolecarboxaldehyde gave N1-[(Imidazol-2-yl)methyl]-Pro-Phe-Phe-NH$_2$; MS (EI)=488 (M+).

EXAMPLE 118

Synthesis of N1-[(3-Indolyl)methyl]-Pro-Phe-Phe-NH$_2$

Rink resin-bound Fmoc-Pro-Phe-Phe and indole-3-carboxaldehyde gave N1-[(3-Indolyl)methyl]-Pro-Phe-Phe-NH$_2$; MS (EI)=537 (M+).

EXAMPLE 119

Synthesis of Rink resin-bound N1-[3-(Chloromethyl)benzoyl]-Phe-HPA

Rink resin-bound Fmoc-Phe-HPA was suspended in a solution (25 ml) of 25% piperidine in DMF (v/v) and agitated for 1 hour on an orbital shaker. The solution was removed by filtration, and the resin was then washed successively with DMF, MeOH, and DCM (three washes) and then dried in vacuo. To a portion of the dried resin (1.5 g, 1.2 mmole) was added a solution of 3-(chloromethyl)benzoyl chloride, (0.91 g, 4.8 mmole, 4.0 equiv.) in THF/DCM, 2:1 v/v (15 ml total) followed by N,N-diisopropylethylamine (0.93 g, 7.2 mmole, 6.0 equiv.). The resin slurry was agitated for 18 hours on an orbital shaker, and then the solution was removed by filtration. The resin was washed successively with DMF and DCM (three washes) and then dried in vacuo to give rink resin-bound N1-[3-(chloromethyl)benzoyl]-Phe-HPA.

EXAMPLE 120

Synthesis of Rink resin-bound N1-[4-(Chloromethyl)benzoyl]-Phe-HPA

This product was synthesized according to the procedure described in Example 119, utilizing 4.0 equiv. of 4-(chloromethyl)benzoyl chloride.

EXAMPLE 121

Synthesis of Rink resin-bound N1-[4-(Bromomethyl)benzenesulfonyl]-Phe-HPA

This product was synthesized according to the procedure described in Example 119, utilizing 4.0 equiv. of 4-(bromomethyl)benzenesulfonyl chloride.

EXAMPLE 122

N1-[3-[[4-(2-methoxyphenyl)-1-piperazinyl]methyl]benzoyl]-Phe-HPA-NH$_2$

To a portion of the dried rink resin-bound N1-[3-(Chloromethyl)benzoyl]-Phe-HPA (0.100 g, 0.08 mmole) was added a solution of 1-(2-methoxyphenyl)piperazine (0.92 g, 4.8 mmole, 6.0 equiv.) in anhydrous DMF (0.5 ml). The resin slurry was agitated for 18 hours on an orbital shaker, and then washed successively with DMF, MeOH, and DCM (three times). The Rink resin-bound compound was cleaved from the solid support by agitating the resin with 50% TFA in DCM (v/v) for 30 min followed by filtration and removal of the solvent in vacuo to give N1-[3-[[4-(2-methoxyphenyl)-1-piperazinyl]methyl]benzoyl]-Phe-HPA-NH$_2$; MS (EI)=633 (M+).

EXAMPLE 123

Synthesis of N1-[3-[[4-(2-methoxyphenyl)-1-piperazinyl]methyl]benzoyl]-Phe-HPA-NH$_2$ Rink resin-bound N1-[3-(Chloromethyl)benzoyl]-Phe-HPA and 1-(2-methoxyphenyl)piperazine gave N1-[3-[[4-(2-methoxyphenyl)-1-piperazinyl]methyl]benzoyl]-Phe-HPA-NH$_2$; MS (EI)=633 (M+).

EXAMPLE 124

Synthesis of N1-[3-[(N-benzyl-N-methylamino)methyl]benzoyl]-Phe-HPA-NH$_2$

Rink resin-bound N1-[3-(Chloromethyl)benzoyl]-Phe-HPA and N-benzylmethylamine gave N1-[3-[(N-benzyl-N-methylamino)methyl]benzoyl]-Phe-HPA-NH$_2$; MS (EI)=562 (M+).

EXAMPLE 125

Synthesis of N1-[3-[(4-benzyl-1-piperazinyl)methyl]benzoyl]-Phe-HPA-NH$_2$

Rink resin-bound N1-[3-(Chloromethyl)benzoyl]-Phe-HPA and 1-benzylpiperazine gave N1-[3-[(4-benzyl-1-piperazinyl)methyl]benzoyl]-Phe-HPA-NH$_2$; MS (EI)=617 (M+).

EXAMPLE 126

Synthesis of N1-[4-[[N-(2,5-difluorophenyl)methylamino]methyl]benzoyl]-Phe-HPA-NH$_2$ Rink resin-bound N1-[4-(Chloromethyl)benzoyl]-Phe-HPA and 2,5-difluorobenzylamine gave N1-[4-[[N-(2,5-difluorophenyl)methylamino]methyl]benzoyl]-Phe-HPA-NH$_2$; MS (EI)=584 (M+).

EXAMPLE 127

Synthesis of N1-[4-[(4-phenyl-1-piperazinyl)methyl]benzoyl]-Phe-HPA-NH$_2$

Rink resin-bound N1-[4-(Chloromethyl)benzoyl]-Phe-HPA and 1-phenylpiperazine gave N1-[4-[(4-phenyl-1-piperazinyl)methyl]benzoyl]-Phe-HPA-NH$_2$; MS (EI)=603 (M+).

EXAMPLE 128

Synthesis of N1-[4-[[4-(2-methoxyphenyl)-1-piperazinyl]methyl]benzoyl]-Phe-HPA-NH$_2$ Rink resin-bound N1-[4-(Chloromethyl)benzoyl]-Phe-HPA and 1-(2-methoxyphenyl)-piperazine gave N1-[4-[[4-(2-methoxyphenyl)-1-piperazinyl]methyl]benzoyl]-Phe-HPA-NH$_2$; MS (EI)=633 (M+).

EXAMPLE 129

Synthesis of N1-[4-[(N-benzyl-N-methylamino)methyl]benzoyl]-Phe-HPA-NH$_2$

Rink resin-bound N1-[4-(Chloromethyl)benzoyl]-Phe-HPA and N-benzylmethylamine gave N1-[4-[(N-benzyl-N-methylamino)methyl]benzoyl]-Phe-HPA-NH$_2$; MS (EI)=562 (M+).

EXAMPLE 130

Synthesis of N1-[4-[(4-benzyl-1-piperazinyl)methyl]benzoyl]-Phe-HPA-NH$_2$

Rink resin-bound N1-[4-(Chloromethyl)benzoyl]-Phe-HPA and 1-benzylpiperazine gave N1-[4-[(4-benzyl-1-piperazinyl)methyl]benzoyl]-Phe-HPA-NH$_2$; MS (EI)=617 (M+).

EXAMPLE 131

Synthesis of N1-[4-[(1,2,3,4-tetrahydroisoquinolin-2-yl)methyl]benzoyl]-Phe-HPA-NH$_2$ Rink resin-bound N1-[4-(Chloromethyl)benzoyl]-Phe-HPA and 1,2,3,4-tetrahydroisoquinoline gave N1-[4-[(1,2,3,4-tetrahydroisoquinolin-2-yl)methyl]benzoyl]-Phe-HPA-NH$_2$; MS (EI)=574 (M+).

EXAMPLE 132

Synthesis of N1-[4-[[4-[3-(trifluoromethyl)phenyl]-1-piperazinyl]methyl]benzoyl]-Phe-HPA-NH$_2$ Rink resin-bound N1-[4-(Chloromethyl)benzoyl]-Phe-HPA and 1-[3-(trifluoromethyl)phenyl]piperazine gave N1-[4-[[4-[3-(trifluoromethyl)phenyl]-1-piperazinyl]methyl]benzoyl]-Phe-HPA-NH$_2$; MS (EI)=671 (M+).

EXAMPLE 133

Synthesis of N1-[4-[[N-[2-(3-methoxyphenyl)ethyl]amino]methyl]benzoyl]-Phe-HPA-NH$_2$ Rink resin-bound N1-[4-(Chloromethyl)benzoyl]-Phe-HPA and 3-methoxyphen-ethylamine gave N1-[4-[[N-[2-(3-methoxyphenyl)ethyl]-amino]methyl]benzoyl]-Phe-HPA-NH$_2$; MS (EI)=592 (M+).

EXAMPLE 134

Synthesis of N1-[4-[[4-(4-fluorophenyl)-1-piperazinyl]methyl]benzoyl]-Phe-HPA-NH$_2$ Rink resin-bound N1-[4-(Chloromethyl)benzoyl]-Phe-HPA and 1-(4-fluorophenyl)-piperazine gave N1-[4-[[4-(4-fluorophenyl)-1-piperazinyl]methyl]benzoyl]-Phe-HPA-NH$_2$; MS (EI)=621 (M+).

EXAMPLE 135

Synthesis of N1-[4-[[N-[2-(4-hydroxyphenyl)ethyl]amino]methyl]benzoyl]-Phe-HPA-NH$_2$ Rink resin-bound N1-[4-(Chloromethyl)benzoyl]-Phe-HPA and tyramine gave N1-[4-[[N-[2-(4-hydroxyphenyl)ethyl]amino]methyl]benzoyl]-Phe-HPA-NH$_2$; MS (EI)=578 (M+).

EXAMPLE 136

Synthesis of N1-[4-[N-(3-phenyl-1-propylamino)methyl]benzoyl]-Phe-HPA-NH$_2$

Rink resin-bound N1-[4-(Chloromethyl)benzoyl]-Phe-HPA and 3-phenyl-1-propylamine gave N1-[4-[N-(3-phenyl-1-propylamino)methyl]benzoyl]-Phe-HPA-NH$_2$; MS (EI)=576 (M+).

EXAMPLE 137

Synthesis of N1-[4-[N-(2,5-difluorophenyl)methylamino]methyl]benzoyl]-Phe-BIP-NH$_2$ Rink resin-bound N1-[4-(Chloromethyl)benzoyl]-Phe-BIP and 2,5-difluorobenzylamine gave N1-[4-[N-(2,5-difluorophenyl)methylamino]methyl]benzoyl]-Phe-BIP-NH$_2$; MS (EI)=646 (M+).

EXAMPLE 138

Synthesis of N1-[4-[(4-methyl-1-homopiperazinyl)methyl]benzoyl]-Phe-BIP-NH$_2$

Rink resin-bound N1-[4-(chloromethyl)benzoyl]-Phe-BIP and 1-methylhomopiperazine gave N1-[4-[(4-methyl-1-homopiperazinyl)methyl]benzoyl]-Phe-BIP-NH$_2$; MS (EI)=617 (M+).

EXAMPLE 139

Synthesis of N1-[4-[(4-phenyl-1-piperazinyl)methyl]benzoyl]-Phe-BP-NH$_2$

Rink resin-bound N1-[4-(chloromethyl)benzoyl]-Phe-BIP and 1-phenylpiperazine gave N1-[4-[(4-phenyl-1-piperazinyl)methyl]benzoyl]-Phe-BIP-NH$_2$; MS (EI)=665 (M+).

EXAMPLE 140

Synthesis of N1-[4-[[4-(2-methoxyphenyl)-1-piperazinyl]methyl]benzoyl]-Phe-BIP-NH$_2$ Rink resin-bound N1-[4-(Chloromethyl)benzoyl]-Phe-BIP and 1-(2-methoxyphenyl)-piperazine gave N1-[4-[[4-(2-methoxyphenyl)-1-piperazinyl]methyl]benzoyl]-Phe-BIP-NH$_2$; MS (EI)=695 (M+).

EXAMPLE 141

Synthesis of N1-[4-[(N-benzyl-N-methylamino) methyl]benzoyl]-Phe-BIP-NH$_2$

Rink resin-bound N1-[4-(Chloromethyl)benzoyl]-Phe-BIP and N-benzylmethylamine gave N1-[4-[(N-benzyl-N-methylamino)methyl]benzoyl]-Phe-BIP-NH$_2$; MS (EI)=624 (M+).

EXAMPLE 142

Synthesis of N1-[4-[(4-benzyl-1-pinerazinyl)methyl] benzoyl]-Phe-BIP-NH$_2$

Rink resin-bound N1-[4-(Chloromethyl)benzoyl]-Phe-BIP and 1-benzylpiperazine gave N1-[4-[(4-benzyl-1-piperazinyl)methyl]benzoyl]-Phe-BIP-NH$_2$; MS (EI)=679 (M+).

EXAMPLE 143

Synthesis of N1-[4-[(1,2,3,4-tetrahydroisoquinolin-2-yl)methyl]benzoyl]-Phe-BIP-NH$_2$ Rink resin-bound N1-[4-(Chloromethyl)benzoyl]-Phe-BIP and 1,2,3,4-tetrahydroisoquinoline gave N1-[4-[(1,2,3,4-tetrahydroisoquinolin-2-yl)methyl]benzoyl]-Phe-BIP-NH$_2$; MS (EI)=636 (M+).

EXAMPLE 144

Synthesis of N1-[4-[[4-[3-(trifluoromethyl)phenyl]-1-piperazinyl]methyl]-benzoyl]-Phe-BIP-NH$_2$ Rink resin-bound N1-[4-(Chloromethyl)benzoyl]-Phe-BIP and 1-[3-(trifluoromethyl)-phenyl]piperazine gave N1-[4-[[4-[3-(trifluoromethyl)phenyl]-1-piperazinyl]methyl]-benzoyl]-Phe-BIP-NH$_2$; MS (EI)=733 (M+).

EXAMPLE 145

Synthesis of N1-[4-[N-[2-(3-methoxyphenyl) ethylamino]methyl]benzoyl]-Phe-BIP-NH$_2$ Rink resin-bound N1-[4-(Chloromethyl)benzoyl]-Phe-BIP and 3-methoxyphen-ethylamine gave N1-[4-[N-[2-(3-methoxyphenyl)ethylamino]methyl]benzoyl]-Phe-BIP-NH$_2$; MS (EI)=654 (M+).

EXAMPLE 146

Synthesis of N1-[4-[[4-(4-fluorophenyl)-1-piperazinyl]methyl]benzoyl]-Phe-BIP-NH$_2$ Rink resin-bound N1-[4-(Chloromethyl)benzoyl]-Phe-BIP and 1-(4-fluorophenyl)-piperazine gave N1-[4-[[4-(4-fluorophenyl)-1-piperazinyl]methyl]benzoyl]-Phe-BIP-NH$_2$; MS (EI)=683 (M+).

EXAMPLE 147

Synthesis of N1-[4-[N-[2-(4-hydroxyphenyl) ethylamino]methyl]benzoyl]-Phe-BIP-NH$_2$ Rink resin-bound N1-[4-(Chloromethyl)benzoyl]-Phe-BIP and tyramine gave N1-[4-[N-[2-(4-hydroxyphenyl) ethylamino]methyl]benzoyl]-Phe-BIP-NH$_2$; MS (EI)=640 (M+).

EXAMPLE 148

Synthesis of N1-[4-[N-(3-phenyl-1-propylamino) methyl]benzoyl]-Phe-BIP-NH$_2$

Rink resin-bound N1-[4-(Chloromethyl)benzoyl]-Phe-BIP and 3-phenyl-1-propylamine gave N1-[4-[N-(3-phenyl-1-propylamino)methyl]benzoyl]-Phe-BIP-NH$_2$; MS (EI)=638 (M+).

EXAMPLE 149

Synthesis of N1-[4-[[N-(2,5-difluorophenyl) methylamino]methyl]benzoyl]-Phe-2-NAL-NH$_2$ Rink resin-bound N1-[4-(Chloromethyl)benzoyl]-Phe-2-NAL and 2,5-difluorobenzylamine gave N1-[4-[[N-(2,5-difluorophenyl)methylamino]methyl]benzoyl]-Phe-2-NAL-NH$_2$; MS (EI)=620 (M+).

EXAMPLE 150

Synthesis of N1-[4-[(4-methyl-1-homopiperazinyl) methyl]benzoyl]-Phe-2-NAL-NH$_2$ Rink resin-bound N1-[4-(Chloromethyl)benzoyl]-Phe-2-NAL and 1-methylhomopiperazine gave N1-[4-[(4-methyl-1-homopiperazinyl)methyl]benzoyl]-Phe-2-NAL-NH$_2$; MS (EI)=591 (M+).

EXAMPLE 151

Synthesis of N1-[4-[(4-phenyl-1-piperazinyl) methyl]benzoyl]-Phe-2-NAL-NH$_2$

Rink resin-bound N1-[4-(Chloromethyl)benzoyl]-Phe-2-NAL and 1-phenylpiperazine gave N1-[4-[(4-phenyl-1-piperazinyl)methyl]benzoyl]-Phe-2-NAL-NH$_2$; MS (EI)=639 (M+).

EXAMPLE 152

Synthesis of N1-[4-[[4-(2-methoxyphenyl)-1-piperazinyl]methyl]benzoyl]-Phe-2-NAL-NH$_2$ Rink resin-bound N1-[4-(Chloromethyl)benzoyl]-Phe-2-NAL and 1-(2-methoxyphenyl)-piperazine gave N -[4-[[4-(2-methoxyphenyl)-1-piperazinyl]methyl]benzoyl]-Phe-2-NAL-NH$_2$; MS (EI)=669 (M+).

EXAMPLE 153

Synthesis of N1-[4-[(N-benzyl-N-methylamino) methyl]benzoyl]-Phe-2-NAL-NH$_2$

Rink resin-bound N1-[4-(Chloromethyl)benzoyl]-Phe-2-NAL and N-benzylmethylamine gave N1-[4-[(N-benzyl-N-methylamino)methyl]benzoyl]-Phe-2-NAL-NH$_2$; MS (EI)=598 (M+).

EXAMPLE 154

Synthesis of N1-[4-[(4-benzyl-1-piperazinyl)methyl] benzoyl]-Phe-2-NAL-NH$_2$

Rink resin-bound N1-[4-(Chloromethyl)benzoyl]-Phe-2-NAL and 1-benzylpiperazine gave N1-[4-[(4-benzyl-1-piperazinyl)methyl]benzoyl]-Phe-2-NAL-NH$_2$; MS (EI)=653 (M+).

EXAMPLE 155

Synthesis of N1-[3-[(1,2,3,4-tetrahydroisoguinolin-2-yl)methyl]benzoyl]-Phe-2-NAL-NH$_2$ Rink resin-bound N1-[3-(Chloromethyl)benzoyl]-Phe-2-NAL and 1,2,3,4-tetrahydroisoquinoline gave N1-[3-[(1,2,3,4-tetrahydroisoquinolin-2-yl)methyl]benzoyl]-Phe-2-NAL-NH$_2$; MS (EI)=610 (M+).

EXAMPLE 156

Synthesis of N1-[4-[(1,2,3,4-tetrahydroisoguinolin-2-yl)methy]benzoyl]-Phe-2-NAL-NH$_2$ Rink resin-bound N1-[4-(Chloromethyl)benzoyl]-Phe-2-NAL and 1,2,3,4-tetrahydroisoquinoline gave N1-[4-[(1,2, 3,4-tetrahydroisoquinolin-2-yl)methyl]benzoyl]-Phe-2-NAL-NH$_2$; MS (EI)=610 (M+).

EXAMPLE 157

Synthesis of N1-[4-[[4-[3-(trifluoromethyl)phenyl-1-piperazinyl]methyl]benzoyl]-Phe-2-NAL-NH$_2$ Rink resin-bound N1-[4-(Chloromethyl)benzoyl]-Phe-2-NAL and 1-[3-(trifluoromethyl)phenyl]piperazine gave N1-[4-[[4-[3-(trifluoromethyl)phenyl]-1-piperazinyl]methyl]-benzoyl]-Phe-2-NAL-NH$_2$; MS (EI)=707 (M+).

EXAMPLE 158

Synthesis of N1-[4-[[4-(4-fluorophenyl)-1-piperazinyl]methyl]benzoyl]-Phe-2-NAL-NH$_2$ Rink resin-bound N1-[4-(Chloromethyl)benzoyl]-Phe-2-NAL and 1-(4-fluorophenyl)-piperazine gave N1-[4-[[4-(4-fluorophenyl)-1-piperazinyl]methyl]benzoyl]-Phe-2-NAL-NH$_2$; MS (EI)=657 (M+).

EXAMPLE 159

Synthesis of N1-4-[N-[2-(4-hydroxyphenyl)ethylamino]methyl]benzoyl]-Phe-2-NAL-NH$_2$ Rink resin-bound N1-[4-(Chloromethyl)benzoyl]-Phe-2-NAL and tyramine gave N1-[4-[N-[2-(4-hydroxyphenyl)ethylamino]methyl]benzoyl]-Phe-2-NAL-NH$_2$; MS (EI)=614 (M+).

EXAMPLE 160

Synthesis of N1-[4-[N-(3-phenyl-1-propylamino)methyl]benzoyl]-Phe-2-NAL-NH$_2$

Rink resin-bound N1-[4-(Chloromethyl)benzoyl]-Phe-2-NAL and 3-phenyl-1-propylamine gave N1-[4-[N-(3-phenyl-1-propylamino)methyl]benzoyl]-Phe-2-NAL-NH$_2$; MS (EI)=612 (M+).

EXAMPLE 161

Synthesis of N1-[3-[[4-(2-methoxyphenyl)-1-piperazinyl]methyl]benzoyl]-Phe-Phe-NH$_2$ Rink resin-bound N1-[3-(Chloromethyl)benzoyl]-Phe-Phe and 1-(2-methoxyphenyl)-piperazine gave N1-[3-[[4-(2-methoxyphenyl)-1-piperazinyl]methyl]benzoyl]-Phe-Phe-NH$_2$; MS (EI)=619 (M+).

EXAMPLE 162

Synthesis of N1-[3-[(4-benzyl-1-piperazinyl)methyl]benzoyl]-Phe-Phe-NH$_2$

Rink resin-bound N1-[3-(Chloromethyl)benzoyl]-Phe-Phe and 1-benzylpiperazine gave N1-[3-[(4-benzyl-1-piperazinyl)methyl]benzoyl]-Phe-Phe-NH$_2$; MS (EI)=603 (M+).

EXAMPLE 163

Synthesis of N1-[4-[[4-phenyl-1-piperazinyl]methyl]benzoyl]-Phe-Phe-NH$_2$

Rink resin-bound N1-[4-(Chloromethyl)benzoyl]-Phe-Phe and 1-phenylpiperazine gave N1-[4-[[4-phenyl-1-piperazinyl]methyl]benzoyl]-Phe-Phe-NH$_2$; MS (EI)=589 (M+).

EXAMPLE 164

Synthesis of N1-[4-[[4-(2-methoxyphenyl)-1-piperazinyl]methyl]benzoyl]-Phe-Phe-NH$_2$ Rink resin-bound N1-[4-(Chloromethyl)benzoyl]-Phe-Phe and 1-(2-methoxyphenyl)-piperazine gave N1-[4-[[4-(2-methoxyphenyl)-1-piperazinyl]methyl]benzoyl]-Phe-Phe-NH$_2$; MS (EI)=619 (M+).

EXAMPLE 165

Synthesis of N1-[4-[(N-benzyl-N-methylamino)methyl]benzoyl]-Phe-Phe-NH$_2$

Rink resin-bound N1-[4-(Chloromethyl)benzoyl]-Phe-Phe and N-benzylmethylamine gave N1-[4-[(N-benzyl-N-methylamino)methyl]benzoyl]-Phe-Phe-NH$_2$; MS (EI)=548 (M+).

EXAMPLE 166

Synthesis of N1-[4-[(4-benzyl-1-piperazinyl)methyl]benzoyl]-Phe-Phe-NH$_2$

Rink resin-bound N1-[4-(Chloromethyl)benzoyl]-Phe-Phe and 1-benzylpiperazine gave N1-[4-[(4-benzyl-1-piperazinyl)methyl]benzoyl]-Phe-Phe-NH$_2$; MS (EI)=603 (M+).

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound of structure 33:

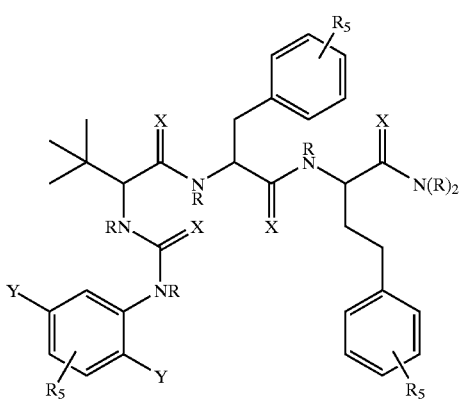

wherein
X represents, independently for each occurrence, O, S, H₂, or NR;
Y represents, independently for each occurrence, F, Cl, Br, or I;
R represents, independently for each occurrence, H, Me, lower alkyl, lower heteroalkyl, aryl, heteroaryl, aralkyl, or heteroaralkyl;
R₅, independently for each occurrence, is absent, or present between one and the maximum number of times permitted by the additional substitution on the relevant aromatic ring;
R₅, when present, is selected independently for each occurrence from the set consisting of Me, lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy; and
the stereochemical configuration at any stereocenter of a compound represented by 33 is R, S, or a mixture of these configurations.

2. The compound of claim 1, wherein X represents, independently for each occurrence, O, or H₂.

3. The compound of claim 1, wherein Y represents, independently for each occurrence, F, or Cl.

4. The compound of claim 1, wherein R represents, independently for each occurrence, H, or lower alkyl.

5. The compound of claim 1, wherein R₅ is absent.

6. The compound of claim 1, wherein X represents, independently for each occurrence, O, or H₂; Y represents, independently for each occurrence, F, or Cl; R represents, independently for each occurrence, H, or lower alkyl; and R₅ is absent.

7. The compound of claim 1, 2, 3, 4, 5, or 6, wherein said compound has an IC₅₀ less than 10 μM against μ, κ, or δ opioid receptors using [³H]Diprenorphine, [³H]Diprenorphine, or [³H]Naltrindole, respectively, as the standard in an assay based on opioid receptors from mammalian brain tissue.

8. The compound of claim 1, 2, 3, 4, 5, or 6, wherein said compound has an IC₅₀ less than 1 μM against μ, κ, or δ opioid receptors using [³H]Diprenorphine, [³H]Diprenorphine, or [³H]Naltrindole, respectively, as the standard in an assay based on opioid receptors from mammalian brain tissue.

9. The compound of claim 1, 2, 3, 4, 5, or 6, wherein said compound has an IC₅₀ less than 100 nM against μ, κ, or δ opioid receptors using [³H]Diprenorphine, [³H]Diprenorphine, or [³H]Naltrindole, respectively, as the standard in an assay based on opioid receptors from mammalian brain tissue.

10. The compound of claim 1, 2, 3, 4, 5, or 6, wherein said compound is an agonist of a mammalian opioid receptor.

11. The compound of claim 1, 2, 3, 3, 4, 5, or 6, wherein said compound is an antagonist of a mammalian opioid receptor.

12. The compound according to claim 1 wherein R is methyl.

13. The compound according to claim 1 wherein R₅ is methyl.

14. A compound of structure 35:

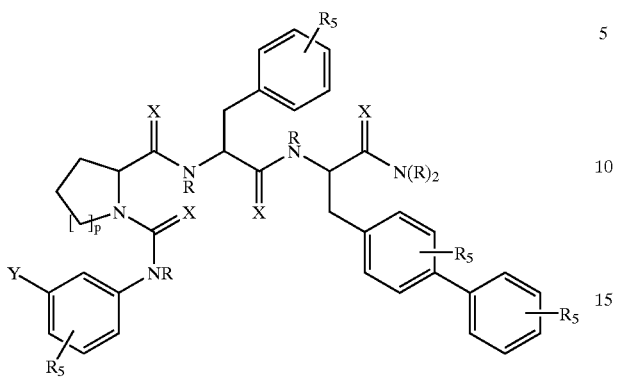

wherein
X represents, independently for each occurrence, O, S, H₂, or NR;
Y represents —OR;
R represents, independently for each occurrence, H, Me, lower alkyl, lower heteroalkyl, aryl, heteroaryl, aralkyl, or heteroaralkyl;
$R_5$, independently for each occurrence, is absent, or present between one and the maximun number of times permitted by the additional substitution on the relevant aromatic ring;
$R_5$, when present, is selected independently for each occurrence from the set consisting of Me, lower alkyl, lower heteroalkyl, aryl, heteroaryl aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;
p is an integer in the range 1 to 3 inclusive; and
the stereochemical configuration at any stereocenter of a compound represented by 35 may be R, S, or a mixture of these configurations.

15. The compound of claim 14, wherein X represents, independently for each occurrence, O, or H₂.

16. The compound of claim 14, wherein R represents, independently for each occurrence, H, or lower alkyl.

17. The compound of claim 14, wherein $R_5$ is absent.

18. The compound of claim 14, wherein X represents, independently for each occurrence, O, or H₂; R represents, independently for each occurrence, H, or lower alkyl; and $R_5$ is absent.

19. The compound of claim 14, 15, 16, 17, 18, wherein said compound has an $IC_{50}$ less than 10 μM against μ, κ, or δ opioid receptors using [³H]Diprenorphine, [³H]Diprenorphine, or [³H]Naltrindole, respectively, as the standard in an assay based on opioid receptors from mammalian brain tissue.

20. The compound of claim 14, 15, 16, 17, 18, wherein said compound has an $IC_{50}$ less than 1 μM against μ, κ, or δ opioid receptors using [³H]Diprenorphine, [³H]Diprenorphine, or [³H]Naltrindole, respectively, as the standard in an assay based on opioid receptors from mammalian brain tissue.

21. The compound of claim 14, 15, 16, 17, 18, wherein said compound has an $IC_{50}$ less than 100 nM against μ, κ, or δ opioid receptors using [³H]Diprenorphine, [³H]Diprenorphine, or [³H]Naltrindole, respectively, as the standard in an assay based on opioid receptors from mammalian brain tissue.

22. The compound of claim 14, 15, 16, 17, 18, wherein said compound is an agonist of a mammalian opioid receptor.

23. The compound of claim 14, 15, 16, 17, 18, wherein said compound is an antagonist of a mammalian opioid receptor.

24. The compound according to claim 14 wherein R is methyl.

25. The compound according to claim 14 wherein $R_5$ is methyl.

26. A compound of structure 45:

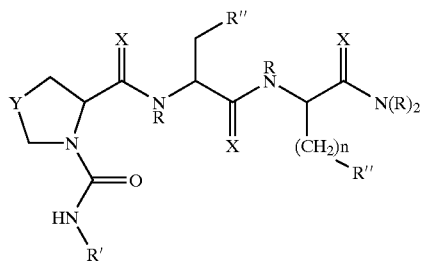

wherein
X independently for each occurrence represents O, S, H₂, or NR:
Y represents $(C(R_2))_p$, $(O(CR_2)_m)$, $(S(CR_2)_m)$, $(C(O)(CR_2)_m)$, $(CH(OR)(CR_2)_m)$, or $(CR(NR_2)(CR_2)_m)$;
R independently for each occurrence represents H, Me, lower alkyl, lower heteroalkyl, aryl, heteroaryl, aralkyl, heteroaralkyl, cycloalkyl, or heterocycloalkyl;
R' represents lower alkyl, lower heteroalkyl, aryl, heteroaryl, aralkyl, heteroaralkyl, cycloalkyl, or heterocycloalkyl;
R" independently for each occurrence represents aryl, heteroaryl, aralkyl, or heteroaralkyl;
m is an integer in the range 0 to 2 inclusive;
p is an integer in the range 1 to 3 inclusive;
n is an integer in the range 0 to 3 inclusive; and
the stereochemical configuration at any stereocenter of a compound represented by 45 is R, S, or a mixture of these configurations.

27. The compounds of claim 26, wherein X independently for each occurrence represents O or H₂.

28. The compound of claim 26, wherein Y represents $CR_2$ or S.

29. The compound of claim 26, wherein R independently for each occurrence represents H, lower alkyl, lower heteroalkyl, aryl, heteroaryl, aralkyl, or heteroaralkyl.

30. The compound of claim 26, wherein R" independently for each occurrence represents aryl or heteroaryl.

31. The compound of claim 26, wherein X independently for each occurrence represents O or H₂; Y represents $CR_2$ or S; R independently for each occurrence represents H, lower alkyl, lower heteroalkyl, aryl, heteroaryl, aralkyl, or heteroaralkyl; and R" independently for each occurrence represents aryl or heteroaryl.

32. The compound of claim 26, 27, 28, 29, 30, 31, wherein said compound has an $IC_{50}$ less than 10 μM against μ, κ, or δ opioid receptors using [³H]Diprenorphine, [³H]Diprenorphine, or [³H]Naltrindole, respectively, as the standard in an assay based on opioid receptors from mammalian brain tissue.

33. The compound of claim 26, 27, 28, 29, 30, 31, wherein said compound has an $IC_{50}$ less than 1 μM against μ, κ, or δ opioid receptors using [³H]Diprenorphine, [³H]Diprenorphine, or [³H]Naltrindole, respectively, as the standard in an assay based on opioid receptors from mammalian brain tissue.

34. The compound of claim 26, 27, 28, 29, 30, 31, wherein said compound has an IC$_{50}$ less than 100 nM against μ, κ, or δ opioid receptors using [³H]Diprenorphine, [³H]Diprenorphine, or [³H]Naltrindole, respectively, as the standard in an assay based on opioid receptors from mammalian brain tissue.

35. The compound of claim 26, 27, 28, 29, 30, 31, wherein said compound is an agonist of a mammalian opioid receptor.

36. The compound of claim 26, 27, 28, 29, 30, 31, wherein said compound is an antagonist of a mammalian opioid receptor.

37. The compound according to claim 26 wherein R is methyl.

38. The compound according to claim 26 wherein R' is methyl.

39. A compound of structure 46:

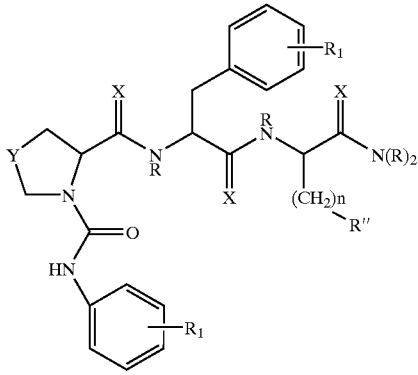

46 wherein
X independently for each occurrence repesents O, S, H$_2$, or NR;
Y represents (C(R$_2$))$_p$, (O(CR$_2$)$_m$), (S(CR$_2$)$_m$), (C(O)(CR$_2$)$_m$), (CH(OR)(CR$_2$)$_m$), or (CR(NR$_2$)(CR$_2$)$_m$);
R independently for each occurrence represents H, lower alkyl, lower heteroalkyl, aryl, heteroaryl, aralkyl, heteroaralkyl, cycloalkyl, or heterocycloalkyl;
R" independently for each occurrence represents aryl, heteroaryl, aralkyl, or heteroaralkyl;
R$_1$, independently for each occurrence, is absent, or present between one and the maximum number of times permitted by the additional substitution on the relevant aromatic ring;
R$_1$, when present, is selected independently for each occurrence from the set consisting of lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;
p is an integer in the range 1 to 3 inclusive;
m is an integer in the range 0 to 2 inclusive;
n is an integer in the range 0 to 3 inclusive; and
the stereochemical configuration at any stereocenter of a compound represented by 46 is R, S, or a mixture of these configurations.

40. The compound of claim 39, wherein X independently for each occurrence represents O or H$_2$.

41. The compound of claim 39, wherein Y represents CR$_2$ or S.

42. The compound of claim 39, wherein R independently for each occurrence represents H, lower alkyl, lower heteroalkyl aryl, heteroaralkyl.

43. The compound of claim 39, wherein R" represents aryl or heteroaryl.

44. The compound of claim 39, wherein X independently for each occurrence represents O or H$_2$; Y represents CR$_2$ or S; R independently for each occurrence represents H, lower alkyl, lower heteroalkyl, aryl, heteroaryl, aralkyl, or heteroaralkyl; and R" represents aryl or heteroaryl.

45. The compound of claim 39, 40, 41, 42, 43, 44, wherein said compound has an IC$_{50}$ less than 10 μM against μ, κ, or δ opioid receptors using [³H]Diprenorphine, [³H]Diprenorphine, or [³H]Naltrindole, respectively, as the standard in an assay based on opioid receptors from mammalian brain tissue.

46. The compound of claim 39, 40, 41, 42, 43, 44, wherein said compound has an IC$_{50}$ less than 1 μM against μ, κ, or δ opioid receptors using [³H]Diprenorphine, [³H]Diprenorphine, or [³H]Naltrindole, respectively, as the standard in an assay based on opioid receptors from mammalian brain tissue.

47. The compound of claim 39, 40, 41, 42, 43, 44, wherein said compound has an IC$_{50}$ less than 100 nM against μ, κ, or δ opioid receptors using [³H]Diprenorphine, [³H]Diprenorphine, or [³H]Naltrindole, respectively, as the standard in an assay based on opioid receptors from mammalian brain tissue.

48. The compound of claim 39, 40, 41, 42, 43, 44, wherein said compound is an agonist of a mammalian opioid receptor.

49. The compound of claim 39, 40, 41, 42, 43, 44, wherein said compound is an antagonist of a mammalian opioid receptor.

50. The compound according to claim 39 wherein R is methyl.

51. The compound according to claim 39 R$_1$ is methyl.

52. A compound of structure 47:

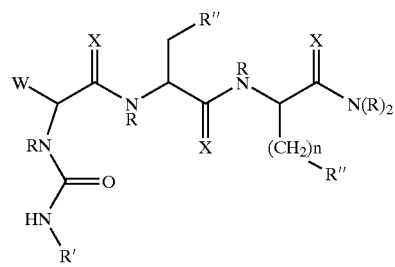

47 wherein

X independently for each occurrence represents O, S, or NR;

W represents lower alkyl;

R independently for each occurrence represents H, Me, ethyl, propyl, isopropyl, butyl, isobutyl, sec-butyl, tert-butyl, lower heteroalkyl, aryl, heteroaryl, aralkyl, heteroaralkyl, cycloalkyl, or heterocycloalkyl;

R' represents lower alkyl, lower heteroalkyl, aryl, heteroaryl, aralkyl, heteroaralkyl, cycloalkyl, or heterocycloalkyl;

R" independently for each occurrence represents aryl, heteroaryl, aralkyl, or heteroaralkyl;

n is an integer in the range 0 to 3 inclusive; and the stereochemical configuration at any stereocenter of a compound represented by 47 is R, S, or a mixture of these configurations.

53. The compound of claim 52, wherein X independently for each occurrence represents O [or $H_2$].

54. The compound of claim 52, wherein W represents methyl, ethyl, n-propyl, iso-propyl, or tert-butyl.

55. The compound of claim 52, wherein R independently for each occurrence represents H, methyl, ethyl, propyl, isopropyl, butyl, isobutyl, sec-butyl, tert-butyl, [lower alkyl,] lower heteroalkyl, aryl, heteroaryl, aralkyl, or heteroaralkyl.

56. The compound of claim 52, wherein R" independently for each occurrence represents aryl or heteroaryl.

57. The compound of claim 52, wherein X independently for each occurrence represents O [or $H_2$]; W represent methyl, ethyl, n-propyl, iso-propyl, or tert-butyl; R independently for each occurrence represents H, methyl, ethyl, propyl, isopropyl, butyl, isobutyl, sec-butyl, tert-butyl, [lower alkyl,] lower heteroalkyl, aryl, heteroaryl, aralkyl, or heteroaralkyl; and R" independently for each occurrence represents aryl or heteroaryl.

58. The compound of claim 52, 53, 54, 55, 56, 57, wherein said compound has an $IC_{50}$ less than 10 μM against μ, κ, or δ opioid receptors using [$^3$H]Diprenorphine, [$^3$H]Diprenorphine, or [$^3$H]Naltrindole, respectively, as the standard in an assay based on opioid receptors from mammalian brain tissue.

59. The compound of claim 52, 53, 54, 55, 56, 57, wherein said compound has an $IC_{50}$ less than 1 μM against μ, κ, or δ opioid receptors using [$^3$H]Diprenorphine, [$^3$H]Diprenorphine, or [$^3$H]Naltrindole, respectively, as the standard in an assay based on opioid receptors from mammalian brain tissue.

60. The compound of claim 52, 53, 54, 55, 56, 57, wherein said compound has an $IC_{50}$ less than 100 nM against μ, κ, or δ opioid receptors using [$^3$H]Diprenorphine, [$^3$H]Diprenorphine, or [$^3$H]Naltrindole, respectively, as the standard in an assay based on opioid receptors from mammalian brain tissue.

61. The compound of claim 52, 53, 54, 55, 56, 57, wherein said compound is an agonist of a mammalian opioid receptor.

62. The compound of claim 52, 53, 54, 55, 56, 57, wherein said compound is an antagonist of a mammalian opioid receptor.

63. The compound according to claim 52 wherein W is methyl.

64. The compound according to claim 52 wherein R is methyl.

65. The compound according to claim 52 wherein R' is methyl.

66. A compound of structure 48:

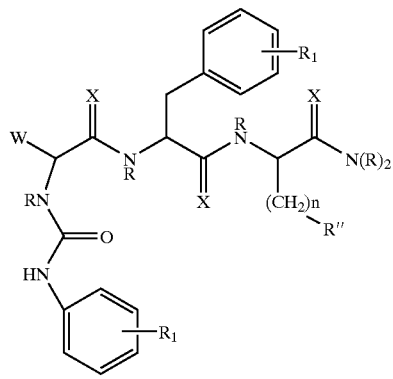

48 wherein

X independently for each occurrence represents O, S, $H_2$, or NR;

W represents lower alkyl;

R independently for each occurrence represents H, lower alkyl, lower heteroalkyl, aryl, heteroaryl, aralkyl, heteroaralkyl, cycloalkyl, or heterocycloalkyl;

R" independently for each occurrence represents aryl, heteroaryl, aralkyl, or heteroaralkyl;

$R_1$, independently for each occurrence, is absent, or present between one and the maximum number of times permitted by the additional substitution on the relevant aromatic ring;

$R_1$, when present, is selected independently for each occurrence from the set consisting of lower alkyl, lower heteroalkyl, aryl, heteroaryl, aralkyl, heteroaralkyl, cycloalkyl, heterocycloalkyl, halogen, hydroxyl, alkoxyl, nitro, nitroso, cyano, acyl, acylamino, amido, sulfonyl, sulfonamido, and acyloxy;

n is an integer in the range 0 to 3 inclusive; and the stereochemical configuration at any stereocenter of a compound represented by 48 is R, S, or a mixture of these configurations.

67. The compound of claim 66, wherein X independently for each occurrence represents O or $H_2$.

68. The compound of claim 66, wherein W represents methyl, ethyl, n-propyl, iso-propyl, or tert-butyl.

69. The compound of claim 66, wherein R independently for each occurrence represents H, lower alkyl, lower heteroalkyl, aryl, heteroaryl, aralkyl, or heteroaralkyl.

70. The compound of claim 66, wherein R" independently for each occurrence represents aryl or heteroaryl.

71. The compound of claim 66, wherein X independently for each occurrence represents O or $H_2$; W represents methyl, ethyl, n-propyl, iso-propyl, or tert-butyl; R independently for each occurrence represents H, lower alkyl, lower heteroalkyl, aryl, heteroaryl, aralkyl, or heteroaralkyl; and R" independently for each occurrence represents aryl or heteroaryl.

72. The compound of claim 66, 67, 68, 69, 70, 71, wherein said compound has an $IC_{50}$ less than 10 μM against μ, κ, or δ opioid receptors using [$^3$H]Diprenorphine, [$^3$H]Diprenorphine, or [$^3$H]Naltrindole, respectively, as the standard in an assay based on opioid receptors from mammalian brain tissue.

73. The compound of claim 66, 67, 68, 69, 70, 71, wherein said compound has an $IC_{50}$ less than 1 μM against μ, κ, or δ opioid receptors using [$^3$H]Diprenorphine, [$^3$H]Diprenorphine, or [$^3$H]Naltrindole, respectively, as the standard in an assay based on opioid receptors from mammalian brain tissue.

74. The compound of claim 66, 67, 68, 69, 70, 71, wherein said compound has an IC$_{50}$ less than 100 nM against μ, κ, or δ opioid receptors using [$^3$H]Diprenorphine, [$^3$H]Diprenorphine, or [$^3$H]Naltrindole, respectively, as the standard in an assay based on opioid receptors from mammalian brain tissue.

75. The compound of claim 66, 67, 68, 69, 70, 71, wherein said compound is an agonist of a mammalian opioid receptor.

76. The compound of claim 66, 67, 68, 69, 70, 71, wherein said compound is an antagonist of a mammalian opioid receptor.

77. The compound according to claim 66 wherein W is methyl.

78. The compound according to claim 66 wherein R is methyl.

79. The compound according to claim 66 wherein R$_1$ is methyl.

* * * * *

SEQUENCE LISTING

<160> NUMBER OF SEQ ID NOS: 2

<210> SEQ ID NO 1
<211> LENGTH: 4
<212> TYPE: PRT
<213> ORGANISM: Bovine sp.

<400> SEQUENCE: 1

Tyr Pro Phe Phe
 1

<210> SEQ ID NO 2
<211> LENGTH: 4
<212> TYPE: PRT
<213> ORGANISM: Bovine sp.

<400> SEQUENCE: 2

Tyr Pro Trp Phe
 1